United States Patent
Zelder et al.

(10) Patent No.: US 8,778,645 B2
(45) Date of Patent: Jul. 15, 2014

(54) METHOD FOR THE PRODUCTION OF GLUTACONATE

(75) Inventors: Oskar Zelder, Speyer (DE); Wolfgang Buckel, Marburg (DE); Ivana Djurdjevic, Marburg (DE)

(73) Assignee: BASF SE, Ludwigshafen (DE)

( * ) Notice: Subject to any disclaimer, the term of this patent is extended or adjusted under 35 U.S.C. 154(b) by 208 days.

(21) Appl. No.: 13/144,616

(22) PCT Filed: Jan. 15, 2010

(86) PCT No.: PCT/EP2010/050475
§ 371 (c)(1),
(2), (4) Date: Jul. 14, 2011

(87) PCT Pub. No.: WO2010/081885
PCT Pub. Date: Jul. 22, 2010

(65) Prior Publication Data
US 2012/0021472 A1   Jan. 26, 2012

(30) Foreign Application Priority Data
Jan. 15, 2009  (EP) ..................................... 09150669

(51) Int. Cl.
*C12P 21/06*   (2006.01)
*C12P 7/44*    (2006.01)
*C12N 9/00*    (2006.01)
*C12N 1/20*    (2006.01)
*C12N 15/00*   (2006.01)
*C07H 21/04*   (2006.01)

(52) U.S. Cl.
USPC ....... 435/142; 435/69.1; 435/183; 435/252.3; 435/320.1; 536/23.2

(58) Field of Classification Search
None
See application file for complete search history.

(56) References Cited

FOREIGN PATENT DOCUMENTS

WO   WO-2009/046828 A1   4/2009

OTHER PUBLICATIONS

Selmer et al. J Biol Chem. Jul. 23, 1999;274(30):20772-8.*
Chica et al. Curr Opin Biotechnol. Aug. 2005;16(4):378-84.*
Sen et al. Appl Biochem Biotechnol. Dec. 2007;143(3):212-23.*
Bendrat, K., et al., "Identification of the gene encoding the activator of (R)-2-hydroxyglutaryl-CoA dehydratase from *Acidaminococcus fermentans* by gene expression in *Escherichia coil*," FEBS 12921 (Aug. 1993), vol. 329, No. 3, pp. 329-331.
Buckel, W., "Unusual enzymes involved in five pathways of glutamate fermentation," Appl Microbiol Biotechnol (2001), vol. 57, pp. 263-273.
Buckel, W., et al., "Glutaconate CoA-Transferase from *Acidaminococcus fermentans*," Eur. J. Biochem. (1981), vol. 118, pp. 315-321.
Hoffmann, G.F., "Glutaric aciduria type I: From clinical, biochemical and molecular diversity to successful therapy," J. Inher. Metab. Dis. (1999), vol. 22, pp. 381-391.

(Continued)

*Primary Examiner* — Christian Fronda
(74) *Attorney, Agent, or Firm* — Drinker Biddle & Reath LLP

(57) ABSTRACT

The present invention relates to a novel method for the biocatalytic production of unsaturated dicarboxylic acids by cultivating a recombinant microorganism co-expressing a glutaconate CoA-transferase and a 2-hydroxyglutaryl-CoA dehydratase system. The present invention also relates to corresponding recombinant hosts, recombinant vectors, expression cassettes and nucleic acids suitable for preparing such hosts as well as a method of preparing polyamide or polyester copolymers making use of said dicarboxylic acids as obtained by said biocatalytic production method.

28 Claims, 3 Drawing Sheets

(56) References Cited

OTHER PUBLICATIONS

Locher, K.P., et al., "Crystal Structure of the *Acidaminococcus fermentans* 2-Hydroxyglutaryl-CoA Dehydratase Component A," J. Mol. Biol. (2001), vol. 307, pp. 297-308.

Mack, M., et al., "Location of the two genes encoding glutaconate coenzyme A-transferase at the beginning of the hydroxyglutarate operon in *Acidaminococcus fermentans*," Eur. J. Biochem. (1994), vol. 226, pp. 41-51.

Niu, W., et al., "Benzene-Free Synthesis of Adipic Acid," Biotechnol. Prog. (2002), vol. 18, pp. 201-211.

\* cited by examiner

SEQUENCE LISTING

```
<160> NUMBER OF SEQ ID NOS: 40

<210> SEQ ID NO 1
<211> LENGTH: 996
<212> TYPE: DNA
<213> ORGANISM: Acidaminococcus fermentans
<220> FEATURE:
<221> NAME/KEY: CDS
<222> LOCATION: (1)..(996)

<400> SEQUENCE: 1 atg aag gtt tta tgt tat ggt gta aga gat gta gaa ctg ccg att ttt      48
Met Lys Val Leu Cys Tyr Gly Val Arg Asp Val Glu Leu Pro Ile Phe
1               5                   10                  15 gaa gcc tgc aac aaa gaa ttt ggt tac gac atc aaa tgt gtc cct gat      96
Glu Ala Cys Asn Lys Glu Phe Gly Tyr Asp Ile Lys Cys Val Pro Asp
                20                  25                  30 tat ctg aac acg aaa gaa acc gcc gaa atg gct gct ggc ttt gat gcg     144
Tyr Leu Asn Thr Lys Glu Thr Ala Glu Met Ala Ala Gly Phe Asp Ala
            35                  40                  45 gtt atc ctg cgc ggc aac tgc ttc gcc aat aaa cag aac ctg gac att     192
Val Ile Leu Arg Gly Asn Cys Phe Ala Asn Lys Gln Asn Leu Asp Ile
        50                  55                  60 tac aaa aaa ctg ggc gta aaa tac atc ctg acc cgt acc gcc ggc acg     240
Tyr Lys Lys Leu Gly Val Lys Tyr Ile Leu Thr Arg Thr Ala Gly Thr
65                  70                  75                  80 gat cat atc gat aag gaa tat gcc aag gaa ctg ggc ttc ccc atg gct     288
Asp His Ile Asp Lys Glu Tyr Ala Lys Glu Leu Gly Phe Pro Met Ala
                85                  90                  95 ttc gtt ccc cgt tat tcc ccc aac gcc att gct gaa ctg gct gta acc     336
Phe Val Pro Arg Tyr Ser Pro Asn Ala Ile Ala Glu Leu Ala Val Thr
            100                 105                 110 cag gcc atg atg ctg ctg cgt cat acc gct tac acc act tcc cgc act     384
Gln Ala Met Met Leu Leu Arg His Thr Ala Tyr Thr Thr Ser Arg Thr
        115                 120                 125 gcc aag aag aac ttc aag gtt gat gcc ttc atg ttc tcc aaa gaa gtc     432
Ala Lys Lys Asn Phe Lys Val Asp Ala Phe Met Phe Ser Lys Glu Val
    130                 135                 140
```

```
cgc aac tgc acc gtg ggt gtt gtt ggt ctg ggc cgg atc ggc cgt gtg        480
Arg Asn Cys Thr Val Gly Val Val Gly Leu Gly Arg Ile Gly Arg Val
145                 150                 155                 160 gct gcc cag atc ttc cat ggc atg ggc gct acc gtt atc ggg gaa gac        528
Ala Ala Gln Ile Phe His Gly Met Gly Ala Thr Val Ile Gly Glu Asp
                165                 170                 175 gtt ttc gaa atc aaa ggg atc gaa gat tac tgc acc cag gtt tcc ctg        576
Val Phe Glu Ile Lys Gly Ile Glu Asp Tyr Cys Thr Gln Val Ser Leu
            180                 185                 190 gat gaa gtc ctg gaa aaa tcc gac atc atc acc atc cat gct ccg tac        624
Asp Glu Val Leu Glu Lys Ser Asp Ile Ile Thr Ile His Ala Pro Tyr
        195                 200                 205 atc aaa gaa aac ggc gct gtg gtt acc cgc gat ttc ttg aag aag atg        672
Ile Lys Glu Asn Gly Ala Val Val Thr Arg Asp Phe Leu Lys Lys Met
    210                 215                 220 aaa gac ggc gcc atc ctg gtg aac tgc gct cgc ggc cag ctg gtt gac        720
Lys Asp Gly Ala Ile Leu Val Asn Cys Ala Arg Gly Gln Leu Val Asp
225                 230                 235                 240 acc gaa gct gtc atc gaa gct gtg gaa agc ggt aaa ctg ggc ggc tac        768
Thr Glu Ala Val Ile Glu Ala Val Glu Ser Gly Lys Leu Gly Gly Tyr
                245                 250                 255 ggc tgc gac gtt ctg gat ggg gaa gcc agc gta ttc ggc aag gat ctg        816
Gly Cys Asp Val Leu Asp Gly Glu Ala Ser Val Phe Gly Lys Asp Leu
            260                 265                 270 gaa ggc cag aaa ctg gaa aat ccg ctg ttc gaa aaa ctg gtt gac ctg        864
Glu Gly Gln Lys Leu Glu Asn Pro Leu Phe Glu Lys Leu Val Asp Leu
        275                 280                 285 tat ccc aga gtc ctg atc acc ccg cat ctg ggc tcc tac acc gac gaa        912
Tyr Pro Arg Val Leu Ile Thr Pro His Leu Gly Ser Tyr Thr Asp Glu
    290                 295                 300 gcc gta aag aac atg gtg gaa gtt tcc tac cag aac ctg aaa gat ctg        960
Ala Val Lys Asn Met Val Glu Val Ser Tyr Gln Asn Leu Lys Asp Leu
305                 310                 315                 320 gct gaa acc ggc gac tgc ccc aac aag atc aaa taa                        996
Ala Glu Thr Gly Asp Cys Pro Asn Lys Ile Lys
                325                 330

<210> SEQ ID NO 2
<211> LENGTH: 331
<212> TYPE: PRT
<213> ORGANISM: Acidaminococcus fermentans

<400> SEQUENCE: 2

Met Lys Val Leu Cys Tyr Gly Val Arg Asp Val Glu Leu Pro Ile Phe
1               5                   10                  15

Glu Ala Cys Asn Lys Glu Phe Gly Tyr Asp Ile Lys Cys Val Pro Asp
                20                  25                  30

Tyr Leu Asn Thr Lys Glu Thr Ala Glu Met Ala Ala Gly Phe Asp Ala
            35                  40                  45

Val Ile Leu Arg Gly Asn Cys Phe Ala Asn Lys Gln Asn Leu Asp Ile
        50                  55                  60

Tyr Lys Lys Leu Gly Val Lys Tyr Ile Leu Thr Arg Thr Ala Gly Thr
65                  70                  75                  80

Asp His Ile Asp Lys Glu Tyr Ala Lys Glu Leu Gly Phe Pro Met Ala
                85                  90                  95

Phe Val Pro Arg Tyr Ser Pro Asn Ala Ile Ala Glu Leu Ala Val Thr
            100                 105                 110

Gln Ala Met Met Leu Leu Arg His Thr Ala Tyr Thr Thr Ser Arg Thr
```

```
            115                 120                 125
Ala Lys Lys Asn Phe Lys Val Asp Ala Phe Met Phe Ser Lys Glu Val
    130                 135                 140

Arg Asn Cys Thr Val Gly Val Gly Leu Gly Arg Ile Gly Arg Val
145                 150                 155                 160

Ala Ala Gln Ile Phe His Gly Met Gly Ala Thr Val Ile Gly Glu Asp
                165                 170                 175

Val Phe Glu Ile Lys Gly Ile Glu Asp Tyr Cys Thr Gln Val Ser Leu
            180                 185                 190

Asp Glu Val Leu Glu Lys Ser Asp Ile Ile Thr Ile His Ala Pro Tyr
        195                 200                 205

Ile Lys Glu Asn Gly Ala Val Val Thr Arg Asp Phe Leu Lys Lys Met
    210                 215                 220

Lys Asp Gly Ala Ile Leu Val Asn Cys Ala Arg Gly Gln Leu Val Asp
225                 230                 235                 240

Thr Glu Ala Val Ile Glu Ala Val Glu Ser Gly Lys Leu Gly Gly Tyr
                245                 250                 255

Gly Cys Asp Val Leu Asp Gly Glu Ala Ser Val Phe Gly Lys Asp Leu
            260                 265                 270

Glu Gly Gln Lys Leu Glu Asn Pro Leu Phe Glu Lys Leu Val Asp Leu
        275                 280                 285

Tyr Pro Arg Val Leu Ile Thr Pro His Leu Gly Ser Tyr Thr Asp Glu
    290                 295                 300

Ala Val Lys Asn Met Val Glu Val Ser Tyr Gln Asn Leu Lys Asp Leu
305                 310                 315                 320

Ala Glu Thr Gly Asp Cys Pro Asn Lys Ile Lys
                325                 330

<210> SEQ ID NO 3
<211> LENGTH: 965
<212> TYPE: DNA
<213> ORGANISM: Acidaminococcus fermentans
<220> FEATURE:
<221> NAME/KEY: CDS
<222> LOCATION: (1)..(963)

<400> SEQUENCE: 3 ttg agt aaa gta atg acg tta aaa gac gca atc gcc aag tat gtg cac        48
Leu Ser Lys Val Met Thr Leu Lys Asp Ala Ile Ala Lys Tyr Val His
1               5                   10                  15 agt ggt gat cac att gct ctg ggt ggt ttt acg acg gac cgt aaa ccc        96
Ser Gly Asp His Ile Ala Leu Gly Gly Phe Thr Thr Asp Arg Lys Pro
            20                  25                  30 tat gcg gct gtg ttc gaa atc ctg aga cag ggt atc acg gat ctg acc       144
Tyr Ala Ala Val Phe Glu Ile Leu Arg Gln Gly Ile Thr Asp Leu Thr
        35                  40                  45 ggt ctg ggc ggc gct gcc ggc ggc gac tgg gat atg ctg atc ggc aac       192
Gly Leu Gly Gly Ala Ala Gly Gly Asp Trp Asp Met Leu Ile Gly Asn
    50                  55                  60 ggc cgt gtg aaa gcc tac atc aac tgc tac acc gcc aac tcc ggt gtg       240
Gly Arg Val Lys Ala Tyr Ile Asn Cys Tyr Thr Ala Asn Ser Gly Val
65                  70                  75                  80 acc aac gtt tcc aga cgg ttc aga aaa tgg ttc gaa gcc ggc aaa ctg       288
Thr Asn Val Ser Arg Arg Phe Arg Lys Trp Phe Glu Ala Gly Lys Leu
                85                  90                  95 acc atg gaa gac tat tcc cag gat gtt atc tac atg atg tgg cat gcc       336
Thr Met Glu Asp Tyr Ser Gln Asp Val Ile Tyr Met Met Trp His Ala
            100                 105                 110
```

```
gcc gct ctg ggc ctg ccc ttc ctg cct gta acc ctg atg cag ggc tcc        384
Ala Ala Leu Gly Leu Pro Phe Leu Pro Val Thr Leu Met Gln Gly Ser
            115                 120                 125 ggc ctg acc gat gaa tgg ggc atc agc aag gaa gtc cgt aaa acc ctg        432
Gly Leu Thr Asp Glu Trp Gly Ile Ser Lys Glu Val Arg Lys Thr Leu
    130                 135                 140 gac aaa gtt cct gat gac aaa ttc aaa tac atc gac aac ccc ttc aaa        480
Asp Lys Val Pro Asp Asp Lys Phe Lys Tyr Ile Asp Asn Pro Phe Lys
145                 150                 155                 160 ccg ggt gaa aaa gtc gtg gct gtt cct gtt ccg cag gtt gat gtg gcc        528
Pro Gly Glu Lys Val Val Ala Val Pro Val Pro Gln Val Asp Val Ala
                165                 170                 175 atc atc cat gcc cag cag gct tct ccc gat ggc acc gtt cgc atc tgg        576
Ile Ile His Ala Gln Gln Ala Ser Pro Asp Gly Thr Val Arg Ile Trp
            180                 185                 190 ggc ggc aaa ttc cag gat gtg gat att gct gaa gca gcc aaa tac acc        624
Gly Gly Lys Phe Gln Asp Val Asp Ile Ala Glu Ala Ala Lys Tyr Thr
        195                 200                 205 atc gtt acc tgc gaa gaa atc att tct gat gaa gaa atc aga aga gat        672
Ile Val Thr Cys Glu Glu Ile Ile Ser Asp Glu Glu Ile Arg Arg Asp
    210                 215                 220 ccc acc aag aac gat atc ccc ggc atg tgc gta gat gct gtt gtc ctg        720
Pro Thr Lys Asn Asp Ile Pro Gly Met Cys Val Asp Ala Val Val Leu
225                 230                 235                 240 gct cct tac ggt gca cat cct tct cag tgc tat ggc ctg tac gac tac        768
Ala Pro Tyr Gly Ala His Pro Ser Gln Cys Tyr Gly Leu Tyr Asp Tyr
                245                 250                 255 gac aat ccg ttc ctg aaa gtc tat gac aag gtc tcc aag acc cag gaa        816
Asp Asn Pro Phe Leu Lys Val Tyr Asp Lys Val Ser Lys Thr Gln Glu
            260                 265                 270 gac ttc gat gcc ttc tgc aag gaa tgg gtg ttc gac ctg aag gat cat        864
Asp Phe Asp Ala Phe Cys Lys Glu Trp Val Phe Asp Leu Lys Asp His
        275                 280                 285 gac gaa tac ctg aac aaa ctg ggt gcc act cgt ctg atc aac ctg aag        912
Asp Glu Tyr Leu Asn Lys Leu Gly Ala Thr Arg Leu Ile Asn Leu Lys
    290                 295                 300 gtt gtt cct ggt ctg ggc tac cac atc gac atg acg aag gag gac aaa        960
Val Val Pro Gly Leu Gly Tyr His Ile Asp Met Thr Lys Glu Asp Lys
305                 310                 315                 320 taa ca                                                                 965

<210> SEQ ID NO 4
<211> LENGTH: 320
<212> TYPE: PRT
<213> ORGANISM: Acidaminococcus fermentans

<400> SEQUENCE: 4

Leu Ser Lys Val Met Thr Leu Lys Asp Ala Ile Ala Lys Tyr Val His
1               5                   10                  15

Ser Gly Asp His Ile Ala Leu Gly Gly Phe Thr Thr Asp Arg Lys Pro
            20                  25                  30

Tyr Ala Ala Val Phe Glu Ile Leu Arg Gln Gly Ile Thr Asp Leu Thr
        35                  40                  45

Gly Leu Gly Gly Ala Ala Gly Gly Asp Trp Asp Met Leu Ile Gly Asn
    50                  55                  60

Gly Arg Val Lys Ala Tyr Ile Asn Cys Tyr Thr Ala Asn Ser Gly Val
65                  70                  75                  80

Thr Asn Val Ser Arg Arg Phe Arg Lys Trp Phe Glu Ala Gly Lys Leu
```

```
                    85                  90                  95
Thr Met Glu Asp Tyr Ser Gln Asp Val Ile Tyr Met Met Trp His Ala
            100                 105                 110
Ala Ala Leu Gly Leu Pro Phe Leu Pro Val Thr Leu Met Gln Gly Ser
            115                 120                 125
Gly Leu Thr Asp Glu Trp Gly Ile Ser Lys Glu Val Arg Lys Thr Leu
            130                 135                 140
Asp Lys Val Pro Asp Lys Phe Lys Tyr Ile Asp Asn Pro Phe Lys
145                 150                 155                 160
Pro Gly Glu Lys Val Val Ala Val Pro Val Pro Gln Val Asp Val Ala
            165                 170                 175
Ile Ile His Ala Gln Gln Ala Ser Pro Asp Gly Thr Val Arg Ile Trp
            180                 185                 190
Gly Gly Lys Phe Gln Asp Val Asp Ile Ala Glu Ala Ala Lys Tyr Thr
            195                 200                 205
Ile Val Thr Cys Glu Glu Ile Ile Ser Asp Glu Glu Ile Arg Arg Asp
            210                 215                 220
Pro Thr Lys Asn Asp Ile Pro Gly Met Cys Val Asp Ala Val Val Leu
225                 230                 235                 240
Ala Pro Tyr Gly Ala His Pro Ser Gln Cys Tyr Gly Leu Tyr Asp Tyr
            245                 250                 255
Asp Asn Pro Phe Leu Lys Val Tyr Asp Lys Val Ser Lys Thr Gln Glu
            260                 265                 270
Asp Phe Asp Ala Phe Cys Lys Glu Trp Val Phe Asp Leu Lys Asp His
            275                 280                 285
Asp Glu Tyr Leu Asn Lys Leu Gly Ala Thr Arg Leu Ile Asn Leu Lys
            290                 295                 300
Val Val Pro Gly Leu Gly Tyr His Ile Asp Met Thr Lys Glu Asp Lys
305                 310                 315                 320

<210> SEQ ID NO 5
<211> LENGTH: 801
<212> TYPE: DNA
<213> ORGANISM: Acidaminococcus fermentans
<220> FEATURE:
<221> NAME/KEY: CDS
<222> LOCATION: (1)..(801)

<400> SEQUENCE: 5 atg gct gat tac acg aat tat acc aat aaa gaa atg cag gct gtg acc      48
Met Ala Asp Tyr Thr Asn Tyr Thr Asn Lys Glu Met Gln Ala Val Thr
1               5                   10                  15 att gcc aag cag atc aaa aat ggt cag gtt gta acg gtt ggt acc ggt      96
Ile Ala Lys Gln Ile Lys Asn Gly Gln Val Val Thr Val Gly Thr Gly
                20                  25                  30 ctg cct ctg atc ggc gcc agc gtg gcc aag aga gtc tat gct cct gac     144
Leu Pro Leu Ile Gly Ala Ser Val Ala Lys Arg Val Tyr Ala Pro Asp
            35                  40                  45 tgc cac atc atc gtg gaa agc ggt ctg atg gac tgc tcc ccg gtg gaa     192
Cys His Ile Ile Val Glu Ser Gly Leu Met Asp Cys Ser Pro Val Glu
        50                  55                  60 gtt ccc cgt tcc gta ggt gac ctg cgg ttc atg gct cac tgc ggc tgc     240
Val Pro Arg Ser Val Gly Asp Leu Arg Phe Met Ala His Cys Gly Cys
65                  70                  75                  80 atc tgg ccg aac gtc cgg ttc gtg ggc ttc gaa atc aac gaa tac ctg     288
Ile Trp Pro Asn Val Arg Phe Val Gly Phe Glu Ile Asn Glu Tyr Leu
                85                  90                  95
```

```
cac aag gcc aac cgt ctg atc gcc ttc atc ggc ggg gcc cag atc gat        336
His Lys Ala Asn Arg Leu Ile Ala Phe Ile Gly Gly Ala Gln Ile Asp
            100                 105                 110 ccg tac ggc aac gtg aac tcc act tcc atc ggt gat tac cat cat ccg        384
Pro Tyr Gly Asn Val Asn Ser Thr Ser Ile Gly Asp Tyr His His Pro
        115                 120                 125 aaa acc cgt ttc acc ggg tcc ggc ggt gcc aac ggg att gcc acc tac        432
Lys Thr Arg Phe Thr Gly Ser Gly Gly Ala Asn Gly Ile Ala Thr Tyr
    130                 135                 140 tcc aac acc atc atc atg atg cag cat gaa aaa cgc aga ttc atg aac        480
Ser Asn Thr Ile Ile Met Met Gln His Glu Lys Arg Arg Phe Met Asn
145                 150                 155                 160 aaa atc gac tac gtg acc agc ccg ggc tgg atc gac ggc cct ggc gga        528
Lys Ile Asp Tyr Val Thr Ser Pro Gly Trp Ile Asp Gly Pro Gly Gly
                165                 170                 175 cgg gaa aga ctg ggt ctg ccc ggc gat gtg gga cct cag ctg gta gta        576
Arg Glu Arg Leu Gly Leu Pro Gly Asp Val Gly Pro Gln Leu Val Val
            180                 185                 190 acc gat aaa ggg atc ctg aaa ttc gac gaa aag acc aaa cgg atg tac        624
Thr Asp Lys Gly Ile Leu Lys Phe Asp Glu Lys Thr Lys Arg Met Tyr
        195                 200                 205 ctg gct gcc tac tat ccc act tct tct ccg gaa gat gta ctg gaa aac        672
Leu Ala Ala Tyr Tyr Pro Thr Ser Ser Pro Glu Asp Val Leu Glu Asn
    210                 215                 220 acc ggg ttc gac ctg gat gta tcc aag gct gtg gaa ctg gaa gct ccg        720
Thr Gly Phe Asp Leu Asp Val Ser Lys Ala Val Glu Leu Glu Ala Pro
225                 230                 235                 240 gat ccg gcc gtc atc aaa ctg atc cgt gaa gaa atc gat ccg ggg cag        768
Asp Pro Ala Val Ile Lys Leu Ile Arg Glu Glu Ile Asp Pro Gly Gln
                245                 250                 255 gcc ttt atc cag gtc ccc acg gaa gca aaa taa                            801
Ala Phe Ile Gln Val Pro Thr Glu Ala Lys
            260                 265

<210> SEQ ID NO 6
<211> LENGTH: 266
<212> TYPE: PRT
<213> ORGANISM: Acidaminococcus fermentans

<400> SEQUENCE: 6

Met Ala Asp Tyr Thr Asn Tyr Thr Asn Lys Glu Met Gln Ala Val Thr
1               5                   10                  15

Ile Ala Lys Gln Ile Lys Asn Gly Gln Val Val Thr Val Gly Thr Gly
                20                  25                  30

Leu Pro Leu Ile Gly Ala Ser Val Ala Lys Arg Val Tyr Ala Pro Asp
            35                  40                  45

Cys His Ile Ile Val Glu Ser Gly Leu Met Asp Cys Ser Pro Val Glu
    50                  55                  60

Val Pro Arg Ser Val Gly Asp Leu Arg Phe Met Ala His Cys Gly Cys
65                  70                  75                  80

Ile Trp Pro Asn Val Arg Phe Val Gly Phe Glu Ile Asn Glu Tyr Leu
                85                  90                  95

His Lys Ala Asn Arg Leu Ile Ala Phe Ile Gly Gly Ala Gln Ile Asp
            100                 105                 110

Pro Tyr Gly Asn Val Asn Ser Thr Ser Ile Gly Asp Tyr His His Pro
        115                 120                 125

Lys Thr Arg Phe Thr Gly Ser Gly Gly Ala Asn Gly Ile Ala Thr Tyr
    130                 135                 140
```

```
Ser Asn Thr Ile Ile Met Met Gln His Glu Lys Arg Arg Phe Met Asn
145                 150                 155                 160

Lys Ile Asp Tyr Val Thr Ser Pro Gly Trp Ile Asp Pro Gly Gly
                165                 170                 175

Arg Glu Arg Leu Gly Leu Pro Gly Asp Val Gly Pro Gln Leu Val Val
            180                 185                 190

Thr Asp Lys Gly Ile Leu Lys Phe Asp Glu Lys Thr Lys Arg Met Tyr
        195                 200                 205

Leu Ala Ala Tyr Tyr Pro Thr Ser Ser Pro Glu Asp Val Leu Glu Asn
        210                 215                 220

Thr Gly Phe Asp Leu Asp Val Ser Lys Ala Val Glu Leu Glu Ala Pro
225                 230                 235                 240

Asp Pro Ala Val Ile Lys Leu Ile Arg Glu Glu Ile Asp Pro Gly Gln
                245                 250                 255

Ala Phe Ile Gln Val Pro Thr Glu Ala Lys
            260                 265

<210> SEQ ID NO 7
<211> LENGTH: 1445
<212> TYPE: DNA
<213> ORGANISM: Clostridium symbiosum
<220> FEATURE:
<221> NAME/KEY: CDS
<222> LOCATION: (1)..(1443)

<400> SEQUENCE: 7
```

| | | | | | | | | | | | | | | | | |
|---|---|---|---|---|---|---|---|---|---|---|---|---|---|---|---|---|
| atg | gca | aaa | caa | gtt | agt | cct | ggc | gtt | ctc | gca | ctt | cgc | aag | gtc | gtt | 48 |
| Met | Ala | Lys | Gln | Val | Ser | Pro | Gly | Val | Leu | Ala | Leu | Arg | Lys | Val | Val | |
| 1 | | | | 5 | | | | | 10 | | | | | 15 | | |
| gat | gac | gta | cac | aaa | gag | gcg | cgc | gag | gcc | aaa | gca | aga | ggc | gag | tta | 96 |
| Asp | Asp | Val | His | Lys | Glu | Ala | Arg | Glu | Ala | Lys | Ala | Arg | Gly | Glu | Leu | |
| | | | 20 | | | | | 25 | | | | | 30 | | | |
| gtc | ggc | tgg | tcc | tca | tcc | aag | ttc | cct | tgt | gag | ctt | gca | gca | gct | ttt | 144 |
| Val | Gly | Trp | Ser | Ser | Ser | Lys | Phe | Pro | Cys | Glu | Leu | Ala | Ala | Ala | Phe | |
| | | | 35 | | | | | 40 | | | | | 45 | | | |
| gat | ctg | aat | gtt | atg | tat | ccg | gag | aac | cag | gct | gcc | ggc | atc | gct | gca | 192 |
| Asp | Leu | Asn | Val | Met | Tyr | Pro | Glu | Asn | Gln | Ala | Ala | Gly | Ile | Ala | Ala | |
| | 50 | | | | | 55 | | | | | 60 | | | | | |
| aac | cgt | tac | ggt | gag | atg | atg | tgc | cag | gcc | gct | gag | gat | ctt | ggc | tat | 240 |
| Asn | Arg | Tyr | Gly | Glu | Met | Met | Cys | Gln | Ala | Ala | Glu | Asp | Leu | Gly | Tyr | |
| 65 | | | | | 70 | | | | | 75 | | | | | 80 | |
| gac | aac | gat | atc | tgc | gga | tat | gcc | cgt | atc | agt | ctg | gct | tat | gca | gcc | 288 |
| Asp | Asn | Asp | Ile | Cys | Gly | Tyr | Ala | Arg | Ile | Ser | Leu | Ala | Tyr | Ala | Ala | |
| | | | | 85 | | | | | 90 | | | | | 95 | | |
| ggt | gtg | cgt | gta | tca | cgc | aaa | tat | gat | gct | gaa | acc | ggt | gaa | tac | atc | 336 |
| Gly | Val | Arg | Val | Ser | Arg | Lys | Tyr | Asp | Ala | Glu | Thr | Gly | Glu | Tyr | Ile | |
| | | | 100 | | | | | 105 | | | | | 110 | | | |
| atc | gat | cct | gct | aca | ggc | aaa | ccg | tta | aaa | gac | gca | gaa | ggc | aat | gtg | 384 |
| Ile | Asp | Pro | Ala | Thr | Gly | Lys | Pro | Leu | Lys | Asp | Ala | Glu | Gly | Asn | Val | |
| | | 115 | | | | | 120 | | | | | 125 | | | | |
| gta | atc | gac | gaa | gca | acc | ggt | aaa | cca | aag | aaa | gat | cca | aag | aca | cag | 432 |
| Val | Ile | Asp | Glu | Ala | Thr | Gly | Lys | Pro | Lys | Lys | Asp | Pro | Lys | Thr | Gln | |
| | | 130 | | | | | 135 | | | | | 140 | | | | |
| act | cct | tat | ctt | gta | ctg | gac | aat | ctg | ctt | gag | att | gaa | gct | ctt | ccg | 480 |
| Thr | Pro | Tyr | Leu | Val | Leu | Asp | Asn | Leu | Leu | Glu | Ile | Glu | Ala | Leu | Pro | |
| 145 | | | | | 150 | | | | | 155 | | | | | 160 | |
| gac | ggc | ccg | gag | aaa | gaa | aga | cgt | ctg | gag | gca | atc | tct | cca | atc | cgt | 528 |
| Asp | Gly | Pro | Glu | Lys | Glu | Arg | Arg | Leu | Glu | Ala | Ile | Ser | Pro | Ile | Arg | |
| | | | 165 | | | | | 170 | | | | | 175 | | | |

```
cag atg cgt att ccg cag ccg gac ttc gtt ctc tgc tgt aac aat atc      576
Gln Met Arg Ile Pro Gln Pro Asp Phe Val Leu Cys Cys Asn Asn Ile
        180                 185                 190 tgc aac tgt atg acc aaa tgg tat gag aat att gcc cgt atg tgc aac      624
Cys Asn Cys Met Thr Lys Trp Tyr Glu Asn Ile Ala Arg Met Cys Asn
            195                 200                 205 gta ccg ctg atc atg att gat att ccg tat aac aat aca gta gag gtt      672
Val Pro Leu Ile Met Ile Asp Ile Pro Tyr Asn Asn Thr Val Glu Val
    210                 215                 220 cat gac gat aat gta aaa tat gta cgc gct cag ttc gat aag gca att      720
His Asp Asp Asn Val Lys Tyr Val Arg Ala Gln Phe Asp Lys Ala Ile
225                 230                 235                 240 aag cag tta gaa gaa ctc aca ggc aag aaa ttt gac gag aag aag ttt      768
Lys Gln Leu Glu Glu Leu Thr Gly Lys Lys Phe Asp Glu Lys Lys Phe
                245                 250                 255 gaa aaa gcc tgt tcc aat gct aac cgt acc gca cag gca tgg tta aag      816
Glu Lys Ala Cys Ser Asn Ala Asn Arg Thr Ala Gln Ala Trp Leu Lys
            260                 265                 270 gtt tgc gat tat ctt cag tat aaa ccg gct cca tac agc ggt ttc gac      864
Val Cys Asp Tyr Leu Gln Tyr Lys Pro Ala Pro Tyr Ser Gly Phe Asp
        275                 280                 285 ctg ttc aac cat atg gct gac gtc gta act gca cgt gcc aga gtg gaa      912
Leu Phe Asn His Met Ala Asp Val Val Thr Ala Arg Ala Arg Val Glu
    290                 295                 300 gcc gct gag gca ttt gag ctt ctg gca gac gat ctg gaa gag aca gtt      960
Ala Ala Glu Ala Phe Glu Leu Leu Ala Asp Asp Leu Glu Glu Thr Val
305                 310                 315                 320 aag aag ggt gag acg aca act ccg ttc ccg gag aaa tac cgt gtt atg     1008
Lys Lys Gly Glu Thr Thr Thr Pro Phe Pro Glu Lys Tyr Arg Val Met
                325                 330                 335 ttc gag ggt att cct tgc tgg ccg aag ctg cct aac ctg ttc aaa cct     1056
Phe Glu Gly Ile Pro Cys Trp Pro Lys Leu Pro Asn Leu Phe Lys Pro
            340                 345                 350 ctg aaa gag cat ggc gtc aac gtt act gcc gtt gtt tat gca cca gct     1104
Leu Lys Glu His Gly Val Asn Val Thr Ala Val Val Tyr Ala Pro Ala
        355                 360                 365 ttc ggt ttt gtt tat aac aac atc gat gag atg gcc cgc gct tac tac     1152
Phe Gly Phe Val Tyr Asn Asn Ile Asp Glu Met Ala Arg Ala Tyr Tyr
    370                 375                 380 aaa gct ccg aac tcc gtc tgc atc gaa cag ggt gtt gac tgg cgt gaa     1200
Lys Ala Pro Asn Ser Val Cys Ile Glu Gln Gly Val Asp Trp Arg Glu
385                 390                 395                 400 ggt atc tgc cgc gac aat aag gta gat ggc gtt ctt gtt cat tat aac     1248
Gly Ile Cys Arg Asp Asn Lys Val Asp Gly Val Leu Val His Tyr Asn
                405                 410                 415 aga agc tgt aaa ccg tgg agc ggt tat atg gct gag atg cag cgg cgt     1296
Arg Ser Cys Lys Pro Trp Ser Gly Tyr Met Ala Glu Met Gln Arg Arg
            420                 425                 430 ttc act gaa gat ctg ggc gtt cca tgc gca ggt ttc gac ggt gac cag     1344
Phe Thr Glu Asp Leu Gly Val Pro Cys Ala Gly Phe Asp Gly Asp Gln
        435                 440                 445 gct gac ccg cgt aac ttc aat gcc gct cag tat gag acc cga gta cag     1392
Ala Asp Pro Arg Asn Phe Asn Ala Ala Gln Tyr Glu Thr Arg Val Gln
    450                 455                 460 ggc ctt gtg gag gca atg gaa gca aat aag cag gca aag gag gca aag     1440
Gly Leu Val Glu Ala Met Glu Ala Asn Lys Gln Ala Lys Glu Ala Lys
465                 470                 475                 480 taa ca                                                              1445
```

```
<210> SEQ ID NO 8
<211> LENGTH: 480
<212> TYPE: PRT
<213> ORGANISM: Clostridium symbiosum

<400> SEQUENCE: 8
```

Met Ala Lys Gln Val Ser Pro Gly Val Leu Ala Leu Arg Lys Val
1               5                   10                  15

Asp Asp Val His Lys Glu Ala Arg Glu Ala Lys Ala Arg Gly Glu Leu
            20                  25                  30

Val Gly Trp Ser Ser Ser Lys Phe Pro Cys Glu Leu Ala Ala Ala Phe
        35                  40                  45

Asp Leu Asn Val Met Tyr Pro Glu Asn Gln Ala Ala Gly Ile Ala Ala
50                  55                  60

Asn Arg Tyr Gly Glu Met Met Cys Gln Ala Ala Glu Asp Leu Gly Tyr
65              70                  75                  80

Asp Asn Asp Ile Cys Gly Tyr Ala Arg Ile Ser Leu Ala Tyr Ala Ala
                85                  90                  95

Gly Val Arg Val Ser Arg Lys Tyr Asp Ala Glu Thr Gly Glu Tyr Ile
            100                 105                 110

Ile Asp Pro Ala Thr Gly Lys Pro Leu Lys Asp Ala Glu Gly Asn Val
        115                 120                 125

Val Ile Asp Glu Ala Thr Gly Lys Pro Lys Lys Asp Pro Lys Thr Gln
130                 135                 140

Thr Pro Tyr Leu Val Leu Asp Asn Leu Leu Glu Ile Glu Ala Leu Pro
145                 150                 155                 160

Asp Gly Pro Glu Lys Glu Arg Arg Leu Glu Ala Ile Ser Pro Ile Arg
                165                 170                 175

Gln Met Arg Ile Pro Gln Pro Asp Phe Val Leu Cys Cys Asn Asn Ile
            180                 185                 190

Cys Asn Cys Met Thr Lys Trp Tyr Glu Asn Ile Ala Arg Met Cys Asn
        195                 200                 205

Val Pro Leu Ile Met Ile Asp Ile Pro Tyr Asn Asn Thr Val Glu Val
210                 215                 220

His Asp Asp Asn Val Lys Tyr Val Arg Ala Gln Phe Asp Lys Ala Ile
225                 230                 235                 240

Lys Gln Leu Glu Glu Leu Thr Gly Lys Lys Phe Asp Glu Lys Lys Phe
                245                 250                 255

Glu Lys Ala Cys Ser Asn Ala Asn Arg Thr Ala Gln Ala Trp Leu Lys
            260                 265                 270

Val Cys Asp Tyr Leu Gln Tyr Lys Pro Ala Pro Tyr Ser Gly Phe Asp
        275                 280                 285

Leu Phe Asn His Met Ala Asp Val Val Thr Ala Arg Ala Arg Val Glu
290                 295                 300

Ala Ala Glu Ala Phe Glu Leu Leu Ala Asp Asp Leu Glu Glu Thr Val
305                 310                 315                 320

Lys Lys Gly Glu Thr Thr Thr Pro Phe Pro Glu Lys Tyr Arg Val Met
                325                 330                 335

Phe Glu Gly Ile Pro Cys Trp Pro Lys Leu Pro Asn Leu Phe Lys Pro
            340                 345                 350

Leu Lys Glu His Gly Val Asn Val Thr Ala Val Val Tyr Ala Pro Ala
        355                 360                 365

Phe Gly Phe Val Tyr Asn Asn Ile Asp Glu Met Ala Arg Ala Tyr Tyr
370                 375                 380

-continued

| Lys | Ala | Pro | Asn | Ser | Val | Cys | Ile | Glu | Gln | Gly | Val | Asp | Trp | Arg | Glu |
|---|---|---|---|---|---|---|---|---|---|---|---|---|---|---|---|
| 385 | | | | 390 | | | | | 395 | | | | | 400 | |

| Gly | Ile | Cys | Arg | Asp | Asn | Lys | Val | Asp | Gly | Val | Leu | Val | His | Tyr | Asn |
|---|---|---|---|---|---|---|---|---|---|---|---|---|---|---|---|
| | | | 405 | | | | | 410 | | | | | 415 | | |

| Arg | Ser | Cys | Lys | Pro | Trp | Ser | Gly | Tyr | Met | Ala | Glu | Met | Gln | Arg | Arg |
|---|---|---|---|---|---|---|---|---|---|---|---|---|---|---|---|
| | | | 420 | | | | | 425 | | | | | 430 | | |

| Phe | Thr | Glu | Asp | Leu | Gly | Val | Pro | Cys | Ala | Gly | Phe | Asp | Gly | Asp | Gln |
|---|---|---|---|---|---|---|---|---|---|---|---|---|---|---|---|
| | | | 435 | | | | | 440 | | | | | 445 | | |

| Ala | Asp | Pro | Arg | Asn | Phe | Asn | Ala | Ala | Gln | Tyr | Glu | Thr | Arg | Val | Gln |
|---|---|---|---|---|---|---|---|---|---|---|---|---|---|---|---|
| | | 450 | | | | | 455 | | | | | 460 | | | |

| Gly | Leu | Val | Glu | Ala | Met | Glu | Ala | Asn | Lys | Gln | Ala | Lys | Glu | Ala | Lys |
|---|---|---|---|---|---|---|---|---|---|---|---|---|---|---|---|
| 465 | | | | | 470 | | | | | 475 | | | | | 480 |

<210> SEQ ID NO 9
<211> LENGTH: 1152
<212> TYPE: DNA
<213> ORGANISM: Clostridium symbiosum
<220> FEATURE:
<221> NAME/KEY: CDS
<222> LOCATION: (1)..(1152)

<400> SEQUENCE: 9

```
atg agt atc aac gca tta ttg gat gaa ttt aaa gta aag gct gcc act      48
Met Ser Ile Asn Ala Leu Leu Asp Glu Phe Lys Val Lys Ala Ala Thr
1               5                   10                  15 cca aaa cag cag ctt gct gaa tat aaa gct cag ggc aag aaa gta atc      96
Pro Lys Gln Gln Leu Ala Glu Tyr Lys Ala Gln Gly Lys Lys Val Ile
            20                  25                  30 ggt gtt ctg ccg tat tac gca ccg gaa gag ctt gtt tat gcc gca ggt     144
Gly Val Leu Pro Tyr Tyr Ala Pro Glu Glu Leu Val Tyr Ala Ala Gly
        35                  40                  45 atg gtg ccg atg gga atc tgg ggt tcc aat aac aag act atc agc cgt     192
Met Val Pro Met Gly Ile Trp Gly Ser Asn Asn Lys Thr Ile Ser Arg
    50                  55                  60 gct aaa gaa tac tgt gca act ttc tac tgc act atc gca cag ctt gct     240
Ala Lys Glu Tyr Cys Ala Thr Phe Tyr Cys Thr Ile Ala Gln Leu Ala
65                  70                  75                  80 ctg gag atg ctg tta gac ggc aca atg gat cag ctg gac gga atc att     288
Leu Glu Met Leu Leu Asp Gly Thr Met Asp Gln Leu Asp Gly Ile Ile
                85                  90                  95 act cca acc atc tgt gat aca ctg cgc cca atg agc cag aac ttc cgt     336
Thr Pro Thr Ile Cys Asp Thr Leu Arg Pro Met Ser Gln Asn Phe Arg
            100                 105                 110 gtt gct atg gga gat aag atg gca gtt atc ttc ctt gct cag cct cag     384
Val Ala Met Gly Asp Lys Met Ala Val Ile Phe Leu Ala Gln Pro Gln
        115                 120                 125 aac cgt ttt gaa gat ttc ggt ctt cag ttc agt gtt gac cag tat aca     432
Asn Arg Phe Glu Asp Phe Gly Leu Gln Phe Ser Val Asp Gln Tyr Thr
    130                 135                 140 aat gtt aag aaa gaa ctg gaa aaa gtt gcc ggt aaa gag att acc aac     480
Asn Val Lys Lys Glu Leu Glu Lys Val Ala Gly Lys Glu Ile Thr Asn
145                 150                 155                 160 gag gcg att cag gat gcc atc aaa gta tac aat aag agc cgt gcg gcc     528
Glu Ala Ile Gln Asp Ala Ile Lys Val Tyr Asn Lys Ser Arg Ala Ala
                165                 170                 175 cgc cgt aaa ttc gta gaa ctg gca agc gca cac tgc gat gtc att aca     576
Arg Arg Lys Phe Val Glu Leu Ala Ser Ala His Cys Asp Val Ile Thr
            180                 185                 190 cca acc aag cgt tct gca gta ctg aaa tcc ttc ttc ttt atg gag aaa     624
Pro Thr Lys Arg Ser Ala Val Leu Lys Ser Phe Phe Phe Met Glu Lys
```

```
                  195                 200                 205
ccg gaa tac ata gag aag ctg gaa gaa ttg aac gca gag ctt gaa aaa      672
Pro Glu Tyr Ile Glu Lys Leu Glu Glu Leu Asn Ala Glu Leu Glu Lys
    210                 215                 220 ctt cct gtc tgt gac tgg cag gga acc aag gtt gtt aca tcc ggt att      720
Leu Pro Val Cys Asp Trp Gln Gly Thr Lys Val Val Thr Ser Gly Ile
225                 230                 235                 240 atc tgt gac aat cca aag ctt ctt gaa atc ttc gaa gag aac aac att      768
Ile Cys Asp Asn Pro Lys Leu Leu Glu Ile Phe Glu Glu Asn Asn Ile
                245                 250                 255 gcc atc gcc gca gac gac gtt ggc cat gag agc cgt tcc ttc cgt gta      816
Ala Ile Ala Ala Asp Asp Val Gly His Glu Ser Arg Ser Phe Arg Val
            260                 265                 270 gac gct ccg gag gat gag gca gat gca tta atg gca ctg gca aaa cag      864
Asp Ala Pro Glu Asp Glu Ala Asp Ala Leu Met Ala Leu Ala Lys Gln
        275                 280                 285 ttt gcc aat atg gac tat gac gtt ctt ctg tac gat cca aaa tct aca      912
Phe Ala Asn Met Asp Tyr Asp Val Leu Leu Tyr Asp Pro Lys Ser Thr
    290                 295                 300 gag aac cgc cgc ggc gaa ttc att gcc aac atg gta aag gaa agc ggc      960
Glu Asn Arg Arg Gly Glu Phe Ile Ala Asn Met Val Lys Glu Ser Gly
305                 310                 315                 320 gct cag gga ctg gta ttg ttc atg caa cag ttc tgt gac ccg gag gaa     1008
Ala Gln Gly Leu Val Leu Phe Met Gln Gln Phe Cys Asp Pro Glu Glu
                325                 330                 335 atg gag tat cca tac tta aag aag gca tta aat aat gca ggt att ccg     1056
Met Glu Tyr Pro Tyr Leu Lys Lys Ala Leu Asn Asn Ala Gly Ile Pro
            340                 345                 350 cat atc aaa ctg ggt atc gat cag cag atg cgt gac ttc ggt cag gca     1104
His Ile Lys Leu Gly Ile Asp Gln Gln Met Arg Asp Phe Gly Gln Ala
        355                 360                 365 agc aca gct atc cag gca ttt gca gat gta ctc gag atg cag aaa taa     1152
Ser Thr Ala Ile Gln Ala Phe Ala Asp Val Leu Glu Met Gln Lys
    370                 375                 380

<210> SEQ ID NO 10
<211> LENGTH: 383
<212> TYPE: PRT
<213> ORGANISM: Clostridium symbiosum

<400> SEQUENCE: 10

Met Ser Ile Asn Ala Leu Leu Asp Glu Phe Lys Val Lys Ala Ala Thr
1               5                   10                  15

Pro Lys Gln Gln Leu Ala Glu Tyr Lys Ala Gln Gly Lys Lys Val Ile
            20                  25                  30

Gly Val Leu Pro Tyr Tyr Ala Pro Glu Glu Leu Val Tyr Ala Ala Gly
        35                  40                  45

Met Val Pro Met Gly Ile Trp Gly Ser Asn Asn Lys Thr Ile Ser Arg
    50                  55                  60

Ala Lys Glu Tyr Cys Ala Thr Phe Tyr Cys Thr Ile Ala Gln Leu Ala
65                  70                  75                  80

Leu Glu Met Leu Leu Asp Gly Thr Met Asp Gln Leu Asp Gly Ile Ile
                85                  90                  95

Thr Pro Thr Ile Cys Asp Thr Leu Arg Pro Met Ser Gln Asn Phe Arg
            100                 105                 110

Val Ala Met Gly Asp Lys Met Ala Val Ile Phe Leu Ala Gln Pro Gln
        115                 120                 125

Asn Arg Phe Glu Asp Phe Gly Leu Gln Phe Ser Val Asp Gln Tyr Thr
```

```
                130                 135                 140
Asn Val Lys Lys Glu Leu Glu Lys Val Ala Gly Lys Glu Ile Thr Asn
145                 150                 155                 160

Glu Ala Ile Gln Asp Ala Ile Lys Val Tyr Asn Lys Ser Arg Ala Ala
                165                 170                 175

Arg Arg Lys Phe Val Glu Leu Ala Ser Ala His Cys Asp Val Ile Thr
            180                 185                 190

Pro Thr Lys Arg Ser Ala Val Leu Lys Ser Phe Phe Met Glu Lys
        195                 200                 205

Pro Glu Tyr Ile Glu Lys Leu Glu Glu Leu Asn Ala Glu Leu Glu Lys
    210                 215                 220

Leu Pro Val Cys Asp Trp Gln Gly Thr Lys Val Val Thr Ser Gly Ile
225                 230                 235                 240

Ile Cys Asp Asn Pro Lys Leu Leu Glu Ile Phe Glu Glu Asn Asn Ile
                245                 250                 255

Ala Ile Ala Ala Asp Asp Val Gly His Glu Ser Arg Ser Phe Arg Val
                260                 265                 270

Asp Ala Pro Glu Asp Glu Ala Asp Ala Leu Met Ala Leu Ala Lys Gln
            275                 280                 285

Phe Ala Asn Met Asp Tyr Asp Val Leu Leu Tyr Asp Pro Lys Ser Thr
        290                 295                 300

Glu Asn Arg Arg Gly Glu Phe Ile Ala Asn Met Val Lys Glu Ser Gly
305                 310                 315                 320

Ala Gln Gly Leu Val Leu Phe Met Gln Gln Phe Cys Asp Pro Glu Glu
                325                 330                 335

Met Glu Tyr Pro Tyr Leu Lys Lys Ala Leu Asn Asn Ala Gly Ile Pro
                340                 345                 350

His Ile Lys Leu Gly Ile Asp Gln Gln Met Arg Asp Phe Gly Gln Ala
            355                 360                 365

Ser Thr Ala Ile Gln Ala Phe Ala Asp Val Leu Glu Met Gln Lys
        370                 375                 380

<210> SEQ ID NO 11
<211> LENGTH: 783
<212> TYPE: DNA
<213> ORGANISM: Acidaminococcus fermentans
<220> FEATURE:
<221> NAME/KEY: CDS
<222> LOCATION: (1)..(783)

<400> SEQUENCE: 11 atg agt atc tat acc ttg gga atc gat gtt gga tct act gca tcc aag        48
Met Ser Ile Tyr Thr Leu Gly Ile Asp Val Gly Ser Thr Ala Ser Lys
1               5                   10                  15 tgc att atc ctg aaa gat gga aaa gaa atc gtg gcg aaa tcc ctg gta        96
Cys Ile Ile Leu Lys Asp Gly Lys Glu Ile Val Ala Lys Ser Leu Val
                20                  25                  30 gcc gtg ggg acc gga act tcc ggt ccc gca cgg tct att tcg gaa gtc       144
Ala Val Gly Thr Gly Thr Ser Gly Pro Ala Arg Ser Ile Ser Glu Val
            35                  40                  45 ctg gaa aat gcc cac atg aaa aaa gaa gac atg gcc ttt acc ctg gct       192
Leu Glu Asn Ala His Met Lys Lys Glu Asp Met Ala Phe Thr Leu Ala
        50                  55                  60 acc ggc tac gga cgc aat tcg ctg gaa ggc att gcc gac aag cag atg       240
Thr Gly Tyr Gly Arg Asn Ser Leu Glu Gly Ile Ala Asp Lys Gln Met
65                  70                  75                  80 agc gaa ctg agc tgc cat gcc atg ggc gcc agc ttt atc tgg ccc aac       288
```

```
Ser Glu Leu Ser Cys His Ala Met Gly Ala Ser Phe Ile Trp Pro Asn
             85                  90                  95 gtc cat acc gtc atc gat atc ggc ggg cag gat gtg aag gtc atc cat      336
Val His Thr Val Ile Asp Ile Gly Gly Gln Asp Val Lys Val Ile His
            100                 105                 110 gtg gaa aac ggg acc atg acc aat ttc cag atg aat gat aaa tgc gct      384
Val Glu Asn Gly Thr Met Thr Asn Phe Gln Met Asn Asp Lys Cys Ala
        115                 120                 125 gcc ggg act ggc cgt ttc ctg gat gtt atg gcc aat atc ctg gaa gtg      432
Ala Gly Thr Gly Arg Phe Leu Asp Val Met Ala Asn Ile Leu Glu Val
130                 135                 140 aag gtt tcc gac ctg gct gag ctg gga gcc aaa tcc acc aaa cgg gtg      480
Lys Val Ser Asp Leu Ala Glu Leu Gly Ala Lys Ser Thr Lys Arg Val
145                 150                 155                 160 gct atc agc tcc acc tgt act gtg ttt gca gaa agt gaa gtc atc agc      528
Ala Ile Ser Ser Thr Cys Thr Val Phe Ala Glu Ser Glu Val Ile Ser
                165                 170                 175 cag ctg tcc aaa gga acc gac aag atc gac atc att gcc ggg atc cat      576
Gln Leu Ser Lys Gly Thr Asp Lys Ile Asp Ile Ile Ala Gly Ile His
            180                 185                 190 cgt tct gta gcc agc cgg gtc att ggt ctt gcc aat cgg gtg ggg att      624
Arg Ser Val Ala Ser Arg Val Ile Gly Leu Ala Asn Arg Val Gly Ile
        195                 200                 205 gtg aaa gac gtg gtc atg acc ggc ggt gta gcc cag aac tat ggc gtg      672
Val Lys Asp Val Val Met Thr Gly Gly Val Ala Gln Asn Tyr Gly Val
210                 215                 220 aga gga gcc ctg gaa gaa ggc ctt ggc gtg gaa atc aag acg tct ccc      720
Arg Gly Ala Leu Glu Glu Gly Leu Gly Val Glu Ile Lys Thr Ser Pro
225                 230                 235                 240 ctg gct cag tac aac ggt gcc ctg ggt gcc gct ctg tat gcg tat aaa      768
Leu Ala Gln Tyr Asn Gly Ala Leu Gly Ala Ala Leu Tyr Ala Tyr Lys
                245                 250                 255 aaa gca gcc aaa taa                                                  783
Lys Ala Ala Lys
        260

<210> SEQ ID NO 12
<211> LENGTH: 260
<212> TYPE: PRT
<213> ORGANISM: Acidaminococcus fermentans

<400> SEQUENCE: 12

Met Ser Ile Tyr Thr Leu Gly Ile Asp Val Gly Ser Thr Ala Ser Lys
1               5                   10                  15

Cys Ile Ile Leu Lys Asp Gly Lys Glu Ile Val Ala Lys Ser Leu Val
            20                  25                  30

Ala Val Gly Thr Gly Thr Ser Gly Pro Ala Arg Ser Ile Ser Glu Val
        35                  40                  45

Leu Glu Asn Ala His Met Lys Lys Glu Asp Met Ala Phe Thr Leu Ala
    50                  55                  60

Thr Gly Tyr Gly Arg Asn Ser Leu Glu Gly Ile Ala Asp Lys Gln Met
65                  70                  75                  80

Ser Glu Leu Ser Cys His Ala Met Gly Ala Ser Phe Ile Trp Pro Asn
                85                  90                  95

Val His Thr Val Ile Asp Ile Gly Gly Gln Asp Val Lys Val Ile His
            100                 105                 110

Val Glu Asn Gly Thr Met Thr Asn Phe Gln Met Asn Asp Lys Cys Ala
        115                 120                 125
```

```
Ala Gly Thr Gly Arg Phe Leu Asp Val Met Ala Asn Ile Leu Glu Val
        130                 135                 140

Lys Val Ser Asp Leu Ala Glu Leu Gly Ala Lys Ser Thr Lys Arg Val
145                 150                 155                 160

Ala Ile Ser Ser Thr Cys Thr Val Phe Ala Glu Ser Glu Val Ile Ser
                165                 170                 175

Gln Leu Ser Lys Gly Thr Asp Lys Ile Asp Ile Ala Gly Ile His
            180                 185                 190

Arg Ser Val Ala Ser Arg Val Ile Gly Leu Ala Asn Arg Val Gly Ile
            195                 200                 205

Val Lys Asp Val Val Met Thr Gly Gly Val Ala Gln Asn Tyr Gly Val
210                 215                 220

Arg Gly Ala Leu Glu Glu Gly Leu Gly Val Glu Ile Lys Thr Ser Pro
225                 230                 235                 240

Leu Ala Gln Tyr Asn Gly Ala Leu Gly Ala Ala Leu Tyr Ala Tyr Lys
                245                 250                 255

Lys Ala Ala Lys
            260

<210> SEQ ID NO 13
<211> LENGTH: 4008
<212> TYPE: DNA
<213> ORGANISM: Artificial
<220> FEATURE:
<223> OTHER INFORMATION: plasmid

<400> SEQUENCE: 13
ggggaattgt gagcggataa caattcccct gtagaaataa ttttgtttaa ctttaataag     60
gagatatacc atgggcagca gccatcacca tcatcaccac agccaggatc cgaattcgag    120
ctcggcgcgc ctgcaggtcg acaagcttgc ggccgcataa tgcttaagtc gaacagaaag    180
taatcgtatt gtacacggcc gcataatcga attaatacg actcactata ggggaattgt     240
gagcggataa caattcccca tcttagtata ttagttaagt ataagaagga gatatacata    300
tggcagatct caattggata tcggccggcc acgcgatcgc tgacgtcggt accctcgagt    360
ctggtaaaga aaccgctgct gcgaaatttg aacgccagca catggactcg tctactagcg    420
cagcttaatt aacctaggct gctgccaccg ctgagcaata actagcataa ccccttgggg    480
cctctaaacg ggtcttgagg ggttttttgc tgaaacctca ggcatttgag aagcacacgg    540
tcacactgct tccggtagtc aataaaccgg taaaccagca atagacataa gcggctattt    600
aacgaccctg ccctgaaccg acgaccgggt cgaatttgct ttcgaatttc tgccattcat    660
ccgcttatta tcacttattc aggcgtagca ccaggcgttt aagggcacca ataactgcct    720
taaaaaaatt acgccccgcc ctgccactca tcgcagtact gttgtaattc attaagcatt    780
ctgccgacat ggaagccatc acagacggca tgatgaacct gaatcgccag cggcatcagc    840
accttgtcgc cttgcgtata atatttgccc atagtgaaaa cgggggcgaa gaagttgtcc    900
atattggcca cgtttaaatc aaaactggtg aaactcaccc agggattggc tgagacgaaa    960
aacatattct caataaaccc tttagggaaa taggccaggt tttcaccgta acacgccaca   1020
tcttgcgaat atatgtgtag aaactgccgg aaatcgtcgt ggtattcact ccagagcgat   1080
gaaaacgttt cagtttgctc atggaaaacg gtgtaacaag ggtgaacact atcccatatc   1140
accagctcac cgtctttcat tgccatacgg aactccggat gagcattcat caggcgggca   1200
agaatgtgaa taaaggccgg ataaaacttg tgcttatttt tctttacggt ctttaaaaag   1260
```

```
gccgtaatat ccagctgaac ggtctggtta taggtacatt gagcaactga ctgaaatgcc    1320
tcaaaatgtt ctttacgatg ccattgggat atatcaacgg tggtatatcc agtgattttt    1380
ttctccattt tagcttcctt agctcctgaa aatctcgata actcaaaaaa tacgcccggt    1440
agtgatctta tttcattatg gtgaaagttg gaacctctta cgtgccgatc aacgtctcat    1500
tttcgccaaa agttggccca gggcttcccg gtatcaacag ggacaccagg atttatttat    1560
tctgcgaagt gatcttccgt cacaggtatt tattcggcgc aaagtgcgtc gggtgatgct    1620
gccaacttac tgatttagtg tatgatggtg tttttgaggt gctccagtgg cttctgtttc    1680
tatcagctgt ccctcctgtt cagctactga cggggtggtg cgtaacggca aaagcaccgc    1740
cggacatcag cgctagcgga gtgtatactg gcttactatg ttggcactga tgagggtgtc    1800
agtgaagtgc ttcatgtggc aggagaaaaa aggctgcacc ggtgcgtcag cagaatatgt    1860
gatacaggat atattccgct tcctcgctca ctgactcgct acgctcggtc gttcgactgc    1920
ggcgagcgga aatggcttac gaacggggcg gagatttcct ggaagatgcc aggaagatac    1980
ttaacaggga agtgagaggg ccgcggcaaa gccgttttc cataggctcc gcccccctga    2040
caagcatcac gaaatctgac gctcaaatca gtggtggcga aacccgacag gactataaag    2100
ataccaggcg tttcccctgg cggctccctc gtgcgctctc ctgttcctgc ctttcggttt    2160
accggtgtca ttccgctgtt atggccgcgt ttgtctcatt ccacgcctga cactcagttc    2220
cgggtaggca gttcgctcca agctggactg tatgcacgaa ccccccgttc agtccgaccg    2280
ctgcgcctta tccggtaact atcgtcttga gtccaacccg gaaagacatg caaaagcacc    2340
actggcagca gccactggta attgatttag aggagttagt cttgaagtca tgcgccggtt    2400
aaggctaaac tgaaaggaca agttttggtg actgcgctcc tccaagccag ttacctcggt    2460
tcaaagagtt ggtagctcag agaaccttcg aaaaaccgcc ctgcaaggcg gttttttcgt    2520
tttcagagca agagattacg cgcagaccaa aacgatctca agaagatcat cttattaatc    2580
agataaaata tttctagatt tcagtgcaat ttatctcttc aaatgtagca cctgaagtca    2640
gccccatacg atataagttg taattctcat gttagtcatg ccccgcgccc accggaagga    2700
gctgactggg ttgaaggctc tcaagggcat cggtcgagat cccggtgcct aatgagtgag    2760
ctaacttaca ttaattgcgt tgcgctcact gcccgctttc cagtcgggaa acctgtcgtg    2820
ccagctgcat taatgaatcg gccaacgcgc ggggagaggc ggtttgcgta ttgggcgcca    2880
gggtggtttt tcttttcacc agtgagacgg gcaacagctg attgcccttc accgcctggc    2940
cctgagagag ttgcagcaag cggtccacgc tggtttgccc cagcaggcga aaatcctgtt    3000
tgatggtggt taacggcggg atataacatg agctgtcttc ggtatcgtcg tatcccacta    3060
ccgagatgtc cgcaccaacg cgcagcccgg actcggtaat ggcgcgcatt gcgcccagcg    3120
ccatctgatc gttggcaacc agcatcgcag tgggaacgat gccctcattc agcatttgca    3180
tggtttgttg aaaaccggac atggcactcc agtcgccttc ccgttccgct atcggctgaa    3240
tttgattgcg agtgagatat ttatgccagc cagccagacg cagacgcgcc gagacagaac    3300
ttaatgggcc cgctaacagc gcgatttgct ggtgacccaa tgcgaccaga tgctccacgc    3360
ccagtcgcgt accgtcttca tgggagaaaa taatactgtt gatgggtgtc tggtcagaga    3420
catcaagaaa taacgccgga acattagtgc aggcagcttc cacagcaatg gcatcctggt    3480
catccagcgg atagttaatg atcagcccac tgacgcgttg cgcgagaaga ttgtgcaccg    3540
ccgctttaca ggcttcgacg ccgcttcgtt ctaccatcga caccaccacg ctggcaccca    3600
gttgatcggc gcgagattta atcgccgcga caatttgcga cggcgcgtgc agggccagac    3660
```

```
tggaggtggc aacgccaatc agcaacgact gtttgcccgc cagttgttgt gccacgcggt    3720
tgggaatgta attcagctcc gccatcgccg cttccacttt ttcccgcgtt ttcgcagaaa    3780
cgtggctggc ctggttcacc acgcgggaaa cggtctgata agagacaccg gcatactctg    3840
cgacatcgta taacgttact ggtttcacat tcaccaccct gaattgactc tcttccgggc    3900
gctatcatgc cataccgcga aaggttttgc gccattcgat ggtgtccggg atctcgacgc    3960
tctcccttat gcgactcctg cattaggaaa ttaatacgac tcactata                 4008

<210> SEQ ID NO 14
<211> LENGTH: 3247
<212> TYPE: DNA
<213> ORGANISM: Artificial
<220> FEATURE:
<223> OTHER INFORMATION: plasmid

<400> SEQUENCE: 14
ccatcgaatg gccagatgat taattcctaa ttttttgttga cactctatca ttgatagagt      60
tattttacca ctccctatca gtgatagaga aaagtgaaat gaatagttcg acaaaaatct     120
agaaataatt ttgtttaact ttaagaagga gatatacaaa tgggagaccg cggtcccgaa     180
ttcgagctcg gtacccgggg atccctcgag gtcgacctgc aggggaccca tggtctcagc     240
gcttggagcc acccgcagtt cgaaaaataa taagcttgac ctgtgaagtg aaaaatggcg     300
cacattgtgc gacatttttt tgtctgccg tttaccgcta ctgcgtcacg gatctccacg      360
cgccctgtag cggcgcatta agcgcggcgg gtgtggtggt tacgcgcagc gtgaccgcta     420
cacttgccag cgccctagcg cccgctcctt tcgctttctt cccttccttt ctcgccacgt     480
tcgccggctt tccccgtcaa gctctaaatc gggggctccc tttagggttc cgatttagtg     540
ctttacggca cctcgacccc aaaaaacttg attagggtga tggttcacgt agtgggccat     600
cgccctgata gacggttttt cgccctttga cgttggagtc cacgttcttt aatagtggac     660
tcttgttcca aactggaaca cactcaacc ctatctcggt ctattctttt gatttataag      720
ggattttgcc gatttcggcc tattggttaa aaaatgagct gatttaacaa aaatttaacg     780
cgaattttaa caaaatatta acgcttacaa tttcaggtgg cacttttcgg ggaaatgtgc     840
gcggaacccc tatttgttta ttttttctaaa tacattcaaa tatgtatccg ctcatgagac     900
aataaccctg ataaatgctt caataatatt gaaaaggaa gagtatgagt attcaacatt      960
tccgtgtcgc ccttattccc ttttttgcgg cattttgcct tcctgttttt gctcacccag    1020
aaacgctggt gaaagtaaaa gatgctgaag atcagttggg tgcacgagtg ggttacatcg    1080
aactggatct caacagcggt aagatccttg agagttttcg ccccgaagaa cgttttccaa    1140
tgatgagcac ttttaaagtt ctgctatgtg gcgcggtatt atcccgtatt gacgccgggc    1200
aagagcaact cggtcgccgc atacactatt ctcagaatga cttggttgag tactcaccag    1260
tcacagaaaa gcatcttacg gatggcatga cagtaagaga attatgcagt gctgccataa    1320
ccatgagtga taacactgcg gccaacttac ttctgacaac gatcggagga ccgaaggagc    1380
taaccgcttt tttgcacaac atgggggatc atgtaactcg ccttgatcgt tgggaaccgg    1440
agctgaatga agccatacca aacgacgagc gtgacaccac gatgcctgta gcaatggcaa    1500
caacgttgcg caaactatta actggcgaac tacttactct agcttcccgg caacaattga    1560
tagactggat ggaggcggat aaagttgcag gaccacttct gcgctcggcc cttccggctg    1620
gctggtttat tgctgataaa tctggagccg gtgagcgtgg ctctcgcggt atcattgcag    1680
```

```
cactggggcc agatggtaag ccctcccgta tcgtagttat ctacacgacg gggagtcagg      1740
caactatgga tgaacgaaat agacagatcg ctgagatagg tgcctcactg attaagcatt      1800
ggtaggaatt aatgatgtct cgtttagata aaagtaaagt gattaacagc gcattagagc      1860
tgcttaatga ggtcggaatc gaaggtttaa caacccgtaa actcgcccag aagctaggtg      1920
tagagcagcc tacattgtat tggcatgtaa aaaataagcg ggctttgctc gacgccttag      1980
ccattgagat gttagatagg caccatactc acttttgccc tttagaaggg gaaagctggc      2040
aagatttttt acgtaataac gctaaaagtt ttagatgtgc tttactaagt catcgcgatg      2100
gagcaaaagt acatttaggt acacggccta cagaaaaaca gtatgaaact ctcgaaaatc      2160
aattagcctt tttatgccaa caaggttttt cactagagaa tgcattatat gcactcagcg      2220
cagtggggca ttttacttta ggttgcgtat tggaagatca agagcatcaa gtcgctaaag      2280
aagaaaggga aacacctact actgatagta tgccgccatt attacgacaa gctatcgaat      2340
tatttgatca ccaaggtgca gagccagcct tcttattcgg ccttgaattg atcatatgcg      2400
gattagaaaa acaacttaaa tgtgaaagtg ggtcttaaaa gcagcataac ctttttccgt      2460
gatggtaact tcactagttt aaaaggatct aggtgaagat ccttttttgat aatctcatga      2520 ccaaaatccc ttaacgtgag ttttcgttcc actgagcgtc agaccccgta gaaaagatca      2580
aaggatcttc ttgagatcct ttttttctgc gcgtaatctg ctgcttgcaa acaaaaaaac      2640
caccgctacc agcggtggtt tgtttgccgg atcaagagct accaactctt tttccgaagg      2700
taactggctt cagcagagcg cagataccaa atactgtcct tctagtgtag ccgtagttag      2760
gccaccactt caagaactct gtagcaccgc ctacatacct cgctctgcta atcctgttac      2820
cagtggctgc tgccagtggc gataagtcgt gtcttaccgg gttggactca agacgatagt      2880
taccggataa ggcgcagcgg tcgggctgaa cggggggttc gtgcacacag cccagcttgg      2940
agcgaacgac ctacaccgaa ctgagatacc tacagcgtga gctatgagaa agcgccacgc      3000
ttcccgaagg gagaaaggcg acaggtatc cggtaagcgg cagggtcgga acaggagagc      3060
gcacgaggga gcttccaggg ggaaacgcct ggtatcttta tagtcctgtc gggtttcgcc      3120
acctctgact tgagcgtcga ttttgtgat gctcgtcagg ggggcggagc ctatggaaaa      3180
acgccagcaa cgcggccttt ttacggttcc tggcctttg ctggccttttt gctcacatga      3240 cccgaca                                                                3247
```

<210> SEQ ID NO 15
<211> LENGTH: 1017
<212> TYPE: DNA
<213> ORGANISM: Fusobacterium nucleatum
<220> FEATURE:
<221> NAME/KEY: CDS
<222> LOCATION: (1)..(1017)

<400> SEQUENCE: 15

```
atg aaa gtt tta ttt tat ggt gta aga gaa gtt gaa ata cct tta ttt      48
Met Lys Val Leu Phe Tyr Gly Val Arg Glu Val Glu Ile Pro Leu Phe
1               5                   10                  15 cat gag cta aat aaa aag gaa gga ttt ggc tat gaa tta gaa tta att      96
His Glu Leu Asn Lys Lys Glu Gly Phe Gly Tyr Glu Leu Glu Leu Ile
            20                  25                  30 cct gat tat ctt aat agt aaa gaa act gca gaa aaa gca aaa gga ttt     144
Pro Asp Tyr Leu Asn Ser Lys Glu Thr Ala Glu Lys Ala Lys Gly Phe
        35                  40                  45 gaa tgt gtt gtt ctt cgt gga aac tgt ttt gca aca aaa gaa gtt tta     192
Glu Cys Val Val Leu Arg Gly Asn Cys Phe Ala Thr Lys Glu Val Leu
```

```
                  50                  55                  60
gat atg tat aaa gaa tat gga gta aaa tat cta ctt act aga aca gtt          240
Asp Met Tyr Lys Glu Tyr Gly Val Lys Tyr Leu Leu Thr Arg Thr Val
 65                  70                  75                  80 gga act aac cat att gat gta aaa tat gct aaa gaa tta gga ttt aaa          288
Gly Thr Asn His Ile Asp Val Lys Tyr Ala Lys Glu Leu Gly Phe Lys
                 85                  90                  95 tta gct tat gtt cct ttc tat tct cca aat gca ata gct gaa tta gct          336
Leu Ala Tyr Val Pro Phe Tyr Ser Pro Asn Ala Ile Ala Glu Leu Ala
            100                 105                 110 gtt tca cta gct atg tct tta cta aga cat tta cct tat aca gct gaa          384
Val Ser Leu Ala Met Ser Leu Leu Arg His Leu Pro Tyr Thr Ala Glu
        115                 120                 125 aaa ttt aaa aat aga aac ttt act gtt gac gct caa atg ttt tca aaa          432
Lys Phe Lys Asn Arg Asn Phe Thr Val Asp Ala Gln Met Phe Ser Lys
    130                 135                 140 gaa gtt aga aac tgc act gtc ggt gta att ggg ctt gga aga att gga          480
Glu Val Arg Asn Cys Thr Val Gly Val Ile Gly Leu Gly Arg Ile Gly
145                 150                 155                 160 ttt act gca gcc aaa tta ttt aaa ggt tta gga gct aat gtt att gga          528
Phe Thr Ala Ala Lys Leu Phe Lys Gly Leu Gly Ala Asn Val Ile Gly
                165                 170                 175 tat gat atg ttc cct aaa act ggt gta gaa gac ata gtt act caa gtt          576
Tyr Asp Met Phe Pro Lys Thr Gly Val Glu Asp Ile Val Thr Gln Val
            180                 185                 190 cct atg gat gaa tta att aag aaa agt gat att ata act tta cat gct          624
Pro Met Asp Glu Leu Ile Lys Lys Ser Asp Ile Ile Thr Leu His Ala
        195                 200                 205 cca ttt att aaa gaa aat gga aaa att gtt act aaa gaa ttt tta aac          672
Pro Phe Ile Lys Glu Asn Gly Lys Ile Val Thr Lys Glu Phe Leu Asn
    210                 215                 220 aat atg aaa gaa aat tct ata tta ata aat act gct aga gga gaa tta          720
Asn Met Lys Glu Asn Ser Ile Leu Ile Asn Thr Ala Arg Gly Glu Leu
225                 230                 235                 240 atg gat tta gaa gct gtg att gaa gct ctt gaa agt gga cat ctt gca          768
Met Asp Leu Glu Ala Val Ile Glu Ala Leu Glu Ser Gly His Leu Ala
                245                 250                 255 gct gct ggt ata gat act att gaa ggg gaa gtt aat tat ttc ttt aaa          816
Ala Ala Gly Ile Asp Thr Ile Glu Gly Glu Val Asn Tyr Phe Phe Lys
            260                 265                 270 aac ttc tct gac aaa caa gct gaa ttt aga gct gac tac cct cta tac          864
Asn Phe Ser Asp Lys Gln Ala Glu Phe Arg Ala Asp Tyr Pro Leu Tyr
        275                 280                 285 aat aga tta cta gat tta tat cca aga gtt tta gta act cct cat gtt          912
Asn Arg Leu Leu Asp Leu Tyr Pro Arg Val Leu Val Thr Pro His Val
    290                 295                 300 ggt tct tac act gat gaa gct gct tca aac atg ata gaa act tct ttt          960
Gly Ser Tyr Thr Asp Glu Ala Ala Ser Asn Met Ile Glu Thr Ser Phe
305                 310                 315                 320 gaa aac cta aaa gaa tac tta gat act ggt gct tgt aaa aac gat ata         1008
Glu Asn Leu Lys Glu Tyr Leu Asp Thr Gly Ala Cys Lys Asn Asp Ile
                325                 330                 335 aaa gca taa                                                             1017
Lys Ala
```

<210> SEQ ID NO 16
<211> LENGTH: 338
<212> TYPE: PRT
<213> ORGANISM: Fusobacterium nucleatum

<400> SEQUENCE: 16

Met Lys Val Leu Phe Tyr Gly Val Arg Glu Val Glu Ile Pro Leu Phe
1               5                   10                  15

His Glu Leu Asn Lys Lys Glu Gly Phe Gly Tyr Glu Leu Glu Leu Ile
            20                  25                  30

Pro Asp Tyr Leu Asn Ser Lys Glu Thr Ala Glu Lys Ala Lys Gly Phe
        35                  40                  45

Glu Cys Val Val Leu Arg Gly Asn Cys Phe Ala Thr Lys Glu Val Leu
    50                  55                  60

Asp Met Tyr Lys Glu Tyr Gly Val Lys Tyr Leu Leu Thr Arg Thr Val
65                  70                  75                  80

Gly Thr Asn His Ile Asp Val Lys Tyr Ala Lys Glu Leu Gly Phe Lys
                85                  90                  95

Leu Ala Tyr Val Pro Phe Tyr Ser Pro Asn Ala Ile Ala Glu Leu Ala
            100                 105                 110

Val Ser Leu Ala Met Ser Leu Leu Arg His Leu Pro Tyr Thr Ala Glu
        115                 120                 125

Lys Phe Lys Asn Arg Asn Phe Thr Val Asp Ala Gln Met Phe Ser Lys
    130                 135                 140

Glu Val Arg Asn Cys Thr Val Gly Val Ile Gly Leu Gly Arg Ile Gly
145                 150                 155                 160

Phe Thr Ala Ala Lys Leu Phe Lys Gly Leu Gly Ala Asn Val Ile Gly
                165                 170                 175

Tyr Asp Met Phe Pro Lys Thr Gly Val Glu Asp Ile Val Thr Gln Val
            180                 185                 190

Pro Met Asp Glu Leu Ile Lys Lys Ser Asp Ile Ile Thr Leu His Ala
        195                 200                 205

Pro Phe Ile Lys Glu Asn Gly Lys Ile Val Thr Lys Glu Phe Leu Asn
    210                 215                 220

Asn Met Lys Glu Asn Ser Ile Leu Ile Asn Thr Ala Arg Gly Glu Leu
225                 230                 235                 240

Met Asp Leu Glu Ala Val Ile Glu Ala Leu Glu Ser Gly His Leu Ala
                245                 250                 255

Ala Ala Gly Ile Asp Thr Ile Glu Gly Glu Val Asn Tyr Phe Phe Lys
            260                 265                 270

Asn Phe Ser Asp Lys Gln Ala Glu Phe Arg Ala Asp Tyr Pro Leu Tyr
        275                 280                 285

Asn Arg Leu Leu Asp Leu Tyr Pro Arg Val Leu Val Thr Pro His Val
    290                 295                 300

Gly Ser Tyr Thr Asp Glu Ala Ala Ser Asn Met Ile Glu Thr Ser Phe
305                 310                 315                 320

Glu Asn Leu Lys Glu Tyr Leu Asp Thr Gly Ala Cys Lys Asn Asp Ile
                325                 330                 335

Lys Ala

<210> SEQ ID NO 17
<211> LENGTH: 274
<212> TYPE: DNA
<213> ORGANISM: Clostridium symbiosum

<400> SEQUENCE: 17
gtgagtaata aagtgtgtac attacaagag gcggttgcta agtatgtaga agacggcgat      60
tcgatctcct tcggtggttt tacaaccaac aaaaaaccga tggcagcagt ccgcgagatc     120

```
cttcgtcagg gcaaaaaaga tttattgca tgggccggtc ctgccggttc tgactgggat        180
atgttaattg gtgaggatcg tgtaaaagca tatatcaact gctatacggc tgattccggt        240
gtaaccaatg tatcccgccg cttccgtaga ataa                                   274
```

<210> SEQ ID NO 18
<211> LENGTH: 91
<212> TYPE: PRT
<213> ORGANISM: Clostridium symbiosum

<400> SEQUENCE: 18

```
Met Ser Asn Lys Val Cys Thr Leu Gln Glu Ala Val Ala Lys Tyr Val
1               5                   10                  15

Glu Asp Gly Asp Ser Ile Ser Phe Gly Gly Phe Thr Thr Asn Lys Lys
                20                  25                  30

Pro Met Ala Ala Val Arg Glu Ile Leu Arg Gln Gly Lys Lys Asp Phe
            35                  40                  45

Ile Ala Trp Ala Gly Pro Ala Gly Ser Asp Trp Asp Met Leu Ile Gly
        50                  55                  60

Glu Asp Arg Val Lys Ala Tyr Ile Asn Cys Tyr Thr Ala Asp Ser Gly
65                  70                  75                  80

Val Thr Asn Val Ser Arg Arg Phe Arg Arg Ile
                85                  90
```

<210> SEQ ID NO 19
<211> LENGTH: 638
<212> TYPE: DNA
<213> ORGANISM: Clostridium symbiosum

<400> SEQUENCE: 19

```
tgatggactg ctcaccaatc gagattccgc gttccgtagg tgaccttcgt tttatggctc        60
attgcggatg ccagtggcct aatatccgtt ttatcggatt tgaggcaaat gagtggctgc       120
atgacacaga cagactgatc gctttcatcg gcggcgcaca gatcgaccca tacgaaacg        180 tgaactccac ctgtatcggt gactatcacg ctccgaagac tcgtttcaca ggctccggcg       240
gtgcaaacgc aatcgcaacc ttctctaaca caatcatcat gattcagcac gaaaaacgcc       300
gtttcatgca aagatcgac tacgttacaa gcccgggctg gattgacgga cccggcggac       360
gcgagagact cggccttccg ggcaaccgtg gacctcaggc agttgttacc gaccgcggta       420
tcctcaaatt tgacgagaag acaaagagaa tgtaccttgc aggctactat gagacatctt       480
caccggaaga cgttatcgag aatacaggat tcgatatcga cgtttccaga gcagttaagc       540
tggatgcacc ggcaccggaa gttatccgca tgatccgtga ggagatcgat cccggacagg       600
catttatcca ggttccgaag gaagagccgg ctaactaa                               638
```

<210> SEQ ID NO 20
<211> LENGTH: 211
<212> TYPE: PRT
<213> ORGANISM: Clostridium symbiosum

<400> SEQUENCE: 20

```
Met Asp Cys Ser Pro Ile Glu Ile Pro Arg Ser Val Gly Asp Leu Arg
1               5                   10                  15

Phe Met Ala His Cys Gly Cys Gln Trp Pro Asn Ile Arg Phe Ile Gly
                20                  25                  30

Phe Glu Ala Asn Glu Trp Leu His Asp Thr Asp Arg Leu Ile Ala Phe
            35                  40                  45
```

```
Ile Gly Gly Ala Gln Ile Asp Pro Tyr Gly Asn Val Asn Ser Thr Cys
 50                  55                  60

Ile Gly Asp Tyr His Ala Pro Lys Thr Arg Phe Thr Gly Ser Gly Gly
 65                      70                  75                  80

Ala Asn Ala Ile Ala Thr Phe Ser Asn Thr Ile Met Ile Gln His
                 85                  90                  95

Glu Lys Arg Arg Phe Met Gln Lys Ile Asp Tyr Val Thr Ser Pro Gly
            100                 105                 110

Trp Ile Asp Gly Pro Gly Gly Arg Glu Arg Leu Gly Leu Pro Gly Asn
            115                 120                 125

Arg Gly Pro Gln Ala Val Val Thr Asp Arg Gly Ile Leu Lys Phe Asp
        130                 135                 140

Glu Lys Thr Lys Arg Met Tyr Leu Ala Gly Tyr Tyr Glu Thr Ser Ser
145                 150                 155                 160

Pro Glu Asp Val Ile Glu Asn Thr Gly Phe Asp Ile Asp Val Ser Arg
                165                 170                 175

Ala Val Lys Leu Asp Ala Pro Ala Pro Glu Val Ile Arg Met Ile Arg
            180                 185                 190

Glu Glu Ile Asp Pro Gly Gln Ala Phe Ile Gln Val Pro Lys Glu Glu
            195                 200                 205

Pro Ala Asn
    210

<210> SEQ ID NO 21
<211> LENGTH: 966
<212> TYPE: DNA
<213> ORGANISM: Fusobacterium nucleatum
<220> FEATURE:
<221> NAME/KEY: CDS
<222> LOCATION: (1)..(966)

<400> SEQUENCE: 21 gtg agc aaa ata atg tct tta cat gat gca ata gca aaa tat gtt gaa    48
Val Ser Lys Ile Met Ser Leu His Asp Ala Ile Ala Lys Tyr Val Glu
  1               5                  10                  15 tct ggc gat agc tta tgt ttt gga gga ttc aca aca aac aga aag cct    96
Ser Gly Asp Ser Leu Cys Phe Gly Gly Phe Thr Thr Asn Arg Lys Pro
                 20                  25                  30 tat gcg gct gtt tac gaa att att aga caa gga caa aca gat ttt ata   144
Tyr Ala Ala Val Tyr Glu Ile Ile Arg Gln Gly Gln Thr Asp Phe Ile
             35                  40                  45 gga tat tct ggt cca gca ggt gga gat tgg gat atg tta ata gga tgt   192
Gly Tyr Ser Gly Pro Ala Gly Gly Asp Trp Asp Met Leu Ile Gly Cys
 50                  55                  60 gga aga ata aaa gct ttc ata aac tgt tat ata gct aac tca gga tat   240
Gly Arg Ile Lys Ala Phe Ile Asn Cys Tyr Ile Ala Asn Ser Gly Tyr
 65                  70                  75                  80 act aat gtt tgt aga aga ttc aga gat gca gta gaa aag aaa cat aat   288
Thr Asn Val Cys Arg Arg Phe Arg Asp Ala Val Glu Lys Lys His Asn
                 85                  90                  95 tta tta tta gaa gat tat tct caa gat gtt att atg tta atg tta cat   336
Leu Leu Leu Glu Asp Tyr Ser Gln Asp Val Ile Met Leu Met Leu His
            100                 105                 110 gct tct tca tta ggt tta cca tat tta cca gta aaa tta atg gaa ggt   384
Ala Ser Ser Leu Gly Leu Pro Tyr Leu Pro Val Lys Leu Met Glu Gly
        115                 120                 125 agt gac cta gaa tac aaa tgg gga ata agt gcg gaa atc aga aag aca   432
Ser Asp Leu Glu Tyr Lys Trp Gly Ile Ser Ala Glu Ile Arg Lys Thr
130                 135                 140
```

```
att cct aaa ttg cct gac aag aaa tta gaa aga ata cct aat cct ttt       480
Ile Pro Lys Leu Pro Asp Lys Lys Leu Glu Arg Ile Pro Asn Pro Phe
145                 150                 155                 160 aaa gaa gga gaa gaa gta ata gca gtt cca gtt cca aga cta gat aca       528
Lys Glu Gly Glu Glu Val Ile Ala Val Pro Val Pro Arg Leu Asp Thr
                165                 170                 175 gct ata att tct gtt caa aaa gct tct att aat gga act tgc tca ata       576
Ala Ile Ile Ser Val Gln Lys Ala Ser Ile Asn Gly Thr Cys Ser Ile
            180                 185                 190 gaa gga gat gaa ttc cat gat ata gat att gca ata gct gct aaa aaa       624
Glu Gly Asp Glu Phe His Asp Ile Asp Ile Ala Ile Ala Ala Lys Lys
        195                 200                 205 gtt ata gtt ata gca gaa gaa att gta aca gaa gaa gaa att aga aga       672
Val Ile Val Ile Ala Glu Glu Ile Val Thr Glu Glu Glu Ile Arg Arg
210                 215                 220 gat cct tct aaa aac tca ata cct caa ttt tgt gta gat gct gta gtt       720
Asp Pro Ser Lys Asn Ser Ile Pro Gln Phe Cys Val Asp Ala Val Val
225                 230                 235                 240 cat gta cct tat gga aca cat cca tct caa cta tat aat tat tat gac       768
His Val Pro Tyr Gly Thr His Pro Ser Gln Leu Tyr Asn Tyr Tyr Asp
                245                 250                 255 tat gat gct gac ttc tat aaa atg tat gat aaa gta act aaa aca gat       816
Tyr Asp Ala Asp Phe Tyr Lys Met Tyr Asp Lys Val Thr Lys Thr Asp
            260                 265                 270 gaa gac ttt gaa caa ttc ata aaa gaa tgg gtt ata gat gtt aag gat       864
Glu Asp Phe Glu Gln Phe Ile Lys Glu Trp Val Ile Asp Val Lys Asp
        275                 280                 285 cat gaa gga tac tta gct aaa tta ggg tta cca aga gta agc aaa tta       912
His Glu Gly Tyr Leu Ala Lys Leu Gly Leu Pro Arg Val Ser Lys Leu
290                 295                 300 aaa gta gta cca gga ttc caa tat gct gca aaa tta gtt aag gat ggt       960
Lys Val Val Pro Gly Phe Gln Tyr Ala Ala Lys Leu Val Lys Asp Gly
305                 310                 315                 320 gaa taa                                                               966
Glu

<210> SEQ ID NO 22
<211> LENGTH: 321
<212> TYPE: PRT
<213> ORGANISM: Fusobacterium nucleatum

<400> SEQUENCE: 22

Val Ser Lys Ile Met Ser Leu His Asp Ala Ile Ala Lys Tyr Val Glu
1               5                   10                  15

Ser Gly Asp Ser Leu Cys Phe Gly Gly Phe Thr Thr Asn Arg Lys Pro
            20                  25                  30

Tyr Ala Ala Val Tyr Glu Ile Arg Gln Gly Gln Thr Asp Phe Ile
        35                  40                  45

Gly Tyr Ser Gly Pro Ala Gly Gly Asp Trp Asp Met Leu Ile Gly Cys
    50                  55                  60

Gly Arg Ile Lys Ala Phe Ile Asn Cys Tyr Ile Ala Asn Ser Gly Tyr
65                  70                  75                  80

Thr Asn Val Cys Arg Arg Phe Arg Asp Ala Val Glu Lys Lys His Asn
                85                  90                  95

Leu Leu Leu Glu Asp Tyr Ser Gln Asp Val Ile Met Leu Met Leu His
            100                 105                 110

Ala Ser Ser Leu Gly Leu Pro Tyr Leu Pro Val Lys Leu Met Glu Gly
        115                 120                 125
```

```
Ser Asp Leu Glu Tyr Lys Trp Gly Ile Ser Ala Glu Ile Arg Lys Thr
    130                 135                 140

Ile Pro Lys Leu Pro Asp Lys Lys Leu Glu Arg Ile Pro Asn Pro Phe
145                 150                 155                 160

Lys Glu Gly Glu Val Ile Ala Val Pro Val Pro Arg Leu Asp Thr
                165                 170                 175

Ala Ile Ile Ser Val Gln Lys Ala Ser Ile Asn Gly Thr Cys Ser Ile
                180                 185                 190

Glu Gly Asp Glu Phe His Asp Ile Asp Ile Ala Ile Ala Ala Lys Lys
        195                 200                 205

Val Ile Val Ile Ala Glu Ile Val Thr Glu Glu Ile Arg Arg
210                 215                 220

Asp Pro Ser Lys Asn Ser Ile Pro Gln Phe Cys Val Asp Ala Val Val
225                 230                 235                 240

His Val Pro Tyr Gly Thr His Pro Ser Gln Leu Tyr Asn Tyr Tyr Asp
                245                 250                 255

Tyr Asp Ala Asp Phe Tyr Lys Met Tyr Asp Lys Val Thr Lys Thr Asp
                260                 265                 270

Glu Asp Phe Glu Gln Phe Ile Lys Glu Trp Val Ile Asp Val Lys Asp
        275                 280                 285

His Glu Gly Tyr Leu Ala Lys Leu Gly Leu Pro Arg Val Ser Lys Leu
    290                 295                 300

Lys Val Val Pro Gly Phe Gln Tyr Ala Ala Lys Leu Val Lys Asp Gly
305                 310                 315                 320

Glu

<210> SEQ ID NO 23
<211> LENGTH: 804
<212> TYPE: DNA
<213> ORGANISM: Fusobacterium nucleatum
<220> FEATURE:
<221> NAME/KEY: CDS
<222> LOCATION: (1)..(801)

<400> SEQUENCE: 23 atg gca aaa aat tat aaa aac tat aca aat aaa gaa atg caa gct att      48
Met Ala Lys Asn Tyr Lys Asn Tyr Thr Asn Lys Glu Met Gln Ala Ile
1               5                   10                  15 acc att gct aaa gaa att aaa gat gga caa ata gtt att gta gga aca      96
Thr Ile Ala Lys Glu Ile Lys Asp Gly Gln Ile Val Ile Val Gly Thr
                20                  25                  30 gga tta cct tta ata gga gca act gtt gct aaa aat aaa ttt gcc cct     144
Gly Leu Pro Leu Ile Gly Ala Thr Val Ala Lys Asn Lys Phe Ala Pro
            35                  40                  45 aac tgt aaa tta ata gtt gaa agt gga tta atg gat tgt agt cca ata     192
Asn Cys Lys Leu Ile Val Glu Ser Gly Leu Met Asp Cys Ser Pro Ile
        50                  55                  60 gaa gtt cca aga agt gtt gga gat tta aga ctt atg gga cac tgt gct     240
Glu Val Pro Arg Ser Val Gly Asp Leu Arg Leu Met Gly His Cys Ala
65                  70                  75                  80 gtt caa tgg cca aat gta aga ttt ata ggt ttt gaa act aat gaa tac     288
Val Gln Trp Pro Asn Val Arg Phe Ile Gly Phe Glu Thr Asn Glu Tyr
                85                  90                  95 tta aat gga aat gac aga atg ata gct ttc att gga gga gct caa ata     336
Leu Asn Gly Asn Asp Arg Met Ile Ala Phe Ile Gly Gly Ala Gln Ile
            100                 105                 110 aat cct tat gga gat tta aac tct act atc att ggt gat gac tat ata     384
```

| | | | | | | | | | | | | | | |
|---|---|---|---|---|---|---|---|---|---|---|---|---|---|---|
| | | Asn | Pro | Tyr | Gly | Asp | Leu | Asn | Ser | Thr | Ile | Ile | Gly | Asp | Asp | Tyr | Ile |
| | | | | 115 | | | | 120 | | | | 125 | | | |

```
aaa cca aaa aca aga ttt aca gga agt gga gga gct aat ggt ata gct      432
Lys Pro Lys Thr Arg Phe Thr Gly Ser Gly Gly Ala Asn Gly Ile Ala
    130                 135                 140 act tac tca aat act gta ata atg atg caa cat gaa aaa aga aga ttt      480
Thr Tyr Ser Asn Thr Val Ile Met Met Gln His Glu Lys Arg Arg Phe
145                 150                 155                 160 ata gat aaa att gac tat ata aca agt gtt gga tgg gca gga gga cca      528
Ile Asp Lys Ile Asp Tyr Ile Thr Ser Val Gly Trp Ala Gly Gly Pro
                165                 170                 175 gga ggg aga gaa aaa tta gga ctt cct gga aac aga gga cca ctt gct      576
Gly Gly Arg Glu Lys Leu Gly Leu Pro Gly Asn Arg Gly Pro Leu Ala
            180                 185                 190 gtt gtt aca gac aaa ggt att tta aga ttt gat gaa aag act aag aga      624
Val Val Thr Asp Lys Gly Ile Leu Arg Phe Asp Glu Lys Thr Lys Arg
        195                 200                 205 atg tac tta gca gga tat tat cca gga gtt aca ata gaa gat ata gtt      672
Met Tyr Leu Ala Gly Tyr Tyr Pro Gly Val Thr Ile Glu Asp Ile Val
    210                 215                 220 gaa aac act gga ttt gaa att gat act tca aga gca gta caa tta gaa      720
Glu Asn Thr Gly Phe Glu Ile Asp Thr Ser Arg Ala Val Gln Leu Glu
225                 230                 235                 240 gct cca agt gaa gaa atc ata aaa atg ata aga gaa gat ata gat cca      768
Ala Pro Ser Glu Glu Ile Ile Lys Met Ile Arg Glu Asp Ile Asp Pro
                245                 250                 255 gga caa gca ttt ata aaa gtt cca gtg gaa gaa taa                      804
Gly Gln Ala Phe Ile Lys Val Pro Val Glu Glu
            260                 265
```

<210> SEQ ID NO 24
<211> LENGTH: 267
<212> TYPE: PRT
<213> ORGANISM: Fusobacterium nucleatum

<400> SEQUENCE: 24

```
Met Ala Lys Asn Tyr Lys Asn Tyr Thr Asn Lys Glu Met Gln Ala Ile
1               5                   10                  15

Thr Ile Ala Lys Glu Ile Lys Asp Gly Gln Ile Val Ile Val Gly Thr
            20                  25                  30

Gly Leu Pro Leu Ile Gly Ala Thr Val Ala Lys Asn Lys Phe Ala Pro
        35                  40                  45

Asn Cys Lys Leu Ile Val Glu Ser Gly Leu Met Asp Cys Ser Pro Ile
    50                  55                  60

Glu Val Pro Arg Ser Val Gly Asp Leu Arg Leu Met Gly His Cys Ala
65                  70                  75                  80

Val Gln Trp Pro Asn Val Arg Phe Ile Gly Phe Glu Thr Asn Glu Tyr
                85                  90                  95

Leu Asn Gly Asn Asp Arg Met Ile Ala Phe Ile Gly Gly Ala Gln Ile
            100                 105                 110

Asn Pro Tyr Gly Asp Leu Asn Ser Thr Ile Ile Gly Asp Asp Tyr Ile
        115                 120                 125

Lys Pro Lys Thr Arg Phe Thr Gly Ser Gly Gly Ala Asn Gly Ile Ala
    130                 135                 140

Thr Tyr Ser Asn Thr Val Ile Met Met Gln His Glu Lys Arg Arg Phe
145                 150                 155                 160

Ile Asp Lys Ile Asp Tyr Ile Thr Ser Val Gly Trp Ala Gly Gly Pro
                165                 170                 175
```

```
Gly Gly Arg Glu Lys Leu Gly Leu Pro Gly Asn Arg Gly Pro Leu Ala
            180                 185                 190

Val Val Thr Asp Lys Gly Ile Leu Arg Phe Asp Glu Lys Thr Lys Arg
            195                 200                 205

Met Tyr Leu Ala Gly Tyr Tyr Pro Gly Val Thr Ile Glu Asp Ile Val
    210                 215                 220

Glu Asn Thr Gly Phe Glu Ile Asp Thr Ser Arg Ala Val Gln Leu Glu
225                 230                 235                 240

Ala Pro Ser Glu Glu Ile Ile Lys Met Ile Arg Glu Asp Ile Asp Pro
                245                 250                 255

Gly Gln Ala Phe Ile Lys Val Pro Val Glu Glu
            260                 265

<210> SEQ ID NO 25
<211> LENGTH: 1434
<212> TYPE: DNA
<213> ORGANISM: Acidaminococcus fermentans
<220> FEATURE:
<221> NAME/KEY: CDS
<222> LOCATION: (1)..(1434)

<400> SEQUENCE: 25 atg cca aag aca gta agc cct ggc gtt cag gca ttg aga gat gta gtt      48
Met Pro Lys Thr Val Ser Pro Gly Val Gln Ala Leu Arg Asp Val Val
1               5                   10                  15 gaa aag gtt tac aga gaa ctg cgg gaa ccg aaa gaa aga gga gaa aaa      96
Glu Lys Val Tyr Arg Glu Leu Arg Glu Pro Lys Glu Arg Gly Glu Lys
                20                  25                  30 gta ggc tgg tcc tct tcc aag ttc ccc tgc gaa ctg gct gaa tct ttt     144
Val Gly Trp Ser Ser Ser Lys Phe Pro Cys Glu Leu Ala Glu Ser Phe
            35                  40                  45 cgg ctg cat gtt ggg tat ccg gaa aac cag gct gct ggt atc gct gcc     192
Arg Leu His Val Gly Tyr Pro Glu Asn Gln Ala Ala Gly Ile Ala Ala
        50                  55                  60 aac cgt gac ggc gaa gtg atg tgc cag gct gca gaa gat atc ggt tat     240
Asn Arg Asp Gly Glu Val Met Cys Gln Ala Ala Glu Asp Ile Gly Tyr
65                  70                  75                  80 gac aac gat atc tgc ggc tat gcc cgt att tcc ctg gct tat gct gcc     288
Asp Asn Asp Ile Cys Gly Tyr Ala Arg Ile Ser Leu Ala Tyr Ala Ala
                85                  90                  95 ggg ttc cgg ggt gcc aac aaa atg gac aaa gat ggc aac tat gtc atc     336
Gly Phe Arg Gly Ala Asn Lys Met Asp Lys Asp Gly Asn Tyr Val Ile
            100                 105                 110 aac ccc cac agc ggc aaa cag atg aaa gat gcc aat ggc aaa aag gta     384
Asn Pro His Ser Gly Lys Gln Met Lys Asp Ala Asn Gly Lys Lys Val
        115                 120                 125 ttc gac gca gat ggc aaa ccc gta atc gat ccc aag acc ctg aaa ccc     432
Phe Asp Ala Asp Gly Lys Pro Val Ile Asp Pro Lys Thr Leu Lys Pro
    130                 135                 140 ttt gcc acc acc gac aac atc tat gaa atc gct gct ctg ccg gaa ggg     480
Phe Ala Thr Thr Asp Asn Ile Tyr Glu Ile Ala Ala Leu Pro Glu Gly
145                 150                 155                 160 gaa gaa aag acc cgc cgc cag aat gcc ctg cac aaa tat cgt cag atg     528
Glu Glu Lys Thr Arg Arg Gln Asn Ala Leu His Lys Tyr Arg Gln Met
                165                 170                 175 acc atg ccc atg ccg gac ttc gtg ctg tgc tgc aac aac atc tgc aac     576
Thr Met Pro Met Pro Asp Phe Val Leu Cys Cys Asn Asn Ile Cys Asn
            180                 185                 190 tgc atg acc aaa tgg tat gaa gac att gcc cgt cgg cac aac att cct     624
```

```
                Cys Met Thr Lys Trp Tyr Glu Asp Ile Ala Arg Arg His Asn Ile Pro
                            195                 200                 205 ttg atc atg atc gac gtt cct tac aac gaa ttc gac cat gtc aac gaa          672
Leu Ile Met Ile Asp Val Pro Tyr Asn Glu Phe Asp His Val Asn Glu
210                 215                 220 gcc aac gtg aaa tac atc cgg tcc cag ctg gat acg gcc atc cgt caa          720
Ala Asn Val Lys Tyr Ile Arg Ser Gln Leu Asp Thr Ala Ile Arg Gln
225                 230                 235                 240 atg gaa gaa atc acc ggc aag aag ttc gat gaa gac aaa ttc gaa cag          768
Met Glu Glu Ile Thr Gly Lys Lys Phe Asp Glu Asp Lys Phe Glu Gln
                245                 250                 255 tgc tgc cag aac gcc aac cgt act gcc aaa gca tgg ctg aag gtt tgc          816
Cys Cys Gln Asn Ala Asn Arg Thr Ala Lys Ala Trp Leu Lys Val Cys
            260                 265                 270 gac tac ctg cag tac aaa ccg gct ccg ttc aac ggg ttc gac ctg ttc          864
Asp Tyr Leu Gln Tyr Lys Pro Ala Pro Phe Asn Gly Phe Asp Leu Phe
        275                 280                 285 aac cat atg gct gac gtg gtt acc gcc cgt ggc cgt gtg gaa gct gct          912
Asn His Met Ala Asp Val Val Thr Ala Arg Gly Arg Val Glu Ala Ala
    290                 295                 300 gaa gct ttc gaa ctg ctg gcc aag gaa ctg gaa cag cat gtg aag gaa          960
Glu Ala Phe Glu Leu Leu Ala Lys Glu Leu Glu Gln His Val Lys Glu
305                 310                 315                 320 ggc acc acc acc gct ccc ttc aaa gaa cag cat cgt atc atg ttc gaa         1008
Gly Thr Thr Thr Ala Pro Phe Lys Glu Gln His Arg Ile Met Phe Glu
                325                 330                 335 ggg atc ccc tgc tgg ccg aaa ctg ccg aac ctg ttc aaa ccg ctg aaa         1056
Gly Ile Pro Cys Trp Pro Lys Leu Pro Asn Leu Phe Lys Pro Leu Lys
            340                 345                 350 gcc aac ggc ctg aac atc acc ggc gtt gta tat gct cct gct ttc ggg         1104
Ala Asn Gly Leu Asn Ile Thr Gly Val Val Tyr Ala Pro Ala Phe Gly
        355                 360                 365 ttc gtg tac aac aac ctg gac gaa ttg gtc aaa gcc tac tgc aaa gcc         1152
Phe Val Tyr Asn Asn Leu Asp Glu Leu Val Lys Ala Tyr Cys Lys Ala
    370                 375                 380 ccg aac tcc gtc agc atc gaa cag ggt gtt gcc tgg cgt gaa ggc ctg         1200
Pro Asn Ser Val Ser Ile Glu Gln Gly Val Ala Trp Arg Glu Gly Leu
385                 390                 395                 400 atc cgc gac aac aag gtt gac ggc gta ctg gtt cac tac aac cgg tcc         1248
Ile Arg Asp Asn Lys Val Asp Gly Val Leu Val His Tyr Asn Arg Ser
                405                 410                 415 tgc aaa ccc tgg agc ggc tac atg cct gaa atg cag cgt cgt ttc acc         1296
Cys Lys Pro Trp Ser Gly Tyr Met Pro Glu Met Gln Arg Arg Phe Thr
            420                 425                 430 aaa gac atg ggt atc ccc act gct gga ttc gac ggt gac cag gct gac         1344
Lys Asp Met Gly Ile Pro Thr Ala Gly Phe Asp Gly Asp Gln Ala Asp
        435                 440                 445 ccg aga aac ttc aac gcg gct cag tat gag acc cgt gtt cag ggc ttg         1392
Pro Arg Asn Phe Asn Ala Ala Gln Tyr Glu Thr Arg Val Gln Gly Leu
    450                 455                 460 gtc gaa gcc atg gaa gca aat gat gaa aag aag ggg aaa taa               1434
Val Glu Ala Met Glu Ala Asn Asp Glu Lys Lys Gly Lys
465                 470                 475
```

<210> SEQ ID NO 26
<211> LENGTH: 477
<212> TYPE: PRT
<213> ORGANISM: Acidaminococcus fermentans

<400> SEQUENCE: 26

```
Met Pro Lys Thr Val Ser Pro Gly Val Gln Ala Leu Arg Asp Val Val
1               5                   10                  15

Glu Lys Val Tyr Arg Glu Leu Arg Glu Pro Lys Glu Arg Gly Glu Lys
            20                  25                  30

Val Gly Trp Ser Ser Ser Lys Phe Pro Cys Glu Leu Ala Glu Ser Phe
        35                  40                  45

Arg Leu His Val Gly Tyr Pro Glu Asn Gln Ala Ala Gly Ile Ala Ala
    50                  55                  60

Asn Arg Asp Gly Glu Val Met Cys Gln Ala Ala Glu Asp Ile Gly Tyr
65                  70                  75                  80

Asp Asn Asp Ile Cys Gly Tyr Ala Arg Ile Ser Leu Ala Tyr Ala Ala
                85                  90                  95

Gly Phe Arg Gly Ala Asn Lys Met Asp Lys Asp Gly Asn Tyr Val Ile
            100                 105                 110

Asn Pro His Ser Gly Lys Gln Met Lys Asp Ala Asn Gly Lys Lys Val
        115                 120                 125

Phe Asp Ala Asp Gly Lys Pro Val Ile Asp Pro Lys Thr Leu Lys Pro
    130                 135                 140

Phe Ala Thr Thr Asp Asn Ile Tyr Glu Ile Ala Ala Leu Pro Glu Gly
145                 150                 155                 160

Glu Glu Lys Thr Arg Arg Gln Asn Ala Leu His Lys Tyr Arg Gln Met
            165                 170                 175

Thr Met Pro Met Pro Asp Phe Val Leu Cys Cys Asn Asn Ile Cys Asn
        180                 185                 190

Cys Met Thr Lys Trp Tyr Glu Asp Ile Ala Arg Arg His Asn Ile Pro
        195                 200                 205

Leu Ile Met Ile Asp Val Pro Tyr Asn Glu Phe Asp His Val Asn Glu
    210                 215                 220

Ala Asn Val Lys Tyr Ile Arg Ser Gln Leu Asp Thr Ala Ile Arg Gln
225                 230                 235                 240

Met Glu Glu Ile Thr Gly Lys Lys Phe Asp Asp Lys Phe Glu Gln
            245                 250                 255

Cys Cys Gln Asn Ala Asn Arg Thr Ala Lys Ala Trp Leu Lys Val Cys
        260                 265                 270

Asp Tyr Leu Gln Tyr Lys Pro Ala Pro Phe Asn Gly Phe Asp Leu Phe
    275                 280                 285

Asn His Met Ala Asp Val Val Thr Ala Arg Gly Arg Val Glu Ala Ala
    290                 295                 300

Glu Ala Phe Glu Leu Leu Ala Lys Glu Leu Glu Gln His Val Lys Glu
305                 310                 315                 320

Gly Thr Thr Thr Ala Pro Phe Lys Glu Gln His Arg Ile Met Phe Glu
            325                 330                 335

Gly Ile Pro Cys Trp Pro Lys Leu Pro Asn Leu Phe Lys Pro Leu Lys
        340                 345                 350

Ala Asn Gly Leu Asn Ile Thr Gly Val Val Tyr Ala Pro Ala Phe Gly
        355                 360                 365

Phe Val Tyr Asn Asn Leu Asp Glu Leu Val Lys Ala Tyr Cys Lys Ala
    370                 375                 380

Pro Asn Ser Val Ser Ile Glu Gln Gly Val Ala Trp Arg Glu Gly Leu
385                 390                 395                 400

Ile Arg Asp Asn Lys Val Asp Gly Val Leu Val His Tyr Asn Arg Ser
            405                 410                 415

Cys Lys Pro Trp Ser Gly Tyr Met Pro Glu Met Gln Arg Arg Phe Thr
```

```
              420                 425                 430
Lys Asp Met Gly Ile Pro Thr Ala Gly Phe Asp Gly Asp Gln Ala Asp
            435                 440                 445

Pro Arg Asn Phe Asn Ala Ala Gln Tyr Glu Thr Arg Val Gln Gly Leu
    450                 455                 460

Val Glu Ala Met Glu Ala Asn Asp Glu Lys Lys Gly Lys
465                 470                 475

<210> SEQ ID NO 27
<211> LENGTH: 1140
<212> TYPE: DNA
<213> ORGANISM: Acidaminococcus fermentans
<220> FEATURE:
<221> NAME/KEY: CDS
<222> LOCATION: (1)..(1140)

<400> SEQUENCE: 27 atg gct atc agt gca ctt att gaa gag ttc caa aaa gta tct gcc agc        48
Met Ala Ile Ser Ala Leu Ile Glu Glu Phe Gln Lys Val Ser Ala Ser
1               5                   10                  15 ccg aag acc atg ctg gcc aaa tat aaa gcc cag gga aaa aaa gcc atc        96
Pro Lys Thr Met Leu Ala Lys Tyr Lys Ala Gln Gly Lys Lys Ala Ile
            20                  25                  30 ggc tgc ctg ccg tac tat gtt ccg gaa gaa ctg gtc tat gct gca ggc       144
Gly Cys Leu Pro Tyr Tyr Val Pro Glu Glu Leu Val Tyr Ala Ala Gly
        35                  40                  45 atg gtt ccc atg ggt gta tgg ggc tgc aat ggc aaa cag gaa gtc cgt       192
Met Val Pro Met Gly Val Trp Gly Cys Asn Gly Lys Gln Glu Val Arg
    50                  55                  60 tcc aag gaa tac tgt gct tcc ttc tac tgc acc att gcc cag cag tct       240
Ser Lys Glu Tyr Cys Ala Ser Phe Tyr Cys Thr Ile Ala Gln Gln Ser
65                  70                  75                  80 ctg gaa atg ctg ctg gac ggg acc ctg gat ggg ttg gac ggg atc atc       288
Leu Glu Met Leu Leu Asp Gly Thr Leu Asp Gly Leu Asp Gly Ile Ile
                85                  90                  95 act ccg gta ctg tgt gat acc ctg cgt ccc atg agc cag aac ttc aaa       336
Thr Pro Val Leu Cys Asp Thr Leu Arg Pro Met Ser Gln Asn Phe Lys
            100                 105                 110 gtg gcc atg aaa gac aag atg ccg gtt att ttc ctg gct cat ccc cag       384
Val Ala Met Lys Asp Lys Met Pro Val Ile Phe Leu Ala His Pro Gln
        115                 120                 125 gtc cgt cag aat gcc gcc ggc aag cag ttc acc tat gat gcc tac agc       432
Val Arg Gln Asn Ala Ala Gly Lys Gln Phe Thr Tyr Asp Ala Tyr Ser
    130                 135                 140 gaa gtg aaa ggc cat ctg gaa gaa atc tgc ggc cat gaa atc acc aat       480
Glu Val Lys Gly His Leu Glu Glu Ile Cys Gly His Glu Ile Thr Asn
145                 150                 155                 160 gat gcc atc ctg gat gcc atc aaa gtg tac aac aag agc cgt gct gcc       528
Asp Ala Ile Leu Asp Ala Ile Lys Val Tyr Asn Lys Ser Arg Ala Ala
                165                 170                 175 cgc cgc gaa ttc tgc aaa ctg gcc aac gaa cat cct gat ctg atc ccg       576
Arg Arg Glu Phe Cys Lys Leu Ala Asn Glu His Pro Asp Leu Ile Pro
            180                 185                 190 gct tcc gta cgg gcc acc gta ctg cgt gcc gct tac ttc atg ctg aag       624
Ala Ser Val Arg Ala Thr Val Leu Arg Ala Ala Tyr Phe Met Leu Lys
        195                 200                 205 gat gaa tac acc gaa aag ctg gaa gaa ctg aac aag gaa ctg gca gct       672
Asp Glu Tyr Thr Glu Lys Leu Glu Glu Leu Asn Lys Glu Leu Ala Ala
    210                 215                 220 gct cct gcc ggc aag ttc gac ggc cac aaa gtg gtt gtt tcc ggc atc       720
Ala Pro Ala Gly Lys Phe Asp Gly His Lys Val Val Val Ser Gly Ile
```

```
Ala Pro Ala Gly Lys Phe Asp Gly His Lys Val Val Ser Gly Ile
225                 230                 235                 240 atc tac aac acg ccc ggc atc ctg aaa gcc atg gat gac aac aaa ctg       768
Ile Tyr Asn Thr Pro Gly Ile Leu Lys Ala Met Asp Asp Asn Lys Leu
                    245                 250                 255 gcc att gct gct gat gac tgc gct tat gaa agc cgc agc ttt gcc gtg       816
Ala Ile Ala Ala Asp Asp Cys Ala Tyr Glu Ser Arg Ser Phe Ala Val
                260                 265                 270 gat gct ccg gaa gat ctg gac aac gga ctg cat gct ctg gct gta cag       864
Asp Ala Pro Glu Asp Leu Asp Asn Gly Leu His Ala Leu Ala Val Gln
            275                 280                 285 ttc tcc aaa cag aag aac gat gtt ctg ctg tac gat cct gaa ttt gcc       912
Phe Ser Lys Gln Lys Asn Asp Val Leu Leu Tyr Asp Pro Glu Phe Ala
        290                 295                 300 aag aat acc cgt tct gaa cac gtt ggc aat ctg gta aaa gaa agc ggc       960
Lys Asn Thr Arg Ser Glu His Val Gly Asn Leu Val Lys Glu Ser Gly
305                 310                 315                 320 gca gaa gga ctg atc gtg ttc atg atg cag ttc tgc gat ccg gaa gaa      1008
Ala Glu Gly Leu Ile Val Phe Met Met Gln Phe Cys Asp Pro Glu Glu
                    325                 330                 335 atg gaa tat cct gat ctg aag aag gct ctg gat gcc cac cac att cct      1056
Met Glu Tyr Pro Asp Leu Lys Lys Ala Leu Asp Ala His His Ile Pro
                340                 345                 350 cat gtg aag att ggt gtg gac cag atg acc cgg gac ttt ggt cag gcc      1104
His Val Lys Ile Gly Val Asp Gln Met Thr Arg Asp Phe Gly Gln Ala
            355                 360                 365 cag acc gct ctg gaa gct ttc gca gaa agc ctg taa                      1140
Gln Thr Ala Leu Glu Ala Phe Ala Glu Ser Leu
        370                 375

<210> SEQ ID NO 28
<211> LENGTH: 379
<212> TYPE: PRT
<213> ORGANISM: Acidaminococcus fermentans

<400> SEQUENCE: 28

Met Ala Ile Ser Ala Leu Ile Glu Glu Phe Gln Lys Val Ser Ala Ser
1               5                   10                  15

Pro Lys Thr Met Leu Ala Lys Tyr Lys Ala Gln Gly Lys Lys Ala Ile
                20                  25                  30

Gly Cys Leu Pro Tyr Tyr Val Pro Glu Glu Leu Val Tyr Ala Ala Gly
            35                  40                  45

Met Val Pro Met Gly Val Trp Gly Cys Asn Gly Lys Gln Glu Val Arg
        50                  55                  60

Ser Lys Glu Tyr Cys Ala Ser Phe Tyr Cys Thr Ile Ala Gln Gln Ser
65                  70                  75                  80

Leu Glu Met Leu Leu Asp Gly Thr Leu Asp Gly Leu Asp Gly Ile Ile
                85                  90                  95

Thr Pro Val Leu Cys Asp Thr Leu Arg Pro Met Ser Gln Asn Phe Lys
                100                 105                 110

Val Ala Met Lys Asp Lys Met Pro Val Ile Phe Leu Ala His Pro Gln
            115                 120                 125

Val Arg Gln Asn Ala Ala Gly Lys Gln Phe Thr Tyr Asp Ala Tyr Ser
        130                 135                 140

Glu Val Lys Gly His Leu Glu Glu Ile Cys Gly His Glu Ile Thr Asn
145                 150                 155                 160

Asp Ala Ile Leu Asp Ala Ile Lys Val Tyr Asn Lys Ser Arg Ala Ala
                165                 170                 175
```

```
Arg Arg Glu Phe Cys Lys Leu Ala Asn Glu His Pro Asp Leu Ile Pro
            180                 185                 190

Ala Ser Val Arg Ala Thr Val Leu Arg Ala Ala Tyr Phe Met Leu Lys
        195                 200                 205

Asp Glu Tyr Thr Glu Lys Leu Glu Glu Leu Asn Lys Glu Leu Ala Ala
210                 215                 220

Ala Pro Ala Gly Lys Phe Asp Gly His Lys Val Val Ser Gly Ile
225                 230                 235                 240

Ile Tyr Asn Thr Pro Gly Ile Leu Lys Ala Met Asp Asp Asn Lys Leu
                245                 250                 255

Ala Ile Ala Ala Asp Asp Cys Ala Tyr Glu Ser Arg Ser Phe Ala Val
            260                 265                 270

Asp Ala Pro Glu Asp Leu Asp Asn Gly Leu His Ala Leu Ala Val Gln
        275                 280                 285

Phe Ser Lys Gln Lys Asn Asp Val Leu Leu Tyr Asp Pro Glu Phe Ala
    290                 295                 300

Lys Asn Thr Arg Ser Glu His Val Gly Asn Leu Val Lys Glu Ser Gly
305                 310                 315                 320

Ala Glu Gly Leu Ile Val Phe Met Met Gln Phe Cys Asp Pro Glu Glu
                325                 330                 335

Met Glu Tyr Pro Asp Leu Lys Lys Ala Leu Asp Ala His His Ile Pro
            340                 345                 350

His Val Lys Ile Gly Val Asp Gln Met Thr Arg Asp Phe Gly Gln Ala
        355                 360                 365

Gln Thr Ala Leu Glu Ala Phe Ala Glu Ser Leu
    370                 375

<210> SEQ ID NO 29
<211> LENGTH: 1329
<212> TYPE: DNA
<213> ORGANISM: Fusobacterium nucleatum
<220> FEATURE:
<221> NAME/KEY: CDS
<222> LOCATION: (1)..(1329)

<400> SEQUENCE: 29 atg gct gga aaa atg gaa aaa tta cct aat aaa aaa cct aga cca ata      48
Met Ala Gly Lys Met Glu Lys Leu Pro Asn Lys Lys Pro Arg Pro Ile
1               5                  10                  15 gaa gga cat aaa cct gct gcg gct ata tta aga ggt gtt gtt gat aaa      96
Glu Gly His Lys Pro Ala Ala Ala Ile Leu Arg Gly Val Val Asp Lys
                20                  25                  30 gtt tat gca aat gct tgg gaa gca aaa aag aga gga gaa tta gtt gga     144
Val Tyr Ala Asn Ala Trp Glu Ala Lys Lys Arg Gly Glu Leu Val Gly
            35                  40                  45 tgg agt tca tct aaa ttc cct att gaa ctt gct aag gca ttt gac tta     192
Trp Ser Ser Ser Lys Phe Pro Ile Glu Leu Ala Lys Ala Phe Asp Leu
    50                  55                  60 aat gtt gtg tat cct gaa aat cat gct gca tca aca gca gct aaa aaa     240
Asn Val Val Tyr Pro Glu Asn His Ala Ala Ser Thr Ala Ala Lys Lys
65                  70                  75                  80 gat gga tta aga ctt tgt caa gct gcg gaa gat atg gga tat gac aat     288
Asp Gly Leu Arg Leu Cys Gln Ala Ala Glu Asp Met Gly Tyr Asp Asn
                85                  90                  95 gat att tgt gga tat gca aga atc agc tta gct tat gct gct ggt gaa     336
Asp Ile Cys Gly Tyr Ala Arg Ile Ser Leu Ala Tyr Ala Ala Gly Glu
                100                 105                 110
```

| | | |
|---|---|---|
| cca aca gat gca aga aga atg cca caa cca gac ttc tta cta tgt tgt<br>Pro Thr Asp Ala Arg Arg Met Pro Gln Pro Asp Phe Leu Leu Cys Cys<br>115                    120                    125 | | 384 |
| aat aac atc tgt aat atg atg act aaa tgg tat gaa aat ata gca aga<br>Asn Asn Ile Cys Asn Met Met Thr Lys Trp Tyr Glu Asn Ile Ala Arg<br>130                    135                    140 | | 432 |
| ata cat aat att cca tta ata atg ata gat ata cca ttc tca aat aca<br>Ile His Asn Ile Pro Leu Ile Met Ile Asp Ile Pro Phe Ser Asn Thr<br>145                    150                    155                    160 | | 480 |
| gta gac aca cca gaa gaa aaa gtt gat tat tta ata gga caa ttt gat<br>Val Asp Thr Pro Glu Glu Lys Val Asp Tyr Leu Ile Gly Gln Phe Asp<br>                  165                    170                    175 | | 528 |
| cat gct att aaa caa tta gaa gaa tta aca gga aag aaa ttt gat gaa<br>His Ala Ile Lys Gln Leu Glu Glu Leu Thr Gly Lys Lys Phe Asp Glu<br>                  180                    185                    190 | | 576 |
| aaa aaa ttt gaa gat gct tgt gca aga gca aat aga act gct gct gct<br>Lys Lys Phe Glu Asp Ala Cys Ala Arg Ala Asn Arg Thr Ala Ala Ala<br>195                    200                    205 | | 624 |
| tgg tta aaa tct tgt aaa tat atg gga tat aaa cca tct cca tta agt<br>Trp Leu Lys Ser Cys Lys Tyr Met Gly Tyr Lys Pro Ser Pro Leu Ser<br>210                    215                    220 | | 672 |
| gga ttt gat tta ttt aac cat atg gca gac att gtt gca gca aga tgt<br>Gly Phe Asp Leu Phe Asn His Met Ala Asp Ile Val Ala Ala Arg Cys<br>225                    230                    235                    240 | | 720 |
| gat gaa gaa gct gct atg gga ttt gaa tta ctt gca gat gaa ttt gaa<br>Asp Glu Glu Ala Ala Met Gly Phe Glu Leu Leu Ala Asp Glu Phe Glu<br>                  245                    250                    255 | | 768 |
| caa tct ata aaa gaa gga aca tca act tgg gaa tat cca gaa gaa cac<br>Gln Ser Ile Lys Glu Gly Thr Ser Thr Trp Glu Tyr Pro Glu Glu His<br>                  260                    265                    270 | | 816 |
| aga atc tta ttt gaa gga att cct tgt tgg cca gga tta aaa cca tta<br>Arg Ile Leu Phe Glu Gly Ile Pro Cys Trp Pro Gly Leu Lys Pro Leu<br>275                    280                    285 | | 864 |
| ttt gaa cct tta aaa gat aat gga gta aat gtt act gca gtt gtt tat<br>Phe Glu Pro Leu Lys Asp Asn Gly Val Asn Val Thr Ala Val Val Tyr<br>290                    295                    300 | | 912 |
| gca cca gca ttc gga ttt aga tat aac aat gta aga gaa atg gca gca<br>Ala Pro Ala Phe Gly Phe Arg Tyr Asn Asn Val Arg Glu Met Ala Ala<br>305                    310                    315                    320 | | 960 |
| gca tat tgt aaa gca cct tgt tct gta tgt ata gaa act ggt gtt gaa<br>Ala Tyr Cys Lys Ala Pro Cys Ser Val Cys Ile Glu Thr Gly Val Glu<br>                  325                    330                    335 | | 1008 |
| tgg aga gaa act atg gct aaa gaa aat ggt ata agt gga gca ctt gta<br>Trp Arg Glu Thr Met Ala Lys Glu Asn Gly Ile Ser Gly Ala Leu Val<br>                  340                    345                    350 | | 1056 |
| aac tat aac cgt agt tgt aaa cct tgg agt ggt gca atg cct gaa ata<br>Asn Tyr Asn Arg Ser Cys Lys Pro Trp Ser Gly Ala Met Pro Glu Ile<br>355                      360                    365 | | 1104 |
| gaa aga aga tgg aaa gaa gat tta gga atc cca gtt gtt cac ttt gat<br>Glu Arg Arg Trp Lys Glu Asp Leu Gly Ile Pro Val Val His Phe Asp<br>370                    375                    380 | | 1152 |
| gga gac caa gct gat gaa aga aac ttc tca aca gaa caa tat aat aca<br>Gly Asp Gln Ala Asp Glu Arg Asn Phe Ser Thr Glu Gln Tyr Asn Thr<br>385                    390                    395                    400 | | 1200 |
| aga gta caa ggg ctt gtt gaa ata atg caa gaa aga aaa gaa gaa aaa<br>Arg Val Gln Gly Leu Val Glu Ile Met Gln Glu Arg Lys Glu Glu Lys<br>                  405                    410                    415 | | 1248 |
| tta gca aaa ggt gaa gaa gtt tac act aac ttt gaa aac act aaa gaa<br>Leu Ala Lys Gly Glu Glu Val Tyr Thr Asn Phe Glu Asn Thr Lys Glu<br>420                    425                    430 | | 1296 |

```
act gac tgg tct aaa gaa aca ata aaa cat taa                    1329
Thr Asp Trp Ser Lys Glu Thr Ile Lys His
        435                 440

<210> SEQ ID NO 30
<211> LENGTH: 442
<212> TYPE: PRT
<213> ORGANISM: Fusobacterium nucleatum

<400> SEQUENCE: 30

Met Ala Gly Lys Met Glu Lys Leu Pro Asn Lys Lys Pro Arg Pro Ile
1               5                   10                  15

Glu Gly His Lys Pro Ala Ala Ile Leu Arg Gly Val Val Asp Lys
                20                  25                  30

Val Tyr Ala Asn Ala Trp Glu Ala Lys Lys Arg Gly Glu Leu Val Gly
            35                  40                  45

Trp Ser Ser Lys Phe Pro Ile Glu Leu Ala Lys Ala Phe Asp Leu
        50                  55                  60

Asn Val Val Tyr Pro Glu Asn His Ala Ala Ser Thr Ala Ala Lys Lys
65                  70                  75                  80

Asp Gly Leu Arg Leu Cys Gln Ala Ala Glu Asp Met Gly Tyr Asp Asn
                85                  90                  95

Asp Ile Cys Gly Tyr Ala Arg Ile Ser Leu Ala Tyr Ala Ala Gly Glu
            100                 105                 110

Pro Thr Asp Ala Arg Arg Met Pro Gln Pro Asp Phe Leu Leu Cys Cys
        115                 120                 125

Asn Asn Ile Cys Asn Met Met Thr Lys Trp Tyr Glu Asn Ile Ala Arg
130                 135                 140

Ile His Asn Ile Pro Leu Ile Met Ile Asp Ile Pro Phe Ser Asn Thr
145                 150                 155                 160

Val Asp Thr Pro Glu Glu Lys Val Asp Tyr Leu Ile Gly Gln Phe Asp
                165                 170                 175

His Ala Ile Lys Gln Leu Glu Glu Leu Thr Gly Lys Lys Phe Asp Glu
            180                 185                 190

Lys Lys Phe Glu Asp Ala Cys Ala Arg Ala Asn Arg Thr Ala Ala Ala
        195                 200                 205

Trp Leu Lys Ser Cys Lys Tyr Met Gly Tyr Lys Pro Ser Pro Leu Ser
210                 215                 220

Gly Phe Asp Leu Phe Asn His Met Ala Asp Ile Val Ala Ala Arg Cys
225                 230                 235                 240

Asp Glu Glu Ala Ala Met Gly Phe Glu Leu Leu Ala Asp Glu Phe Glu
                245                 250                 255

Gln Ser Ile Lys Glu Gly Thr Ser Thr Trp Glu Tyr Pro Glu Glu His
            260                 265                 270

Arg Ile Leu Phe Glu Gly Ile Pro Cys Trp Pro Gly Leu Lys Pro Leu
        275                 280                 285

Phe Glu Pro Leu Lys Asp Asn Gly Val Asn Val Thr Ala Val Val Tyr
290                 295                 300

Ala Pro Ala Phe Gly Phe Arg Tyr Asn Asn Val Arg Glu Met Ala Ala
305                 310                 315                 320

Ala Tyr Cys Lys Ala Pro Cys Ser Val Cys Ile Glu Thr Gly Val Glu
                325                 330                 335

Trp Arg Glu Thr Met Ala Lys Glu Asn Gly Ile Ser Gly Ala Leu Val
            340                 345                 350
```

```
Asn Tyr Asn Arg Ser Cys Lys Pro Trp Ser Gly Ala Met Pro Glu Ile
            355                 360                 365

Glu Arg Arg Trp Lys Glu Asp Leu Gly Ile Pro Val Val His Phe Asp
    370                 375                 380

Gly Asp Gln Ala Asp Glu Arg Asn Phe Ser Thr Glu Gln Tyr Asn Thr
385                 390                 395                 400

Arg Val Gln Gly Leu Val Glu Ile Met Gln Glu Arg Lys Glu Glu Lys
                405                 410                 415

Leu Ala Lys Gly Glu Glu Val Tyr Thr Asn Phe Glu Asn Thr Lys Glu
            420                 425                 430

Thr Asp Trp Ser Lys Glu Thr Ile Lys His
            435                 440

<210> SEQ ID NO 31
<211> LENGTH: 1149
<212> TYPE: DNA
<213> ORGANISM: Fusobacterium nucleatum
<220> FEATURE:
<221> NAME/KEY: CDS
<222> LOCATION: (1)..(1149)

<400> SEQUENCE: 31
```

| | | | | | | | | | | | | | | | | |
|---|---|---|---|---|---|---|---|---|---|---|---|---|---|---|---|---|
| atg | gct | gaa | att | aag | gaa | ttg | tta | gaa | caa | ttt | aaa | tac | tat | gca | gaa | 48 |
| Met | Ala | Glu | Ile | Lys | Glu | Leu | Leu | Glu | Gln | Phe | Lys | Tyr | Tyr | Ala | Glu | |
| 1 | | | | 5 | | | | | 10 | | | | | 15 | | |
| aat | cct | aga | aag | caa | ttg | gat | aaa | tat | ctt | gct | gaa | ggt | aag | aaa | gca | 96 |
| Asn | Pro | Arg | Lys | Gln | Leu | Asp | Lys | Tyr | Leu | Ala | Glu | Gly | Lys | Lys | Ala | |
| | | | 20 | | | | | 25 | | | | | 30 | | | |
| gtc | gga | ata | ttc | cct | tat | tat | gca | cca | gaa | gaa | ata | gtt | tat | gca | ggt | 144 |
| Val | Gly | Ile | Phe | Pro | Tyr | Tyr | Ala | Pro | Glu | Glu | Ile | Val | Tyr | Ala | Gly | |
| | | 35 | | | | | 40 | | | | | 45 | | | | |
| gga | atg | gtt | cca | ttt | ggt | gta | tgg | gga | gga | caa | gga | cct | att | gaa | aaa | 192 |
| Gly | Met | Val | Pro | Phe | Gly | Val | Trp | Gly | Gly | Gln | Gly | Pro | Ile | Glu | Lys | |
| | 50 | | | | | 55 | | | | | 60 | | | | | |
| gca | aag | gat | tat | ttc | cct | act | ttc | tac | tac | tca | ttg | gcc | tta | aga | tgt | 240 |
| Ala | Lys | Asp | Tyr | Phe | Pro | Thr | Phe | Tyr | Tyr | Ser | Leu | Ala | Leu | Arg | Cys | |
| 65 | | | | | 70 | | | | | 75 | | | | | 80 | |
| tta | gaa | atg | gct | tta | gat | gga | act | tta | gat | ggt | cta | tct | gca | tca | atg | 288 |
| Leu | Glu | Met | Ala | Leu | Asp | Gly | Thr | Leu | Asp | Gly | Leu | Ser | Ala | Ser | Met | |
| | | | | 85 | | | | | 90 | | | | | 95 | | |
| gtt | act | aca | tta | gac | gat | aca | tta | aga | cca | ttt | tca | caa | aac | tat | aaa | 336 |
| Val | Thr | Thr | Leu | Asp | Asp | Thr | Leu | Arg | Pro | Phe | Ser | Gln | Asn | Tyr | Lys | |
| | | | 100 | | | | | 105 | | | | | 110 | | | |
| gta | agt | gca | gga | aga | aaa | ata | cct | atg | gta | ttt | tta | aat | cat | gga | caa | 384 |
| Val | Ser | Ala | Gly | Arg | Lys | Ile | Pro | Met | Val | Phe | Leu | Asn | His | Gly | Gln | |
| | | 115 | | | | | 120 | | | | | 125 | | | | |
| cat | aga | aaa | gaa | gaa | ttt | ggt | aaa | aag | tat | aat | gca | aaa | att | ttc | aat | 432 |
| His | Arg | Lys | Glu | Glu | Phe | Gly | Lys | Lys | Tyr | Asn | Ala | Lys | Ile | Phe | Asn | |
| | 130 | | | | | 135 | | | | | 140 | | | | | |
| aat | gct | aaa | gaa | gaa | tta | gaa | aaa | att | tgt | gat | gta | aaa | att | act | gat | 480 |
| Asn | Ala | Lys | Glu | Glu | Leu | Glu | Lys | Ile | Cys | Asp | Val | Lys | Ile | Thr | Asp | |
| 145 | | | | | 150 | | | | | 155 | | | | | 160 | |
| gaa | aac | ttg | aaa | aaa | gca | ttt | aaa | gtt | tat | aat | gaa | aat | aga | gaa | gaa | 528 |
| Glu | Asn | Leu | Lys | Lys | Ala | Phe | Lys | Val | Tyr | Asn | Glu | Asn | Arg | Glu | Glu | |
| | | | | 165 | | | | | 170 | | | | | 175 | | |
| aaa | aga | aaa | ttt | ata | aaa | ctt | gct | gct | aaa | cac | cca | caa | agt | ata | aaa | 576 |
| Lys | Arg | Lys | Phe | Ile | Lys | Leu | Ala | Ala | Lys | His | Pro | Gln | Ser | Ile | Lys | |
| | | | 180 | | | | | 185 | | | | | 190 | | | |
| gca | tct | gat | aga | tca | aat | gtc | tta | aag | agt | tca | tat | ttt | atg | tta | aaa | 624 |
| Ala | Ser | Asp | Arg | Ser | Asn | Val | Leu | Lys | Ser | Ser | Tyr | Phe | Met | Leu | Lys | |

```
                       195                   200                   205
gat gaa cat aca gat tta tta aga caa tta aat caa aaa tta gaa gct       672
Asp Glu His Thr Asp Leu Leu Arg Gln Leu Asn Gln Lys Leu Glu Ala
    210                 215                 220 ctt cca gaa gaa caa tgg gat gga gta aga gtt gtt aca agt gga att       720
Leu Pro Glu Glu Gln Trp Asp Gly Val Arg Val Val Thr Ser Gly Ile
225                 230                 235                 240 atc act gac aac cca gga ctt tta gaa gta ttt gat aac tat aaa gta       768
Ile Thr Asp Asn Pro Gly Leu Leu Glu Val Phe Asp Asn Tyr Lys Val
                245                 250                 255 tgt gta gtt gca gat gat gtg gct cat gaa tca aga gca ttg aaa gtt       816
Cys Val Val Ala Asp Asp Val Ala His Glu Ser Arg Ala Leu Lys Val
            260                 265                 270 gat ata gat tta tca ata gaa gat cca atg tta gct ctt gct gat caa       864
Asp Ile Asp Leu Ser Ile Glu Asp Pro Met Leu Ala Leu Ala Asp Gln
        275                 280                 285 ttt gct cgt atg gat gaa gat cct tta ctt tat gat cct gat att att       912
Phe Ala Arg Met Asp Glu Asp Pro Leu Leu Tyr Asp Pro Asp Ile Ile
    290                 295                 300 aaa aga cca aaa tat gta ttg gat tta gta aaa gaa aat aat gca gat       960
Lys Arg Pro Lys Tyr Val Leu Asp Leu Val Lys Glu Asn Asn Ala Asp
305                 310                 315                 320 ggt tgc ttg tta ttt atg atg aat ttc aat gat act gaa gaa atg gaa      1008
Gly Cys Leu Leu Phe Met Met Asn Phe Asn Asp Thr Glu Glu Met Glu
                325                 330                 335 tat cca tca tta aaa caa gca ttt gat gaa gca aaa gtt cca tta att      1056
Tyr Pro Ser Leu Lys Gln Ala Phe Asp Glu Ala Lys Val Pro Leu Ile
            340                 345                 350 aaa atg gga tat gat caa caa atg gtg gac ttt gga caa gtt aag act      1104
Lys Met Gly Tyr Asp Gln Gln Met Val Asp Phe Gly Gln Val Lys Thr
        355                 360                 365 caa ctt gaa aca ttt aat gaa tta gta caa tta agt aga ttc tag           1149
Gln Leu Glu Thr Phe Asn Glu Leu Val Gln Leu Ser Arg Phe
    370                 375                 380
```

<210> SEQ ID NO 32
<211> LENGTH: 382
<212> TYPE: PRT
<213> ORGANISM: Fusobacterium nucleatum

<400> SEQUENCE: 32

```
Met Ala Glu Ile Lys Glu Leu Leu Glu Gln Phe Lys Tyr Tyr Ala Glu
1               5                   10                  15

Asn Pro Arg Lys Gln Leu Asp Lys Tyr Leu Ala Glu Gly Lys Lys Ala
            20                  25                  30

Val Gly Ile Phe Pro Tyr Tyr Ala Pro Glu Glu Ile Val Tyr Ala Gly
        35                  40                  45

Gly Met Val Pro Phe Gly Val Trp Gly Gly Gln Gly Pro Ile Glu Lys
    50                  55                  60

Ala Lys Asp Tyr Phe Pro Thr Tyr Tyr Ser Leu Ala Leu Arg Cys
65                  70                  75                  80

Leu Glu Met Ala Leu Asp Gly Thr Leu Asp Gly Leu Ser Ala Ser Met
                85                  90                  95

Val Thr Thr Leu Asp Asp Thr Leu Arg Pro Phe Ser Gln Asn Tyr Lys
            100                 105                 110

Val Ser Ala Gly Arg Lys Ile Pro Met Val Phe Leu Asn His Gly Gln
        115                 120                 125

His Arg Lys Glu Glu Phe Gly Lys Lys Tyr Asn Ala Lys Ile Phe Asn
```

```
        130                 135                 140
Asn Ala Lys Glu Glu Leu Glu Lys Ile Cys Asp Val Lys Ile Thr Asp
145                 150                 155                 160

Glu Asn Leu Lys Lys Ala Phe Lys Val Tyr Asn Glu Asn Arg Glu Glu
                165                 170                 175

Lys Arg Lys Phe Ile Lys Leu Ala Ala Lys His Pro Gln Ser Ile Lys
            180                 185                 190

Ala Ser Asp Arg Ser Asn Val Leu Lys Ser Ser Tyr Phe Met Leu Lys
        195                 200                 205

Asp Glu His Thr Asp Leu Leu Arg Gln Leu Asn Gln Lys Leu Glu Ala
    210                 215                 220

Leu Pro Glu Glu Gln Trp Asp Gly Val Arg Val Thr Ser Gly Ile
225                 230                 235                 240

Ile Thr Asp Asn Pro Gly Leu Leu Glu Val Phe Asp Asn Tyr Lys Val
                245                 250                 255

Cys Val Val Ala Asp Asp Val Ala His Glu Ser Arg Ala Leu Lys Val
            260                 265                 270

Asp Ile Asp Leu Ser Ile Glu Asp Pro Met Leu Ala Leu Ala Asp Gln
        275                 280                 285

Phe Ala Arg Met Asp Glu Asp Pro Leu Leu Tyr Asp Pro Asp Ile Ile
    290                 295                 300

Lys Arg Pro Lys Tyr Val Leu Asp Leu Val Lys Glu Asn Asn Ala Asp
305                 310                 315                 320

Gly Cys Leu Leu Phe Met Met Asn Phe Asn Asp Thr Glu Glu Met Glu
                325                 330                 335

Tyr Pro Ser Leu Lys Gln Ala Phe Asp Glu Ala Lys Val Pro Leu Ile
            340                 345                 350

Lys Met Gly Tyr Asp Gln Met Val Asp Phe Gly Gln Val Lys Thr
        355                 360                 365

Gln Leu Glu Thr Phe Asn Glu Leu Val Gln Leu Ser Arg Phe
    370                 375                 380

<210> SEQ ID NO 33
<211> LENGTH: 594
<212> TYPE: DNA
<213> ORGANISM: Fusobacterium nucleatum
<220> FEATURE:
<221> NAME/KEY: CDS
<222> LOCATION: (1)..(594)

<400> SEQUENCE: 33 atg gat caa aat ata tgg gaa tat gat gat ttt att ttt aaa ggt gat    48
Met Asp Gln Asn Ile Trp Glu Tyr Asp Asp Phe Ile Phe Lys Gly Asp
1               5                  10                  15 gaa cta aaa gga atg act caa aaa ggt aag gat aaa gta aaa gtt gaa    96
Glu Leu Lys Gly Met Thr Gln Lys Gly Lys Asp Lys Val Lys Val Glu
            20                  25                  30 ggt aaa act gat tta gta att cct gaa tta act cct gat gga cta cct   144
Gly Lys Thr Asp Leu Val Ile Pro Glu Leu Thr Pro Asp Gly Leu Pro
        35                  40                  45 tta aaa aag att gca gac aat gct ttt tat aga aga gga tta act tca   192
Leu Lys Lys Ile Ala Asp Asn Ala Phe Tyr Arg Arg Gly Leu Thr Ser
    50                  55                  60 gta ata att cct agt aca gtg gaa agt att ggt tat gat gct ttt gga   240
Val Ile Ile Pro Ser Thr Val Glu Ser Ile Gly Tyr Asp Ala Phe Gly
65                  70                  75                  80 gtt tgt aaa tta aaa gaa gtt aaa tta cca gaa gca tta gta aat ata   288
```

```
                Val Cys Lys Leu Lys Glu Val Lys Leu Pro Glu Ala Leu Val Asn Ile
                                85                  90                  95 gaa ggt ttt gct ttt tat aga aat aaa ttg act aag gtt gaa ttt gga        336
Glu Gly Phe Ala Phe Tyr Arg Asn Lys Leu Thr Lys Val Glu Phe Gly
            100                 105                 110 agt aaa gta aag aga tta gaa cca agt tca ttt gct atg aat gaa ctt        384
Ser Lys Val Lys Arg Leu Glu Pro Ser Ser Phe Ala Met Asn Glu Leu
            115                 120                 125 tca gaa tta aat tta cct gaa act gta gaa tac ata gga gca tca gct        432
Ser Glu Leu Asn Leu Pro Glu Thr Val Glu Tyr Ile Gly Ala Ser Ala
        130                 135                 140 ttc tat aaa aat tct tta gaa aca gta agt ttt cca aaa tct gtt act        480
Phe Tyr Lys Asn Ser Leu Glu Thr Val Ser Phe Pro Lys Ser Val Thr
145                 150                 155                 160 aaa ata gat atg tat gct ttt aga aag aat aat atc cat aag gta gaa        528
Lys Ile Asp Met Tyr Ala Phe Arg Lys Asn Asn Ile His Lys Val Glu
                165                 170                 175 gta gca aat tct gtt gat tta cat aaa ttt gct ttt gaa act ttt aca        576
Val Ala Asn Ser Val Asp Leu His Lys Phe Ala Phe Glu Thr Phe Thr
            180                 185                 190 gct gtt gaa aga ttt tag                                                594
Ala Val Glu Arg Phe
            195

<210> SEQ ID NO 34
<211> LENGTH: 197
<212> TYPE: PRT
<213> ORGANISM: Fusobacterium nucleatum

<400> SEQUENCE: 34

Met Asp Gln Asn Ile Trp Glu Tyr Asp Asp Phe Ile Phe Lys Gly Asp
1               5                   10                  15

Glu Leu Lys Gly Met Thr Gln Lys Gly Lys Asp Lys Val Lys Val Glu
                20                  25                  30

Gly Lys Thr Asp Leu Val Ile Pro Glu Leu Thr Pro Asp Gly Leu Pro
            35                  40                  45

Leu Lys Lys Ile Ala Asp Asn Ala Phe Tyr Arg Arg Gly Leu Thr Ser
        50                  55                  60

Val Ile Ile Pro Ser Thr Val Glu Ser Ile Gly Tyr Asp Ala Phe Gly
65                  70                  75                  80

Val Cys Lys Leu Lys Glu Val Lys Leu Pro Glu Ala Leu Val Asn Ile
                85                  90                  95

Glu Gly Phe Ala Phe Tyr Arg Asn Lys Leu Thr Lys Val Glu Phe Gly
            100                 105                 110

Ser Lys Val Lys Arg Leu Glu Pro Ser Ser Phe Ala Met Asn Glu Leu
        115                 120                 125

Ser Glu Leu Asn Leu Pro Glu Thr Val Glu Tyr Ile Gly Ala Ser Ala
    130                 135                 140

Phe Tyr Lys Asn Ser Leu Glu Thr Val Ser Phe Pro Lys Ser Val Thr
145                 150                 155                 160

Lys Ile Asp Met Tyr Ala Phe Arg Lys Asn Asn Ile His Lys Val Glu
                165                 170                 175

Val Ala Asn Ser Val Asp Leu His Lys Phe Ala Phe Glu Thr Phe Thr
            180                 185                 190

Ala Val Glu Arg Phe
        195
```

<210> SEQ ID NO 35
<211> LENGTH: 804
<212> TYPE: DNA
<213> ORGANISM: Clostridium symbiosum
<220> FEATURE:
<221> NAME/KEY: CDS
<222> LOCATION: (1)..(804)
<220> FEATURE:
<221> NAME/KEY: Misc_Feature
<222> LOCATION: (11)..(11)
<223> OTHER INFORMATION: Xaa is Val

<400> SEQUENCE: 35

```
atg agc gga att tat act tta ggt atc gac gts ggt tcc aca gcc tcc      48
Met Ser Gly Ile Tyr Thr Leu Gly Ile Asp Xaa Gly Ser Thr Ala Ser
1               5                   10                  15 aag tgc atc gtt tta aaa gat ggc aaa gag att gtg gcc aaa tca ctg      96
Lys Cys Ile Val Leu Lys Asp Gly Lys Glu Ile Val Ala Lys Ser Leu
                20                  25                  30 ata gat gta ggc gca ggt acc agt gga ccg cag cgc gcg att gaa gcc     144
Ile Asp Val Gly Ala Gly Thr Ser Gly Pro Gln Arg Ala Ile Glu Ala
            35                  40                  45 gtg ctc aac gag gca ggc atg aag aag gaa gac atg gca tat acg ctg     192
Val Leu Asn Glu Ala Gly Met Lys Lys Glu Asp Met Ala Tyr Thr Leu
    50                  55                  60 gca aca ggc tac ggc cgt acc tct ttg atg gat ggc att gcc gat aaa     240
Ala Thr Gly Tyr Gly Arg Thr Ser Leu Met Asp Gly Ile Ala Asp Lys
65                  70                  75                  80 cag atg agc gag ctt tcc tgc cat gcc aag ggt gca act ttt ctg ttt     288
Gln Met Ser Glu Leu Ser Cys His Ala Lys Gly Ala Thr Phe Leu Phe
                85                  90                  95 cca aat gtc cac act gtc att gat att ggt gga cag gac gta aaa gtt     336
Pro Asn Val His Thr Val Ile Asp Ile Gly Gly Gln Asp Val Lys Val
            100                 105                 110 ctg cat ata gat aat ggt gca atg acc aat ttc cag atg aat gac aag     384
Leu His Ile Asp Asn Gly Ala Met Thr Asn Phe Gln Met Asn Asp Lys
    115                 120                 125 tgt gcg gca gga acg gga cgg ttc ctg gat gtt atg gcg cgt gtt ctg     432
Cys Ala Ala Gly Thr Gly Arg Phe Leu Asp Val Met Ala Arg Val Leu
130                 135                 140 gaa gta aag gtt gaa gat ctg gga aga ctc ggc gcc atg tcc cgg aag     480
Glu Val Lys Val Glu Asp Leu Gly Arg Leu Gly Ala Met Ser Arg Lys
145                 150                 155                 160 aaa gtg gga atc agt tcc act tgt acc gtt ttc gcc gag agt gag gtt     528
Lys Val Gly Ile Ser Ser Thr Cys Thr Val Phe Ala Glu Ser Glu Val
                165                 170                 175 ata agc cag ctg gca atg gga acc gat aaa tgt gat att atc gac gga     576
Ile Ser Gln Leu Ala Met Gly Thr Asp Lys Cys Asp Ile Ile Asp Gly
            180                 185                 190 atc cat cgc tcg gtg gct cat cgt gtc aca ggg ctt gcc cac cgt atc     624
Ile His Arg Ser Val Ala His Arg Val Thr Gly Leu Ala His Arg Ile
    195                 200                 205 ggt gtg gta ccg gat gtc gtt atg acc ggc gga gtg gct cag aat gaa     672
Gly Val Val Pro Asp Val Val Met Thr Gly Gly Val Ala Gln Asn Glu
210                 215                 220 ggc gtt gta aag gcg ctt cag gat gag ctg gga tgt ccg atc aac act     720
Gly Val Val Lys Ala Leu Gln Asp Glu Leu Gly Cys Pro Ile Asn Thr
225                 230                 235                 240 tcc ccg ctg aca cag tat aat ggc gcg ctt ggc gcc gcc ctt ctt gca     768
Ser Pro Leu Thr Gln Tyr Asn Gly Ala Leu Gly Ala Ala Leu Leu Ala
                245                 250                 255 tgg cag gcg gcc agc cgc cgt caa agc aat tca tag                     804
Trp Gln Ala Ala Ser Arg Arg Gln Ser Asn Ser
```

Trp Gln Ala Ala Ser Arg Arg Gln Ser Asn Ser
                260                 265

<210> SEQ ID NO 36
<211> LENGTH: 267
<212> TYPE: PRT
<213> ORGANISM: Clostridium symbiosum
<220> FEATURE:
<221> NAME/KEY: misc_feature
<222> LOCATION: (11)..(11)
<223> OTHER INFORMATION: The 'Xaa' at location 11 stands for Val.

<400> SEQUENCE: 36

Met Ser Gly Ile Tyr Thr Leu Gly Ile Asp Xaa Gly Ser Thr Ala Ser
1               5                   10                  15

Lys Cys Ile Val Leu Lys Asp Gly Lys Glu Ile Val Ala Lys Ser Leu
            20                  25                  30

Ile Asp Val Gly Ala Gly Thr Ser Gly Pro Gln Arg Ala Ile Glu Ala
        35                  40                  45

Val Leu Asn Glu Ala Gly Met Lys Lys Glu Asp Met Ala Tyr Thr Leu
    50                  55                  60

Ala Thr Gly Tyr Gly Arg Thr Ser Leu Met Asp Gly Ile Ala Asp Lys
65                  70                  75                  80

Gln Met Ser Glu Leu Ser Cys His Ala Lys Gly Ala Thr Phe Leu Phe
                85                  90                  95

Pro Asn Val His Thr Val Ile Asp Ile Gly Gly Gln Asp Val Lys Val
            100                 105                 110

Leu His Ile Asp Asn Gly Ala Met Thr Asn Phe Gln Met Asn Asp Lys
        115                 120                 125

Cys Ala Ala Gly Thr Gly Arg Phe Leu Asp Val Met Ala Arg Val Leu
    130                 135                 140

Glu Val Lys Val Glu Asp Leu Gly Arg Leu Gly Ala Met Ser Arg Lys
145                 150                 155                 160

Lys Val Gly Ile Ser Ser Thr Cys Thr Val Phe Ala Glu Ser Glu Val
                165                 170                 175

Ile Ser Gln Leu Ala Met Gly Thr Asp Lys Cys Asp Ile Ile Asp Gly
            180                 185                 190

Ile His Arg Ser Val Ala His Arg Val Thr Gly Leu Ala His Arg Ile
        195                 200                 205

Gly Val Val Pro Asp Val Val Met Thr Gly Gly Val Ala Gln Asn Glu
    210                 215                 220

Gly Val Val Lys Ala Leu Gln Asp Glu Leu Gly Cys Pro Ile Asn Thr
225                 230                 235                 240

Ser Pro Leu Thr Gln Tyr Asn Gly Ala Leu Gly Ala Ala Leu Leu Ala
                245                 250                 255

Trp Gln Ala Ala Ser Arg Arg Gln Ser Asn Ser
                260                 265

<210> SEQ ID NO 37
<211> LENGTH: 798
<212> TYPE: DNA
<213> ORGANISM: Fusobacterium nucleatum
<220> FEATURE:
<221> NAME/KEY: CDS
<222> LOCATION: (1)..(798)

<400> SEQUENCE: 37 atg agt aat gtt ttt act atg gga ata gat gtt gga tca aca gca tct      48
Met Ser Asn Val Phe Thr Met Gly Ile Asp Val Gly Ser Thr Ala Ser

```
                1               5                   10                  15
        aaa tgt gta ata tta aaa gat ggt aaa gaa atc gtt gca aaa tct gtt      96
        Lys Cys Val Ile Leu Lys Asp Gly Lys Glu Ile Val Ala Lys Ser Val
                        20                  25                  30 ata tca gta ggg aca gga acc agt gga cca gct aga gct atg aaa gaa     144
        Ile Ser Val Gly Thr Gly Thr Ser Gly Pro Ala Arg Ala Met Lys Glu
                        35                  40                  45 gca tta gag caa att gga ttg agt tct gtt aat gag ctt caa gga gca     192
        Ala Leu Glu Gln Ile Gly Leu Ser Ser Val Asn Glu Leu Gln Gly Ala
                    50                  55                  60 gtt gca act ggt tat gga aga aac tca tta gca gaa gtg cca gct caa     240
        Val Ala Thr Gly Tyr Gly Arg Asn Ser Leu Ala Glu Val Pro Ala Gln
        65                  70                  75                  80 atg tct gaa tta tct tgt cat gcg aaa gga gca tat ttt cta ttt cca     288
        Met Ser Glu Leu Ser Cys His Ala Lys Gly Ala Tyr Phe Leu Phe Pro
                        85                  90                  95 aat gtt cac tca att ata gat att ggt ggt caa gat tca aaa gca ttg     336
        Asn Val His Ser Ile Ile Asp Ile Gly Gly Gln Asp Ser Lys Ala Leu
                        100                 105                 110 aaa att gga gac aat gga atg ctt gaa aat ttt gtt atg aat gat aaa     384
        Lys Ile Gly Asp Asn Gly Met Leu Glu Asn Phe Val Met Asn Asp Lys
                        115                 120                 125 tgt gca gca gga aca gga aga ttt tta gat gta att gca aag gtt tta     432
        Cys Ala Ala Gly Thr Gly Arg Phe Leu Asp Val Ile Ala Lys Val Leu
        130                 135                 140 gaa gta gac tta gaa gac tta gaa aaa tta gat gaa aaa tct act gtt     480
        Glu Val Asp Leu Glu Asp Leu Glu Lys Leu Asp Glu Lys Ser Thr Val
        145                 150                 155                 160 gat gta gca ata agt tcg act tgt act gta ttt gca gaa tca gaa gta     528
        Asp Val Ala Ile Ser Ser Thr Cys Thr Val Phe Ala Glu Ser Glu Val
                        165                 170                 175 att tcg caa ctt gca aaa gga aca aaa att gaa gat ata gta aaa ggt     576
        Ile Ser Gln Leu Ala Lys Gly Thr Lys Ile Glu Asp Ile Val Lys Gly
                        180                 185                 190 att cac act gct ata gct agc cgt gtt gga agc ttg gca aaa aga ata     624
        Ile His Thr Ala Ile Ala Ser Arg Val Gly Ser Leu Ala Lys Arg Ile
                        195                 200                 205 ggt ata aaa gat gat gtt gtt atg act ggt gga gtt gca ctt aat aaa     672
        Gly Ile Lys Asp Asp Val Val Met Thr Gly Gly Val Ala Leu Asn Lys
        210                 215                 220 ggt atg gtt aga gcc ttg gaa aga aac tta ggt ttt aaa tta cat aca     720
        Gly Met Val Arg Ala Leu Glu Arg Asn Leu Gly Phe Lys Leu His Thr
        225                 230                 235                 240 aat gaa tac tgt caa tta aat ggg gca ata gga gca gca tta ttt gct     768
        Asn Glu Tyr Cys Gln Leu Asn Gly Ala Ile Gly Ala Ala Leu Phe Ala
                        245                 250                 255 tat caa aaa tat aca atg act cat caa taa                             798
        Tyr Gln Lys Tyr Thr Met Thr His Gln
                        260                 265

<210> SEQ ID NO 38
<211> LENGTH: 265
<212> TYPE: PRT
<213> ORGANISM: Fusobacterium nucleatum

<400> SEQUENCE: 38

Met Ser Asn Val Phe Thr Met Gly Ile Asp Val Gly Ser Thr Ala Ser
1               5                   10                  15

Lys Cys Val Ile Leu Lys Asp Gly Lys Glu Ile Val Ala Lys Ser Val
            20                  25                  30
```

Ile Ser Val Gly Thr Gly Thr Ser Gly Pro Ala Arg Ala Met Lys Glu
            35                  40                  45

Ala Leu Glu Gln Ile Gly Leu Ser Ser Val Asn Glu Leu Gln Gly Ala
        50                  55                  60

Val Ala Thr Gly Tyr Gly Arg Asn Ser Leu Ala Glu Val Pro Ala Gln
65                  70                  75                  80

Met Ser Glu Leu Ser Cys His Ala Lys Gly Ala Tyr Phe Leu Phe Pro
                85                  90                  95

Asn Val His Ser Ile Ile Asp Ile Gly Gly Gln Asp Ser Lys Ala Leu
            100                 105                 110

Lys Ile Gly Asp Asn Gly Met Leu Glu Asn Phe Val Met Asn Asp Lys
            115                 120                 125

Cys Ala Ala Gly Thr Gly Arg Phe Leu Asp Val Ile Ala Lys Val Leu
            130                 135                 140

Glu Val Asp Leu Glu Asp Leu Glu Lys Leu Asp Glu Lys Ser Thr Val
145                 150                 155                 160

Asp Val Ala Ile Ser Ser Thr Cys Thr Val Phe Ala Glu Ser Glu Val
                165                 170                 175

Ile Ser Gln Leu Ala Lys Gly Thr Lys Ile Glu Asp Ile Val Lys Gly
            180                 185                 190

Ile His Thr Ala Ile Ala Ser Arg Val Gly Ser Leu Ala Lys Arg Ile
            195                 200                 205

Gly Ile Lys Asp Asp Val Val Met Thr Gly Gly Val Ala Leu Asn Lys
            210                 215                 220

Gly Met Val Arg Ala Leu Glu Arg Asn Leu Gly Phe Lys Leu His Thr
225                 230                 235                 240

Asn Glu Tyr Cys Gln Leu Asn Gly Ala Ile Gly Ala Ala Leu Phe Ala
                245                 250                 255

Tyr Gln Lys Tyr Thr Met Thr His Gln
            260                 265

<210> SEQ ID NO 39
<211> LENGTH: 45
<212> TYPE: DNA
<213> ORGANISM: Artificial Sequence
<220> FEATURE:
<223> OTHER INFORMATION: PCR Primer

<400> SEQUENCE: 39
atggtacata tgtgagtaaa gtaatgacgt taaaagacgc aatcg                45

<210> SEQ ID NO 40
<211> LENGTH: 37
<212> TYPE: DNA
<213> ORGANISM: Artificial Sequence
<220> FEATURE:
<223> OTHER INFORMATION: PCR Primer

<400> SEQUENCE: 40
atggtactcg agttattttg cttccgtggg gacctgg                         37

METHOD FOR THE PRODUCTION OF GLUTACONATE

RELATED APPLICATIONS

This application is a national stage application (under 35 U.S.C. §371) of PCT/EP2010/050475, filed Jan. 15, 2010, which claims benefit of European application 09150669.1, filed Jan. 15, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13111_00182_US. The size of the text file is 137 KB, and the text file was created on Jul. 11, 2011.

The present invention relates to a novel method for the biocatalytic production of unsaturated dicarboxylic acids by cultivating a recombinant microorganism co-expressing a glutaconate CoA-transferase and a 2-hydroxyglutaryl-CoA dehydratase system. The present invention also relates to corresponding recombinant hosts, recombinant vectors, expression cassettes and nucleic acids suitable for preparing such hosts as well as a method of preparing polymers, as for example polyamide or polyester copolymers, making use of said dicarboxylic acids as obtained by said biocatalytic production method.

BACKGROUND OF THE INVENTION

Glutaconic acid is an α,β-unsaturated C5-dicarboxylic acid (2-pentenedioic acid) that accumulates in individuals with glutaric acidemia type I (Hoffmann G F, Zschocke J (1999) *Glutaric aciduria type I: from clinical, biochemical and molecular diversity to successful therapy. J Inherit Metab Dis* 22:381-391). Glutaconic acid together with a diamine can polymerize to a polyamide related to Nylon®. The ideal material for biotechnological production of glutaconic acid would be glutamic acid, which can be produced by sugar fermentation. The chemical deamination of α-amino acids to α,β-unsaturated acids is very difficult. On the contrary, the strictly anaerobic bacteria *Acidaminococcus fermentans* and *Clostridium symbiosum* can easily deaminate glutamate via α-ketoglutarate, (R)-2-hydroxyglutarate, (R)-2-hydroxyglutaryl-CoA, and glutaconyl-CoA to (E)-glutaconate (Buckel W (2001b) *Unusual enzymes involved in five pathways of glutamate fermentation. Appl Microbiol Biotechnol* 57:263-273). *A. fermentans* and *C. symbiosum* are not suitable for the production of glutaconic acid because they decarboxylate glutaconyl-CoA to crotonyl-CoA. Genetic manipulation of these organisms has not been established yet. Thus, the genes coding for glutaconyl-CoA decarboxylase cannot be attenuated to a low level, whereas a complete deletion would deprive these organisms of the ability to produce ATP. Furthermore, the ultimate aim is the production of glutaconate not from glutamate but from glucose, on which *A. fermentans* and *C. symbiosum* are not able to grow.

The object of the present invention is therefore to provide a suitable method for the fermentative, biocatalytic production of glutaconic acid and related dicarboxylic acids or corresponding salts thereof.

SUMMARY OF THE INVENTION

Figure 1:
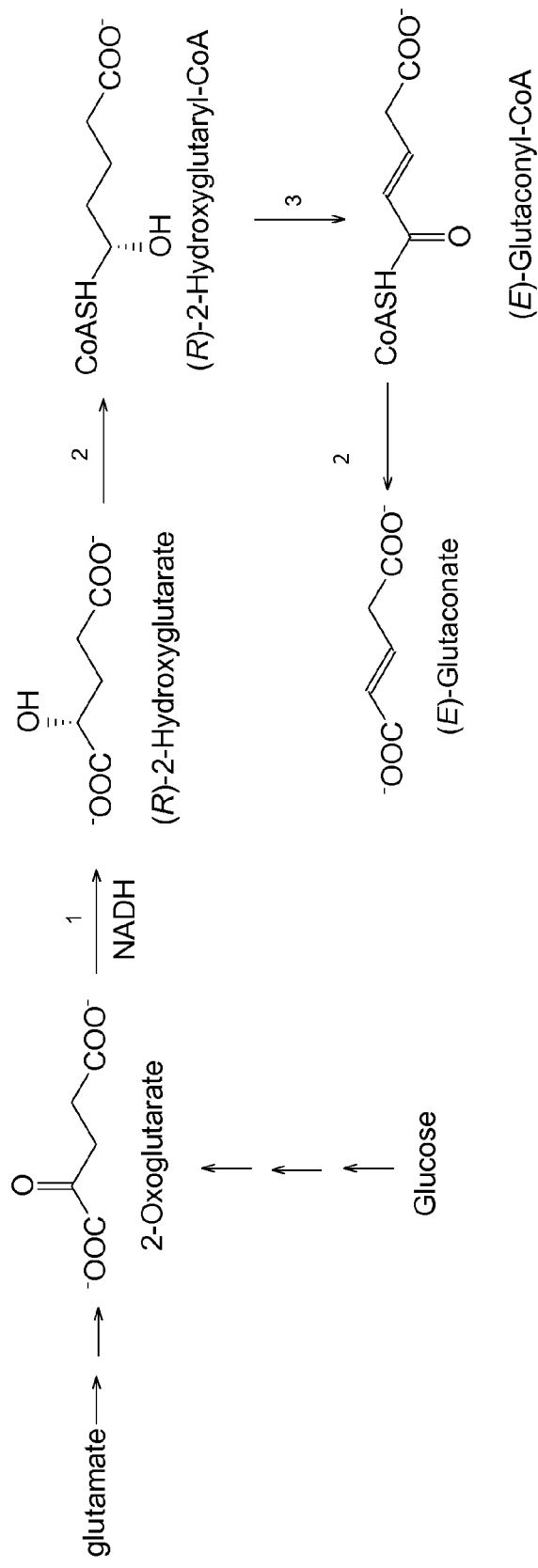
FIG. 1 depicts the pathway for glutaconate production. The enzymes of the final steps are numbered with 1, 2 and 3. 1: 2-hydroxyglutarate dehydrogenase; 2: glutaconate CoA-transferase; 3: 2-hydroxyglutaryl-CoA dehydratase.

The above-mentioned problem was solved by the present invention teaching a biocatalytic method for the production of an unsaturated dicarboxylic acid compound, like glutaconate or a structurally similar glutaconate compound (of formula I) which method comprises converting a corresponding 2-hydroxy-substituted dicarboxylic acid in a recombinant microorganism co-expressing a glutaconate CoA-transferase and a 2-hydroxyglutaryl-CoA dehydratase system, so that said unsaturated dicarboxylic acid is formed For example, in order to convert *Escherichia coli* to a glutaconate producer, the present inventors expressed six genes, encoding 2-hydroxyglutarate dehydrogenase (HgdA, 1 in FIG. 1), glutaconate CoA-transferase (GcdAB, 2), 2-hydroxyglutaryl-CoA dehydratase (HgdAB, 3) and its activator (HgdC, 3). The new pathway can divert at α-ketoglutarate derived from glucose via the Embden-Meyerhof pathway and the citrate cycle.

DETAILED DESCRIPTION OF THE INVENTION

1. Preferred Embodiments

In a first embodiment the present invention provides a biocatalytic method for the production of an unsaturated dicarboxylic acid compound of the general formula I

HOOC—CH=CH—X—COOH  (I)

in particular the E-form of such a compound;
wherein X represents a linear or branched, optionally unsaturated, optionally substituted hydrocarbon group, preferably having 1, 2, 3 or 4 carbon atoms;
which method comprises
  converting a 2-hydroxy-substituted dicarboxylic acid III compound

HOOC—C(OH)H—CH$_2$—X—COOH  (III)

wherein X is as defined above;
in a recombinant microorganism co-expressing a glutaconate CoA-transferase (E.C. 2.8.3.12) and a 2-hydroxyglutaryl-CoA dehydratase system, under conditions allowing formation of the desired product, and particularly or optionally in the presence of a coenzyme A (CoA) source, like acyl-CoA, like C$_2$-C$_6$-acyl-CoA, and in particular acetyl-coenzyme A, which CoA source may be of any origin, like endogenic to said microorganism, i.e. produced by said microorganism, or exogenic, i.e. added to said microorganism or production medium, so that said compound of formula I is formed, and/or optionally in the presence of any other exogenic or endogenic factors required for or improving formation of a compound of formula I;
  and optionally isolating said compound of formula I in the form of a substantially pure stereoisomer, as for example the Z-form or in particular the E-form, or as a mixture of stereoisomers, each either in the form of its salts or as free acid.

In compounds of formula I said group X preferably may be selected from $(CH_2)_n$, with n being an integer from 1 to 4, CH=CH, $CH_2$—C(=O), or CH=C(OH). In particular X is selected from $CH_2$, $C_2H_4$, CH=CH and CH=C(OH).

According to the present invention said 2-hydroxy-substituted dicarboxylic acid III is preferably formed by said recombinant microorganism in a 2-hydroxyglutarate dehydrogenase (E.C. 1.1.1.-) catalyzed conversion of a 2-oxo-dicarboxylic acid compound of formula II

HOOC—C(=O)—$CH_2$—X—COOH  (II)

wherein X is defined above. In particular, said 2-hydroxyglutarate dehydrogenase may be co-expressed by said recombinant microorganism as well.

In said method of the invention said oxo-dicarboxylic acid compound of formula II is either added to or fermentatively produced by said recombinant microorganism.

In particular, the method of the invention comprises the cultivation of at least one recombinant microorganism, which microorganism is derived from a parent microorganism having the ability to produce said 2-oxo-dicarboxylic acid compound of formula II as intermediary product of a metabolic pathway, and additionally having the ability to express heterologously at least one of the above mentioned enzymes and proteins. For example, said microorganism is a glutamate and/or glucose metabolizing aerobic or anaerobic recombinant bacterium, and said compound of formula II is 2-oxo-glutarate formed by the biodegradation of glutamate (for example by the action of glutamate dehydrogenase) and/or glucose (for example via the Embden-Meyerhof pathway and the Krebs or citric acid cycle). If appropriate one or more, as for example 2, 3, 4 or 5, individual enzymes involved in said glutamate or glucose metabolism may be deregulated in order to further assist, or improve the formation of the intended product and/or to reduce or avoid the formation of undesired side products or secondary products (formed by the metabolization of the intended product) which otherwise would lessen or decrease the actual amount or concentration of the intended product as formed by the microrganism.

In particular, said glutamate and/or glucose metabolizing recombinant bacterium is selected from bacteria of the genus Escherichia, as for example E. coli, like the strain E. coli BL21-CodonPlus® (DE3)-RIL strain (Stratgene). The CodonPlus plasmid responsible for chloramphenicol resistance may also be removed.

In a particular embodiment of the method of the invention said 2-hydroxyglutaryl-CoA dehydratase system comprises a 2-hydroxyglutaryl-CoA dehydratase (E.C. 4.2.1.) and, if required for inducing and/or maintaining the intended dehydratase activity, optionally an activator protein for said enzyme. Said activator protein may be required for establishing dehydratase activity.

According to the present invention said enzymes and proteins (glutaconate CoA-transferase, 2-hydroxyglutaryl-CoA dehydratase, activator, 2-hydroxyglutarate dehydrogenase) are of prokaryotic or eukaryotic origin. In particular they may originate from different microbial genera or strains. For example it is not an absolute requirement that dehydratase and the activator for establishing dehydratase activity are derived from the same microbial genus or strain as long as the activator cooperates with (activates the) dehydratase enzyme as used for the bioconversion reaction.

In a particular embodiment, said enzymes and activator originate from the same or different anaerobic bacterium, which bacterium being able to convert glutamate into glutaconate. For example, said anaerobic bacterium is selected from bacteria of the genus Acidaminococcus, Clostridium, Fusobacterium or Peptostreptococcus, in particular Acidaminococcus fermentans, Clostridium symbiosum, Clostridium sporosphaeroides, Fusobacterium nucleatum including all subspecies, or Peptostreptococcus asaccharolyticus.

In particular, said 2-hydroxyglutarate dehydrogenase (HgdH) comprises at least one amino acid sequence of SEQ ID NO: 16 (FN0487, annotated as D-lactate dehydrogenase—Fusobacterium nucleatum subsp. nucleatum ATCC 25586; GeneID: 991766) or SEQ ID NO:2 (1XDW_A (A. fermentans); or a sequence having at least 50% identity to at least one of said sequences, as for example at least 60, 70, 80, 85, 90, 92, 95, 96, 97, 98 or 99% sequence identity, and still retaining the intended enzyme activity (or function), i.e. being applicable as HgdH enzyme; for example said enzyme may be a homodimer, as for example the A. fermentans enzyme; for example the A. fermentans enzyme shows 61% sequence identity to the enzyme from F. nucleatum.

In particular, said glutaconate CoA transferase (GctAB), which may be a heterooctamer $(\alpha_4\beta_4)$ (a) comprises at least one alpha (A) and at least one beta (B) subunit, wherein said alpha subunit comprising an amino acid sequence according to SEQ ID NO: 4 or a sequence having at least 50% identity thereto, as for example at least 60, 70, 80, 85, 90, 92, 95, 96, 97, 98 or 99% sequence identity; and wherein said beta subunit comprising an amino acid sequence according to SEQ ID NO: 6 or a sequence having at least 50% identity thereto, as for example at least 60, 70, 80, 85, 90, 92, 95, 96, 97, 98 or 99% sequence identity; and still retaining the intended enzyme activity, i.e. being applicable as GctAB enzyme; or (b) comprises at least one alpha and at least one beta subunit, wherein said alpha subunit comprising an amino acid sequence according to SEQ ID NO: 22 or a sequence having at least 50% identity thereto, as for example at least 60, 70, 80, 85, 90, 92, 95, 96, 97, 98 or 99% sequence identity; and wherein said beta subunit comprising an amino acid sequence according to SEQ ID NO: 24 or a sequence having at least 50% identity thereto, as for example at least 60, 70, 80, 85, 90, 92, 95, 96, 97, 98 or 99% sequence identity; and still retaining the intended enzyme activity, i.e. being applicable as GctAB enzyme; or (c) comprises at least one alpha and at least one beta subunit, wherein said alpha subunit comprising an amino acid sequence according to SEQ ID NO: 18 or a sequence having at least 50% identity thereto, as for example at least 60, 70, 80, 85, 90, 92, 95, 96, 97, 98 or 99% sequence identity; and wherein said beta subunit comprising an amino acid sequence according to SEQ ID NO: 20 or a sequence having at least 50% identity thereto, as for example at least 60, 70, 80, 85, 90, 92, 95, 96, 97, 98 or 99% sequence identity; and still retaining the intended enzyme activity, i.e. being applicable as GctAB enzyme.

In particular, said 2-hydroxyglutaryl-CoA dehydratase, which may be a heterodimer (AB) or trimer (ABD) with one [4Fe-4S] cluster in each A and each B subunit, and (a) comprises at least one alpha (A) and at least one beta (B) subunit, wherein said alpha subunit comprising an amino acid sequence according to SEQ ID NO: 26 or a sequence having at least 50% identity thereto, as for example at least 60, 70, 80, 85, 90, 92, 95, 96, 97, 98 or 99% sequence identity; and wherein said beta subunit comprising an amino acid sequence according to SEQ ID NO: 28 or a sequence having at least 50% identity thereto, as for example at least 60, 70, 80, 85, 90, 92, 95, 96, 97, 98 or 99% sequence identity; and still retaining the intended enzyme activity, i.e. being applicable as dehydratase enzyme; or (b) comprises at least one alpha (A), at least one beta (B) subunit and at least one delta (D) subunit, wherein said alpha subunit comprising an amino acid sequence according to SEQ ID NO: 30 or a sequence having at least 50% identity thereto, as for example at least 60, 70, 80, 85, 90, 92, 95, 96, 97, 98 or 99% sequence identity; and wherein said beta subunit comprising an amino acid sequence according to SEQ ID NO: 32 or a sequence having at least 50% identity thereto, as for example at least 60, 70, 80, 85, 90, 92, 95, 96, 97, 98 or 99% sequence identity; and wherein said gamma subunit comprising an amino acid sequence according to SEQ ID NO: 34 or a sequence having at least 50% identity thereto, as for example at least 60, 70, 80, 85, 90, 92, 95, 96, 97, 98 or 99% sequence identity; and still retaining the intended enzyme activity, i.e. being applicable as dehydratase enzyme; or (c) comprises at least one alpha and at least one beta subunit, wherein said alpha subunit comprising an amino acid sequence according to SEQ ID NO: 8 or a sequence having at least 50% identity thereto, as for example at least 60, 70, 80, 85, 90, 92, 95, 96, 97, 98 or 99% sequence identity; and wherein said beta subunit comprising an amino acid sequence according to SEQ ID NO: 10 or a sequence having at least 50% identity thereto, as for example at least 60, 70, 80, 85, 90, 92, 95, 96, 97, 98 or 99% sequence identity; and still retaining the intended enzyme activity, i.e. being applicable as dehydratase enzyme.

In particular, said the activator protein comprises at least one amino acid sequence of SEQ ID NO: 12, 36 or 38 or a sequence having at least 50% identity to at least one of said sequences as for example at least 60, 70, 80, 85, 90, 92, 95, 96, 97, 98 or 99% sequence identity; and still retaining the intended activity, i.e. being applicable as dehydratase activator; an may be a homodimer with one [4Fe-4S] cluster between the two subunits.

In a further particular embodiment, said 2-hydroxyglutaryl-CoA dehydratase is from C. symbiosum (SEQ ID NO: 8 and/or 10); while said 2-hydroxyglutarate dehydrogenase (SEQ ID NO:2); said glutaconate CoA transferase (SEQ ID NO:4 and/or 6) and said activator protein (SEQ ID NO:12) are from A. fermentans; or independently of each other being derived there form, and having a sequence of at least 50% identity to the parent sequence, as for example at least 60, 70, 80, 85, 90, 92, 95, 96, 97, 98 or 99% sequence identity; and still retaining the intended enzyme or activator activity. Said proteins may be present in the form of the active quaternary structure or may be present in the form of active fragments or subunits thereof.

Moreover, said proteins and enzymes may each be encoded by a nucleic acid sequence, which is adapted to the codon usage of said microorganism having the ability to produce said 2-oxo-dicarboxylic acid of formula II.

In addition, said proteins and enzymes may be encoded by nucleic acid sequences contained in one single or more expression vectors in may be encoded as single or multiple copies.

Additionally, at least one of said co-expressed proteins is heterologous to said recombinant microorganism.

The present invention also relates to:
an expression cassette, comprising a combination of at least two different nucleic acid sequences encoding an enzyme or protein as defined above (i.e. the required set (or a subset of) of sequences encoding the required set (or a subset of) of enzymes/proteins necessary for producing compounds of formula I via compounds of formula III), which sequences are operatively linked to at least one regulatory nucleic acid sequence;
a recombinant vector, comprising at least one of said expression cassettes;
a recombinant prokaryotic or eukaryotic host, transformed with at least one such vector.

In particular such recombinant hosts have the ability to produce a 2-oxo-dicarboxylic acid compound of formula (II), which is converted to a compound of formula (I) upon expression of said expression products as encoded by said at least one vector. For example said host may be a recombinant strain of a bacterium of the genus Escherichia.

In another embodiment the present invention relates to a method of preparing a polyamide or polyester, which method comprises
a) preparing a mono-unsaturated dicarboxylic acid compounds of the general formula (I) as defined above a by method as described herein;
b) isolating said compound optionally followed by hydrogenation in order to remove the C=C-double bond; and
c) polymerizing said compound as obtained according to step b), with at least one suitable polyvalent polymerizable amine monomer or polyvalent polymerizable hydroxyl compound.

In particular, said polyamine is a di-amine, a tri-amine or a mixture thereof and said polyvalent hydroxyl compound is a diol or triol or a mixture thereof. For example said polymerization reaction may be performed in the presence of a suitable catalyst, as for example acid or base catalyst.

In another embodiment the present invention relates to a method of preparing a polymer, which method comprises
a) preparing a mono-unsaturated dicarboxylic acid compounds of the general formula (I) as defined above a by method as defined above;
b) isolating said compound; and
c) polymerizing said compound as obtained according to step b), with at least one suitable unsaturated polymerizable monomer.

For example, said polymerization may be performed in the presence of a suitable radical initiator. Suitable comonomers are those which may be applied in a radical-initiated polymerization, as for example monomers containing at least one polymerizable C=C-bond, like vinyl, acryl and methacryl.

In another embodiment of the method described herein at least one gene, as for example 1, 2, 3 or 4 genes, of a biosynthetic pathway in said recombinant microorganism directly or indirectly affecting the formation and/or decomposition of at least one compound of formula (I), (II) or (III), may deregulated (up or down regulated) in order to further optimize the method of the invention.

2. Explanation of Particular Terms

Unless otherwise stated the expressions "glutaconate" and "glutaconic acid" or the expressions "glutaconate compound" and "glutaconic acid compound" or the expressions "unsaturated dicarboxylic acid" or "unsaturated dicarboxylate compound" are considered to be synonymous. The glutaconate or dicarboxylic acid compound (of formula I) as obtained according to the present invention may be in the form of the free acid, in the form of a partial or complete salt of said acid or in the form of mixtures of the acid and its salt.

A dicarboxylic acid "salt" comprises for example metal salts, as for example zinc glutaconate, mono- or di-alkalimetal salts of said acid, like mono-sodium di-sodium, monopotassium and di-potassium salts as well as alkaline earth metal salts as for example the calcium or magnesium salts.

The term "biocatalytic method" refers to any method performed in the presence of catalytic activity of an enzyme as defined herein, i.e. in the presence of isolated pure or crude enzyme or entire microbial cells containing or expression such enzyme activity.

The term "stereospecific" means that one of several stereoisomers or enantiomers is formed by the enzyme in high enantiomeric excess or purity, of at least 90% ee, preferably at least 95% ee, in particular at least 98% ee, or at least 99% ee. the ee % value is calculated according to the following formula $$ee\ \% = [X_A - X_B]/[X_A + X_B] * 100,$$

wherein $X_A$ and $X_B$ refer to the molar fraction of enantiomer A or B, respectively.

Examples of "stereoisomers" are E- and Z-isomers or R- and S enantiomers.

"Deregulation" has to be understood in its broadest sense, and comprises an increase or decrease of complete switch off of an enzyme (target enzyme) activity by different means well known to those in the art. Suitable methods comprise for example an increase or decrease of the copy number of gene and for enzyme molecules in an organism, or the modification of another feature of the enzyme affecting the its enzymatic activity, which then results in the desired effect on a metabolic pathway at issue, or any pathway or enzymatic reaction coupled thereto. Suitable genetic manipulation can also include, but is not limited to, altering or modifying regulatory sequences or sites associated with expression of a particular gene (e.g., by removing strong promoters, inducible promoters or multiple promoters), modifying the chromosomal location of a particular gene, altering nucleic acid sequences adjacent to a particular gene such as a ribosome binding site or transcription terminator, decreasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules), or other methods to knock-out or block expression of the target protein.

A preferred way of an "amplification" is an "up"-mutation which increases the gene activity e.g. by gene amplification using strong expression signals and/or point mutations which enhance the enzymatic activity.

A preferred way of an "attenuation" is a "down"-mutation which decreases the gene activity e.g. by gene deletion or disruption, using weak expression signals and/or point mutations which destroy or decrease the enzymatic activity.

The term "heterologous" or "exogenous" refers to sequences as described herein, which are introduced into or produced (transcribed or translated) by a genetically manipulated microorganism as defined herein and which microorganism prior to said manipulation did not contain or did not produce said sequence. In particular said microorganism prior to said manipulation may not contain or express said heterologous enzyme activity, or may contain or express an endogenous enzyme of comparable activity or specificity, which is encoded by a different coding sequence or by an enzyme of different amino acid sequence, and said endogenous enzyme may convert the same substrate or substrates as said exogenous enzyme.

A "parent" microorganism of the present invention is any microorganism having the ability to produce a compound of formula (II) as intermediary product.

An "intermediary product" is understood as a product, which is transiently or continuously formed during a chemical or biochemical process, in a not necessarily analytically directly detectable concentration. Said "intermediary product" may be removed from said biochemical process by a second, chemical or biochemical reaction.

A "recombinant host" may be any prokaryotic or eukaryotic cell, which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., MOLECULAR CLONING: A LABORATORY MANUAL, Second Edition, Cold Spring Harbor Laboratory, Cold Spring Harbor, N.Y. (1989).

The term "recombinant microorganism" includes a microorganism (e.g., bacteria, yeast cell, fungal cell, etc.) which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism or "parent" microorganism which it was derived from.

As used herein, a "substantially pure" protein or enzyme means that the desired purified protein is essentially free from contaminating cellular components, as evidenced by a single band following polyacrylamide-sodium dodecyl sulfate gel electrophoresis (SDS-PAGE). The term "substantially pure" is further meant to describe a molecule, which is homogeneous by one or more purity or homogeneity characteristics used by those of skill in the art. For example, a substantially pure enzyme or protein will show constant and reproducible characteristics within standard experimental deviations for parameters such as the following: molecular mass, chromatographic migration, amino acid composition, amino acid sequence, blocked or unblocked N-terminus, HPLC elution profile, biological activity, and other such parameters. The term, however, is not meant to exclude artificial or synthetic mixtures of said enzyme or protein with other compounds. In addition, the term is not meant to exclude fusion proteins optionally isolated from a recombinant host.

3. Further Embodiments of the Invention 3.1 Proteins According to the Invention

The present invention is not limited to the specifically mentioned enzymes/proteins, but also extends to functional equivalents thereof.

"Functional equivalents" or "analogs" or "functional mutations" of the concretely disclosed enzymes are, within the scope of the present invention, various polypeptides thereof, which moreover possess the desired biological function or activity, e.g. enzyme activity.

For example, "functional equivalents" means enzymes, which, in a test used for enzymatic activity, display at least a 1 to 10%, or at least 20%, or at least 50%, or at least 75%, or at least 90% higher or lower activity of an enzyme, as defined herein.

"Functional equivalents", according to the invention, also means in particular mutants, which, in at least one sequence position of the amino acid sequences stated above, have an amino acid that is different from that concretely stated, but nevertheless possess one of the aforementioned biological activities. "Functional equivalents" thus comprise the mutants obtainable by one or more amino acid additions, substitutions, deletions and/or inversions, where the stated changes can occur in any sequence position, provided they lead to a mutant with the profile of properties according to the invention. Functional equivalence is in particular also provided if the reactivity patterns coincide qualitatively between the mutant and the unchanged polypeptide, i.e. if for example the same substrates are converted at a different rate. Examples of suitable amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent enzymes can be determined on the basis of the concrete parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated above or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" that are also included according to the invention are homologues of the concretely disclosed proteins. These possess percent identity values as stated above. Said values refer to the identity with the concretely disclosed amino acid sequences, and may be calculated according to the algorithm of Pearson and Lipman, Proc. Natl. Acad, Sci. (USA) 85(8), 1988, 2444-2448.

The % identity values may also be calculated from BLAST alignments, algorithm blastp (protein-protein BLAST) or by applying the Clustal setting as given below.

A percentage identity of a homologous polypeptide according to the invention means in particular the percentage identity of the amino acid residues relative to the total length of one of the amino acid sequences concretely described herein.

In the case of a possible protein glycosylation, "functional equivalents" according to the invention comprise proteins of the type designated above in deglycosylated or glycosylated form as well as modified forms that can be obtained by altering the glycosylation pattern.

Such functional equivalents or homologues of the proteins or polypeptides according to the invention can be produced by mutagenesis, e.g. by point mutation, lengthening or shortening of the protein.

Such functional equivalents or homologues of the proteins according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art (e.g. Narang, S. A. (1983) Tetrahedron 39:3; Itakura et al. (1984) Annu. Rev. Biochem. 53:323; Itakura et al. (1984) Science 198:1056; Ike et al. (1983) Nucleic Acids Res. 11:477).

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues (Arkin and Yourvan (1992) PNAS 89:7811-7815; Delgrave et al. (1993) Protein Engineering 6(3):327-331).

3.2 Coding Nucleic Acid Sequences

The invention also relates to nucleic acid sequences that code for enzymes/proteins as defined herein.

The present invention also relates to nucleic acids with a certain degree of "identity" to the sequences specifically disclosed herein. "Identity" between two nucleic acids means identity of the nucleotides, in each case over the entire length of the nucleic acid.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuplesize | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The invention also relates to nucleic acid sequences (single-stranded and double-stranded DNA and RNA sequences, e.g. cDNA and mRNA), coding for one of the above polypeptides and their functional equivalents, which can be obtained for example using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for identifying or amplifying coding nucleic acids according to the invention.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (see below) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1× SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular be carried out under stringent conditions. Such hybridization conditions are for example described in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: Incubation at 42° C. overnight in a solution consisting of 50% formamide, 5×SSC (750 mM NaCl, 75 mM tri-sodium citrate), 50 mM sodium phosphate (pH 7.6), 5×Denhardt Solution, 10% dextran sulfate and 20 g/ml denatured, sheared salmon sperm DNA, followed by washing of the filters with 0.1×SSC at 65° C.

The invention also relates to derivatives of the concretely disclosed or derivable nucleic acid sequences.

Thus, further nucleic acid sequences according to the invention can be derived from the sequences specifically disclosed herein and can differ from it by addition, substitution, insertion or deletion of individual or several nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism, as well as naturally occurring variants, e.g. splicing variants or allelic variants, thereof.

It also relates to sequences that can be obtained by conservative nucleotide substitutions (i.e. the amino acid in question is replaced by an amino acid of the same charge, size, polarity and/or solubility).

The invention also relates to the molecules derived from the concretely disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of nucleic acid sequences according to the invention mean for example allelic variants, having at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

Furthermore, derivatives are also to be understood to be homologues of the nucleic acid sequences according to the invention, for example animal, plant, fungal or bacterial homologues, shortened sequences, single-stranded DNA or RNA of the coding and noncoding DNA sequence. For example, homologues have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

3.3 Preparation of Functional Mutants

The skilled reader is also aware of methods of generating functional mutants.

Depending on the technique applied, a skilled reader may generate arbitrary or directed mutations in genes or noncoding nucleic acid regions (which, for example, may be of importance for regulating gene expression) and, afterwards, may generate suitable gene libraries. The molecular biological method required therefore all well known in the art, and, for example, described by Sambrook and Russell, Molecular Cloning. 3. Edition, Cold Spring Harbor Laboratory Press 2001.

Methods of modifying genes and consequently of modifying the encoded proteins are well known to the skilled reader, as for example

- site-specific mutagenesis wherein single or multiple nucleotides of a gene are specifically replaced (Trower M K (Ed.) 1996; In vitro mutagenesis protocols. Humana Press, New Jersey),
- saturation mutagenesis, wherein at any position of a gene the codon of any amino acid may be exchanged or added (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Barik S (1995) Mol Biotechnol 3:1),
- error-prone polymerase chain reaction (PCR), wherein nucleotide sequences are mutated via the action of an incorrectly functioning DNA-polymerase (Eckert K A, Kunkel T A (1990) Nucleic Acids Res 18:3739);
- SeSaM method (Sequence Saturation Method), wherein preferred substitutions are avoided by the polymerase (Schenk et al., Biospektrum, Vol. 3, 2006, 277-279)
- Passaging of genes in mutator-strains, showing an increased occurrence of mutations of nucleotide sequences, for example in view of a defective DNA-repair mechanism (Greener A, Callahan M, Jerpseth B (1996) An efficient random mutagenesis technique using an E. coli mutator strain. In: Trower M K (Hrsg.) In vitro mutagenesis protocols. Humana Press, New Jersey), or
- DNA-Shuffling, wherein a pool of closely related genes is formed and digested and wherein the fragments are used as templates for a PCR reaction, and wherein full-length mosaic genes are formed (Stemmer W P C (1994) Nature 370:389; Stemmer W P C (1994) Proc Natl Acad Sci USA 91:10747).

By applying the so-called directed evolution technique (see for example Reetz M T and Jaeger K-E (1999), Topics Curr Chem 200:31; Zhao H, Moore J C, Volkov A A, Arnold F H (1999), Methods for optimizing industrial enzymes by directed evolution, In: Demain A L, Davies J E (Hrsg.) Manual of industrial microbiology and biotechnology. American Society for Microbiology) a skilled reader will be able to specifically prepare functional mutants in large scale. In a first step libraries of a specific protein are generated, for example, by applying any one of the above mentioned methods. Afterwards said libraries are expressed, for example by applying bacteria or phage display systems.

Those genes expressing functional mutants showing the desired feature profile may be selected and subjected to further mutation. The steps of mutation and selection or screening may be repeated iteratively until one of the obtained mutants shows the desired feature profile.

By the iterative approach a limited number of mutations, as for example 1 to 5 mutations, may be performed and their influence on the enzyme feature at issue may be evaluated and further improved mutants may be selected stepwise. Said selected mutant may then be subjected to a further mutation in substantially the same may. The number of single mutants to be evaluated may be reduced significantly in this way. The teaching of the present invention provide important information as regards structure and sequence of the enzyme/protein at issue, based on which it should be possible to generate further enzymes/proteins with the desired modified feature profile. In particular, so-called hot spots, i.e. sequence regions may be defined, which potentially may be suited for further mutation in order to modify or generate a desired feature of the enzyme/protein.

3.4 Constructs According to the Invention

The invention also relates to expression constructs, containing, under the genetic control of regulatory nucleic acid sequences, a nucleic acid sequence coding for a polypeptide or fusion protein according to the invention; as well as vectors comprising at least one of these expression constructs.

"Expression unit" means, according to the invention, a nucleic acid with expression activity, which comprises a promoter as defined herein and, after functional association with a nucleic acid that is to be expressed or a gene, regulates the expression, i.e. the transcription and the translation of this nucleic acid or of this gene. In this context, therefore, it is also called a "regulatory nucleic acid sequence". In addition to the promoter, other regulatory elements may be present, e.g. enhancers.

"Expression cassette" or "expression construct" means, according to the invention, an expression unit, which is functionally associated with the nucleic acid that is to be expressed or the gene that is to be expressed. In contrast to an expression unit, an expression cassette thus comprises not only nucleic acid sequences which regulate transcription and translation, but also the nucleic acid sequences which should be expressed as protein as a result of the transcription and translation.

The terms "expression" or "overexpression" describe, in the context of the invention, the production or increase of intracellular activity of one or more enzymes in a microorganism, which are encoded by the corresponding DNA. For this, it is possible for example to insert a gene in an organism, replace an existing gene by another gene, increase the number of copies of the gene or genes, use a strong promoter or use a gene that codes for a corresponding enzyme with a high activity, and optionally these measures can be combined.

Preferably such constructs according to the invention comprise a promoter 5'-upstream from the respective coding sequence, and a terminator sequence 3'-downstream, and optionally further usual regulatory elements, in each case functionally associated with the coding sequence.

A "promoter", a "nucleic acid with promoter activity" or a "promoter sequence" mean, according to the invention, a nucleic acid which, functionally associated with a nucleic acid that is to be transcribed, regulates the transcription of this nucleic acid.

"Functional" or "operative" association means, in this context, for example the sequential arrangement of one of the nucleic acids with promoter activity and of a nucleic acid sequence that is to be transcribed and optionally further regulatory elements, for example nucleic acid sequences that enable the transcription of nucleic acids, and for example a terminator, in such a way that each of the regulatory elements can fulfill its function in the transcription of the nucleic acid sequence. This does not necessarily require a direct association in the chemical sense. Genetic control sequences, such as enhancer sequences, can also exert their function on the target sequence from more remote positions or even from other DNA molecules. Arrangements are preferred in which the nucleic acid sequence that is to be transcribed is positioned behind (i.e. at the 3' end) the promoter sequence, so that the two sequences are bound covalently to one another. The distance between the promoter sequence and the nucleic acid sequence that is to be expressed transgenically can be less than 200 bp (base pairs), or less than 100 bp or less than 50 bp.

Apart from promoters and terminators, examples of other regulatory elements that may be mentioned are targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise in particular sequences selected from those, specifically mentioned herein or derivatives and homologues thereof, as well as the nucleic acid sequences that can be derived from amino acid sequences specifically mentioned herein which are advantageously associated operatively or functionally with one or more regulating signal for controlling, e.g. increasing, gene expression.

In addition to these regulatory sequences, the natural regulation of these sequences can still be present in front of the actual structural genes and optionally can have been altered genetically, so that natural regulation is switched off and the expression of the genes has been increased. The nucleic acid construct can also be of a simpler design, i.e. without any additional regulatory signals being inserted in front of the coding sequence and without removing the natural promoter with its regulation. Instead, the natural regulatory sequence is silenced so that regulation no longer takes place and gene expression is increased.

A preferred nucleic acid construct advantageously also contains one or more of the aforementioned enhancer sequences, functionally associated with the promoter, which permit increased expression of the nucleic acid sequence. Additional advantageous sequences, such as other regulatory elements or terminators, can also be inserted at the 3' end of the DNA sequences. One or more copies of the nucleic acids according to the invention can be contained in the construct. The construct can also contain other markers, such as antibiotic resistances or auxotrophy-complementing genes, optionally for selection on the construct.

Examples of suitable regulatory sequences are contained in promoters such as cos-, tac-, trp-, tet-, trp-tet-, lpp-, lac-, lpp-lac-, lacI$^{q}$-, T7-, T5-, T3-, gal-, trc-, ara-, rhaP (rhaP$_{BAD}$) SP6-, lambda-P$_R$- or in the lambda-P$_L$ promoter, which find application advantageously in Gram-negative bacteria. Other advantageous regulatory sequences are contained for example in the Gram-positive promoters ace, amy and SPO2, in the yeast or fungal promoters ADC1, MFalpha, AC, P-60, CYC1, GAPDH, TEF, rp28, ADH. Artificial promoters can also be used for regulation.

For expression, the nucleic acid construct is inserted in a host organism advantageously in a vector, for example a plasmid or a phage, which permits optimum expression of the genes in the host. In addition to plasmids and phages, vectors are also to be understood as meaning all other vectors known to a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are, for example in E. coli, pLG338, pACYC184, pBR322, pUC18, pUC19, pKC30, pRep4, pHS1, pKK223-3, pDHE19.2, pHS2, pPLc236, pMBL24, pLG200, pUR290, pIN-III[113]-B1, λgt11 or pBdCl; in nocardioform actinomycetes pJAM2; in Streptomyces pIJ101, pIJ364, pIJ702 or pIJ361; in bacillus pUB110, pC194 or pBD214; in Corynebacterium pSA77 or pAJ667; in fungi pALS1, pIL2 or pBB116; in yeasts 2alphaM, pAG-1, YEp6, YEp13 or pEMBLYe23 or in plants pLGV23, pGHlac$^+$, pBIN19, pAK2004 or pDH51. The aforementioned plasmids represent a small selection of the possible plasmids. Other plasmids are well known to a person skilled in the art and will be found for example in the book Cloning Vectors (Eds. Pouwels P. H. et al. Elsevier, Amsterdam-New York-Oxford, 1985, ISBN 0 444 904018). Further suitable plasmid are also mentioned in the experimental part.

In a further embodiment of the vector, the vector containing the nucleic acid construct according to the invention or the nucleic acid according to the invention can be inserted advantageously in the form of a linear DNA in the microorganisms and integrated into the genome of the host organism through heterologous or homologous recombination. This linear DNA can comprise a linearized vector such as plasmid or just the nucleic acid construct or the nucleic acid according to the invention.

For optimum expression of heterologous genes in organisms, it is advantageous to alter the nucleic acid sequences in accordance with the specific codon usage employed in the organism. The codon usage can easily be determined on the basis of computer evaluations of other, known genes of the organism in question.

The production of an expression cassette according to the invention is based on fusion of a suitable promoter with a suitable coding nucleotide sequence and a terminator signal or polyadenylation signal. Common recombination and cloning techniques are used for this, as described for example in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is inserted advantageously in a host-specific vector for expression in a suitable host organism, to permit optimum expression of the genes in the host. Vectors are well known to a person skilled in the art and will be found for example in "Cloning Vectors" (Pouwels P. H. et al., Publ. Elsevier, Amsterdam-New York-Oxford, 1985).

3.5 Hosts that can be used According to the Invention

Depending on the context, the term "microorganism" means the starting microorganism (wild-type) or a genetically modified microorganism according to the invention, or both.

The term "wild-type" means, according to the invention, the corresponding starting microorganism, and need not necessarily correspond to a naturally occurring organism.

By means of the vectors according to the invention, recombinant microorganisms can be produced, which have been transformed for example with at least one vector according to the invention and can be used for the fermentative production according to the invention.

Advantageously, the recombinant constructs according to the invention, described above, are inserted in a suitable host system and expressed. Preferably, common cloning and transfection methods that are familiar to a person skilled in the art are used, for example co-precipitation, protoplast fusion, electroporation, retroviral transfection and the like, in order to secure expression of the stated nucleic acids in the respective expression system. Suitable systems are described for example in Current Protocols in Molecular Biology, F. Ausubel et al., Publ. Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

The parent microorganisms are typically those which have the ability to produce glutaconate, in particular (E)-glutaconate, from glucose and or glutamate.

Preferably they are bacteria, in particular of the orders *Clostridiales* and *Fusobacteriales*. In particular, the species *A. fermentans* (DSM 20731), *C. symbiosium* (DSM 934), *C. sporospaeroides* (DSM 1294), *P. assacharolyticus* (ATCC 14963) and *F. nucleatum* subsp. *nucleatum* (DSM 15643) have to be mentioned.

ATCC designates American type strain culture collection, and DSM designates Deutsche Sammlung von Mikroorganismen und Zellkulturen GmbH.

The host organism or host organisms according to the invention preferably contain at least one of the nucleic acid sequences, nucleic acid constructs or vectors described in this invention, which code for an enzyme activity according to the above definition.

3.6 Fermentative Production of Glutaconate Products of the Invention

The invention relates to methods for the fermentative production of glutaconate and related compounds of formula (I).

The recombinant microorganisms as used according to the invention can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

These media that can be used according to the invention generally comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc.

All components of the medium are sterilized, either by heating (20 min at 2.0 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 10 hours to 160 hours.

The cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed.

3.7 Product Isolation

The methodology of the present invention can further include a step of recovering glutaconate or related compounds. The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like. For example glutaconate can be recovered from culture media by first removing the microorganisms. The remaining broth is then passed through or over a cation exchange resin to remove unwanted cations and then through or over an anion exchange resin to remove unwanted inorganic anions and organic acids.

3.8 Polymers

In another aspect, the present invention provides a process for the production of polyesters or polyamides (e.g. Nylon® or related polymers) comprising a step as mentioned above for the production of glutaconate compounds. The glutaconate compound is reacted in a known manner with di-, tri- or polyamines to get polyamides or with di-, tri- or polyols to obtain polyesters. For example, the glutaconate-type compound is reacted with polyamine or polyol containing 4 to 10 carbons.

In another aspect, the present invention provides method of preparing a polymer, in particular copolymers, which method comprises preparing a mono-unsaturated dicarboxylic acid compounds of the general formula (I) as defined above a by method as described therein, isolating said compound; and polymerizing said compound with at least one suitable unsaturated polymerizable monomer, preferably in the presence of a polymerization initiator, like for example sodiumperoxide disulfate (NAPS) as radical initiator.

As non-limiting examples of sutable co-monomers for performing the above polymerization reactions there may be mentioned:

polyols such as ethylene glycol, propylene glycol, glycerol, polyglycerols having 2 to 8 glycerol units, erythritol, pentaerythritol, and sorbitol.

polyamines, such as diamines, triamines and tetraamines, like ethylene diamine, propylene diamine, butylene diamine, neopentyl diamine, hexamethylene diamine, octamethylene diamine, diethylene triamine, triethylene tetramine, tetraethylene pentamine, dipropylene triamine, tripropylene tetramine, dihexamethylene triamine, aminopropylethylenediamine and bisaminopropylethylenediamine. Suitable polyamines are also polyalkylenepolyamines. The higher polyamines can be present in a mixture with diamines. Useful diamines include for example 1,2-diaminoethane, 1,3-diaminopropane, 1,4-diaminobutane, 1,5-diaminopentane, 1,6-diaminohexane, 1,8-diaminooctane.

alkenes, in particular $C_2$-$C_{12}$-alkenes which are mounsaturated linear or branched hydrocarbons having from 2 to 12 carbon atoms, as for example ethylene, 1- or 2-propylene, 1-, 2- and 3-butylene, 2-methyl-propylen, 1-, 2-, 3- and 4-pentenylene, 1-, 2-, 3-, 4- and 5-hexylene, 1-, 2-, 3-, 4-, 5- and 6-heptylene, or 1-, 2-, 3-, 4-, 5-, 6- and 7-octylene, 1-decene, 1-dodecene; and also their constitutional isomers.

mono-unsaturated $C_3$-$C_8$-carboxylic acids, like acrylic acid or ($C_1$-$C_7$-alkyl) acrylic acids, vinylacetic acid, crotonic acid, fumaric acid, maleic acid, itaconic acid esters of monoethylenically unsaturated $C_3$-$C_8$ monocarboxylic acids with $C_1$-$C_{20}$ alkanols, $C_5$-$C_8$ cycloalkanol, phenyl-$C_1$-$C_4$ alkanols or phenoxy-$C_1$-$C_4$ alkanols, examples being esters of acrylic acid with $C_1$-$C_{20}$ alkanols, such as methyl acrylate, ethyl acrylate, n-butyl acrylate, 2-butyl acrylate, isobutyl acrylate, tert-butyl acrylate, 2-ethylhexyl acrylate, decyl acrylate, lauryl acrylate and stearyl acrylate, esters of acrylic acid with $C_5$-$C_{10}$ cycloalkanols such as cyclohexyl acrylate, esters of acrylic acid with phenyl-$C_1$-$C_4$ alkanols such as benzyl acrylate, 2-phenylethyl acrylate and 1-phenylethyl acrylate, esters of acrylic acid with phenoxy-$C_1$-$C_4$ alkanols such as 2-phenoxyethyl acrylate, esters of methacrylic acid with $C_1$-$C_{20}$ alkanols, preferably $C_1$-$C_{10}$ alkanols, such as methyl methacrylate, ethyl methacrylate, n-butyl methacrylate, 2-butyl methacrylate, isobutyl methacrylate, tert-butyl methacrylate, 2-ethylhexyl methacrylate, decyl methacrylate, lauryl methacrylate and stearyl methacrylate, esters of methacrylic acid with $C_5$-$C_{10}$ cycloalkanols, such as cyclohexyl methacrylate, esters of methacrylic acid with phenyl-$C_1$-$C_4$ alkanols, such as benzyl methacrylate, 2-phenylethyl methacrylate and 1-phenylethyl methacrylate, and esters of methacrylic acid with phenoxy-$C_1$-$C_4$ alkanols, such as 2-phenoxyethyl methacrylate;

diesters of monoethylenically unsaturated $C_4$-$C_8$ dicarboxylic acids with $C_1$-$C_{20}$ alkanols, such as diesters of maleic acid or of fumaric acid with $C_1$-$C_{20}$ alkanols, examples being dimethyl maleate, diethyl maleate, di-n-butyl maleate, dimethyl fumarate, diethyl fumarate, and di-n-butyl fumarate;

$C_1$-$C_{20}$ alkylamides and di-$C_1$-$C_{20}$ alkylamides of monoethylenically unsaturated $C_3$-$C_8$ monocarboxylic acids, especially the $C_1$-$C_{20}$ alkylamides and di-$C_1$-$C_{20}$ alkylamides of acrylic acid and of methacrylic acid, for example, amides of monoethylenically unsaturated carboxylic acids, such as acrylamide or methacrylamide, anhydrides of monoethylenically unsaturated monocarboxylic and dicarboxylic acids having 3 to 8 C atoms, such as acrylic acid anhydride, methacrylic acid anhydride, maleic anhydride or itaconic anhydride, hydroxyl-$C_2$-$C_4$ alkyl esters of monoethylenically unsaturated monocarboxylic or dicarboxylic acids having 3 to 8 C atoms, such as 2-hydroxyethyl acrylate, 2-hydroxypropyl acrylate, 3-hydroxypropyl acrylate, 2-hydroxybutyl acrylate, 4-hydroxybutyl acrylate, 2-hydroxyethyl methacrylate, 2-hydroxypropyl methacrylate, 3-hydroxypropyl methacrylate, 2-hydroxybutyl methacrylate, 4-hydroxybutyl methacrylate, monoethylenically unsaturated sulfonic acids and their salts, examples being vinylsulfonic acid, allylsulfonic acid, methallylsulfonic acid, styrenesulfonic acid, 2-acrylamido-2-methylpropanesulfonic acid, 2-methacrylamido-2-methylpropanesulfonic acid, 2-acrylamidoethanesulfonic acid, 2-methacrylamidoethanesulfonic acid, 2-acryloyloxyethanesulfonic acid, 2-methacryloyloxyethanesulfonic acid, 3-acryloyloxypropanesulfonic acid and 2-methacryloyloxypropanesulfonic acid, monoethylenically unsaturated nitriles having 3 to 5 C atoms, such as acrylonitrile and methacrylonitrile, N-vinyl heterocycles such as N-vinylpyrrolidone, N-vinylcaprolactam, N-vinylimidazole, and monoethylenically unsaturated compounds having at least one poly-$C_2$-$C_4$ alkylene oxide group, examples being vinyl ethers and allyl ethers of poly-$C_2$-$C_4$ alkylene glycols or $C_1$-$C_{10}$ alkyl-poly-$C_2$-$C_4$ alkylene glycols, esters of monoethylenically unsaturated monocarboxylic and dicarboxylic acids having 3 to 8 C atoms with poly-$C_2$-$C_4$ alkylene glycols or $C_1$-$C_{10}$ alkyl-poly-$C_2$-$C_4$ alkylene glycols, amides of monoethylenically unsaturated monocarboxylic and dicarboxylic acids having 3 to 8 C atoms with poly-$C_2$-$C_4$ alkylene glycol amines or $C_1$-$C_{10}$ alkyl-poly-$C_2$-$C_4$ alkylene glycol amines ethylenically unsaturated compounds having at least one having a basic nitrogen or quaternized nitrogen atom such as diallyldimethyl ammonium chloride, N-methyl-N-vinylimidazolium salts such as the chloride, sulfate or methosulfate, N-(2-(dimethylamino)ethyl) acrylamide, 2-(N,N-dimethylamino)ethyl acrylate, 2-(N,N-dimethylamino)ethyl methacrylate, 2-(N,N-dimethylamino)ethylacrylamide, 3-(N,N- dimethylamino)propylacrylamide, 3-(N,N-dimethylamino) propylmethacrylamide, 2-(N,N-dimethylamino) ethylmethacrylamide, 2-(N,N,N-trimethylammonio)ethyl acrylate chloride, 2-(N,N,N-trimethylammonio)ethyl methacrylate chloride, 2-(N,N,N-trimethylammonio)ethylmethacrylamide chloride, 3-(N,N,N-trimethylammonio)propylacrylamide chloride, 3-(N,N,N-trimethylammonio) propylmethacrylamide chloride, 2-(N,N,N-trimethylammonio)ethylacrylamide chloride, and the corresponding sulfates and methyl sulfates.

vinyl aromatic monomers, such as styrene, α-methylstyrene, vinyltoluene, tert-butylstyrene, vinylpyridines;

vinyl and allyl esters of aliphatic carboxylic acids having 1 to 20 C atoms, examples being vinyl acetate, vinyl propionate, vinyl butyrate, vinyl hexanoate, vinyl laurate, and vinyl stearate;

conjugated diolefins such as butadiene and isoprene, and halovinyl compounds such as chloroethene (vinyl chloride), 1,1-dichloroethene (vinylidene chloride), fluoroethene, 1,1-difluoroethene, and tetrafluoroethene.

Unless otherwise stated akyl mar refer to $C_1$-$C_7$-alkyl and may be methyl, ethyl, propyl, isopropyl, n-butyl, 2-butyl, sec-butyl, tert-butyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl etc.

The following examples only serve to illustrate the invention. The numerous possible variations that are obvious to a person skilled in the art also fall within the scope of the invention.

Experimental Part

Unless otherwise stated the following experiments have been performed by applying standard equipment, methods, chemicals, and biochemicals as used in genetic engineering, fermentative production of chemical compounds by cultivation of microorganisms and in the analysis and isolation of products. See also Sambrook et al, and Chmiel et al as cited herein above.

Materials and Methods a) Materials

All chemicals and biochemicals were from Roche (Mannheim, Germany), Sigma (Deisenhofen, Germany), and AppliChem. The enzymes for DNA manipulation, DNA size markers, protein molecular mass markers and the molecular mass standard for SDS/PAGE were from Fermentas GmbH (St. Leon-Rot, Germany). *E. coli* strain BL21 was from Stratagene. Sequencing primers were purchased from MWG-Biotech AG (Ebersberg, Germany). Coenzyme A is from MP Biomedicals. CoA-esters of glutaric and acetic acids were prepared from the corresponding anhydrides (Simon, E. J & Shemin, D. (1953) *J. Am. Chem. Soc.* 75, 2530).

b) Organisms and Growth

*E. coli* $DH_5\alpha$, used for cloning, and *E. coli* BL21, used for expression were grown under anaerobic conditions at room temperature on Standard I medium (1.5% peptone, 0.3% yeast extract, 100 mM NaCl, 5 mM glucose; Merck, Darmstadt), supplemented with 50 mM MOPS, 3 mM cysteine hydrochloride, 10 mM Na-glutamate, riboflavin and $FeCl_2$, at various concentrations.

c) Enzyme Activity Assay

2-Hydroxyglutarate dehydrogenase activity was measured at ambient temperature in cuvettes of 0.5 ml total volume containing 0.1 M Tris/HCl pH 8.0, 0.2 mM NADH and 2-hydroxyglutarate dehydrogenase at room temperature. After addition of 1 mM α-ketoglutarate, the absorbance decrease of NADH was monitored at 340 nm ($\epsilon$=6.3 $mM^{-1}$ $cm^{-1}$) (Bresser J (1997) (R)-2-Hydroxyglutarat-Dehydrogenase aus *Acidaminococcus fermentans*. PhD Thesis, Philipps-Universität Marburg, Germany; Martins B M, Macedo-Ribeiro S, Bresser J, Buckel W, Messerschmidt A (2005) Structural basis for stereo-specific catalysis in $NAD^+$-dependent (R)-2-hydroxyglutarate dehydrogenase from *Acidaminococcus fermentans*. Febs J 272:269-281).

Glutaconate CoA-transferase activity assay was performed aerobically at room temperature. The increase of absorbance was followed at 412 nm, $\Delta\epsilon$=14 $mM^{-1}$ $cm^{-1}$. Reagents used in assay are 0.1 M potassium phosphate pH 7.0, 0.2 M sodium acetate, 1 mM oxaloacetate, 1 mM 5,5'-dithiobis(2-nitrobenzoate) (DTNB), 20 μg citrate synthase, 0.1 mM glutaryl-CoA, total volume 0.5 ml (Buckel W, Dorn U, Semmler R (1981) Glutaconate CoA-transferase from *Acidaminococcus fermentans*. Eur J Biochem 118:315-321; Jacob U, Mack M, Clausen T, Huber R, Buckel W, Messerschmidt A (1997) Glutaconate CoA-transferase from *Acidaminococcus fermentans*: the crystal structure reveals homology with other CoA-transferases. Structure 5:415-426).

2-Hydroxyglutaryl-CoA dehydratase activity was measured under anoxic conditions at ambient temperature in cuvettes of 0.5 ml total volume containing 50 mM Mops/KOH pH 7.0, 10 mM dithiothreitol, 5 mM $MgCl_2$, 0.1 mM dithionite, 0.4 mM ATP, and 2-hydroxyglutarate dehydrogenase with activator. After 10 minutes of incubation the reaction was started with 2 mM acetyl-CoA and 2 mM (R)-2-hydroxyglutarate. The increase of absorbance due to the formation of glutaconyl-CoA was followed at 290 nm ($\epsilon$=2.2 $mM^{-1}$ $cm^{-1}$) (Kim J, Darley D J, Buckel W, Pierik A J (2008) An allylic ketyl radical intermediate in clostridial amino-acid fermentation. Nature 452:239-242).

Glutaconate was enzymatically determined with 2 mM acetyl-CoA, 50 mM potassium phosphate pH7.0, 0.25 mM NADPH, glutaconate and using a catalytic amount of enzymes glutaconate-CoA transferase, glutaconyl-CoA decarboxylase [3,5,6] and crotonyl-CoA carboxylase/reductase [9]. The formation of $NADP^+$ was measured spectrophotometrically at 340 nm.

Glutaconate was also determined by HPLC at room temperature with UV detection at 210 nm using a C18 reverse-phase column in 20 mM sulfuric acid.

d) Other Biochemical Methods

Protein concentrations were determined using the Bio-Rad microassay with bovine serum albumin as standard. SDS-PAGE was done in a Mini Protein apparatus (Bio-Rad, Heidelberg, Germany). Proteins were stained with Coomassie brilliant blue (Serve, Heidelberg, Germany).

Example 1

Cloning of Genes

Cloning Methods

Routine manipulation of DNA, PCR and construction of recombinant plasmids were performed as described in (Sambrook J & Russell D W (2001) Molecular Cloning: a Laboratory Manual, $3^{rd}$ edn. Cold Spring. Harbor Laboratory Press, Cold Spring Harbor, N.Y.). PfuUltra High-Fidelity DNA Polymerase (Stratagene, USA) was used for the PCR amplification of gctAB using the following primers containing the NdeI:
(SEQ ID NO: 39)
5'-ATGGT ACATATGTGAGT AAAG TAATGACGTTAAAAGACGCAAT CG-3' and

XhoI:
(SEQ ID NO: 40)
5'-ATGGTACTCGAGTTATTTTGCTTCC GTGGGGA CCTGG-3' restriction sites.

Figure 2A:
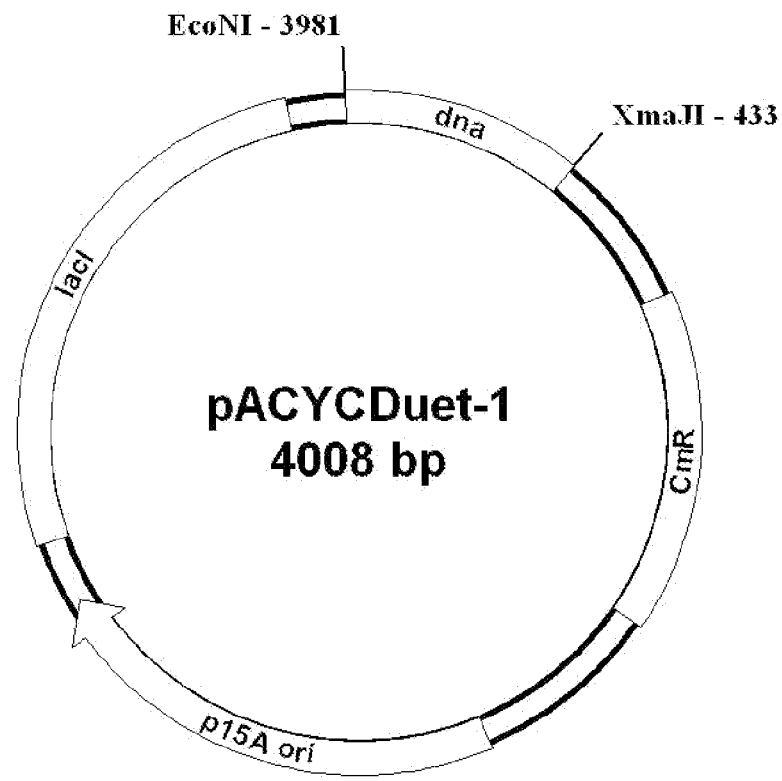
FIG. 2 depicts schematically the construction of recombinant plasmid pACYCDuet-1 (FIG. 2A) in which the coding sequences for 2-hydroxyglutarate dehydrogenase (hgdH) and glutaconate CoA-transferase (gctAB), (subunits A and B) are inserted (FIG. 2B).
Figure 2B:
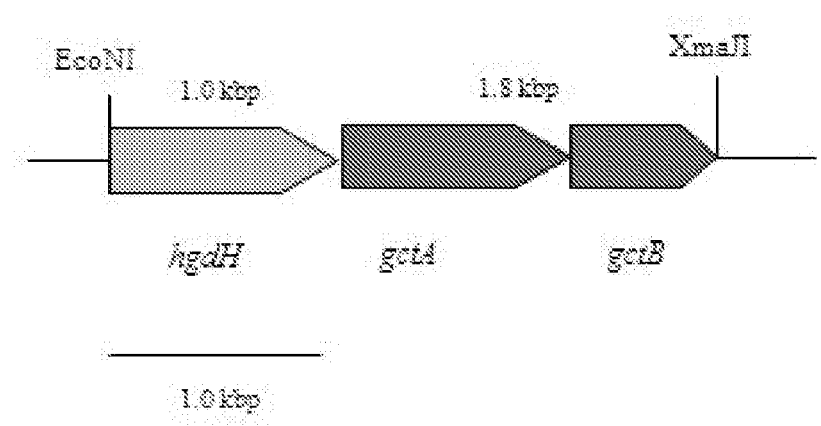

The genes hgdH (2-hydroxyglutarate dehydrogenase) and gctAB (glutaconate CoA-transferase) from *A. fermentans* were subcloned into pACYCDuet-1 vector (Novagen) (SEQ ID NO:13) from pET-Duet-1 and pJF118HE, respectively (FIG. 2) (Fürste J P, Pansegrau W, Frank R, Blöcker H, Scholz P, Bagdasarian M, Lanka E (1986) Molecular cloning of the plasmid RP4 primase region in a multi-host-range tacP expression vector).

Figure 3A:
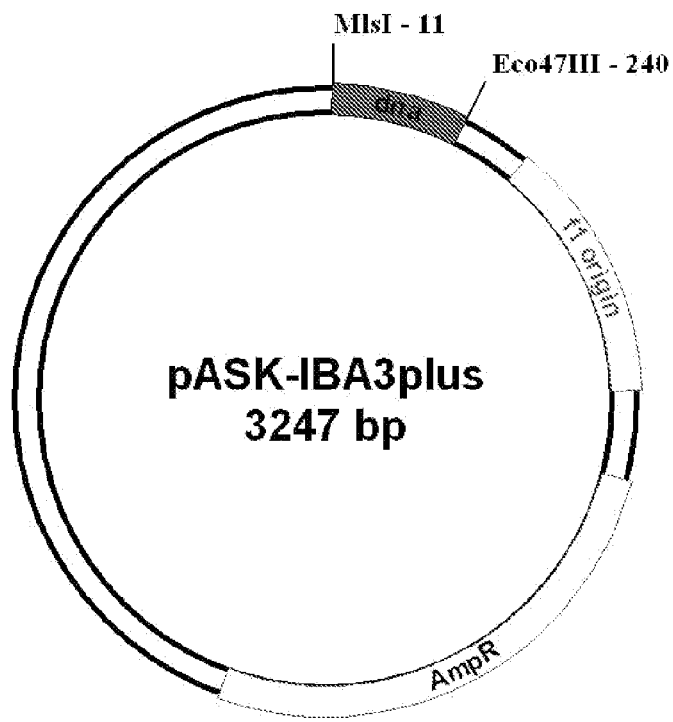
FIG. 3 depicts schematically the construction of recombinant plasmids pASK-IBA3plus (FIG. 3A) in which the coding sequences for 2-hydroxyglutaryl-CoA dehydratase (subunits hdgA and hgdB) and its activator (hdgC) are inserted (FIG. 3B).
Figure 3B:
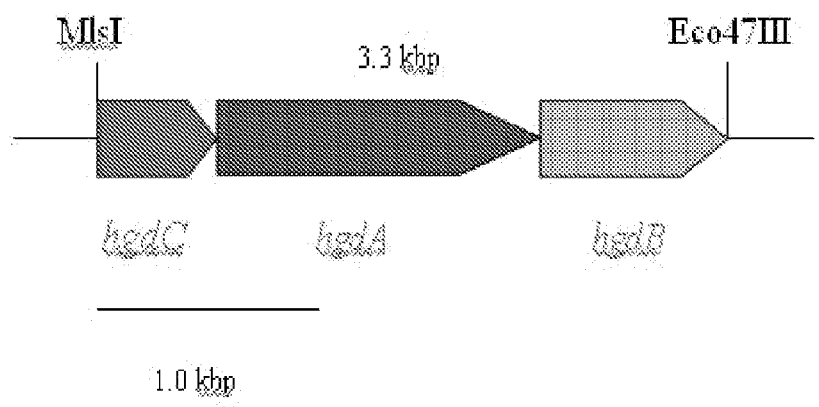

For cloning of hgdAB (2-hydroxyglutaryl-CoA dehydratase) from *C. symbiosum* and its activator hgdC from *A. fermentans* the pASK-IBA3plus vector (IBA GmbH, Göttingen, Germany) (SEQ ID NO:14) was used (FIG. 3).

Ligation and Transformation Conditions for hgdH in pACY-CDuet-1 Vector

The gene hgdH in pASKIBA7+ (laboratory collection) was subcloned into pETDuet (same procedures as described below) and then transferred to pACYCDuet-1, which can express up to 8 genes (10 kb). Before ligation, pETDuet_hgdH and pACYCDuet-1 vector were separately treated with restriction enzymes BamHI and EcoNI (Fermentas) for 1 h at 37° C. (Table 1).

TABLE 1

Digestion with BamHI and EcoNI

| Component | Amount per reaction (µl) |
|---|---|
| Distilled water (dH₂O) | 7.0 |
| 10x Buffer Tango | 6.0 |
| BamHI | 1.0 |
| EcoNI | 1.0 |
| pETDuet_hgdH/pACYCDuet-1 vector | 15.0 |
| Total volume | 30.0 |

TABLE 2

Ligation reaction mixture

| Component | Amount per reaction (µl) |
|---|---|
| Distilled water (dH₂O) | 14.0 |
| 10x Ligation buffer | 3.0 |
| T4 DNA ligase (Fermentas) | 1.0 |
| hgdH (Table 1) | 10.0 |
| pACYCDuet-1 vector (Novagen) | 2.0 |
| Total volume | 30.0 |

The ligation reaction (Table 2) was performed at 23° C. After one hour T4 DNA ligase (Fermentas) was inactivated by incubation at 65° C. for 10 minutes. The salts from the ligation mixture were removed by drop dialysis, using a 0.025 µm Millipore membrane, at ambient temperature for 30 minutes. Ligation mixture was added to 50 µl competent *E. coli* DH₅α cells and transferred to an Electroporation Cuvette (Molecular BioProducts). A pulse was given to the cuvette using the following settings: 25 µF, 1.8 kV and 200 Ohm. The cuvette was washed with 300 µl Standard I medium and transferred to a sterile 1.5 ml Eppendorf tube. The transformation mixture was incubated for 1 h at 37° C. and plated on a LB agar plate containing chloramphenicol (50 µg·ml⁻¹). The agar plate was incubated overnight at 37° C. Ten white colonies were picked and separately incubated in Standard medium overnight at 37° C.: DNA was extracted using the Fermentas kit and digested with BamHI and EcoNI. One out of three correct fragments was extracted from the gel and ligated with gctAB.

Ligation and Transformation Conditions for gctAB in pACY-CDuet-1 Vector, Containing hgdH Gene The gctAB genes were treated with two restriction enzymes NdeI and XhoI, which recognition sites were introduced by PCR reaction (Tables 3 and 4). Also the pACYC-Duet-1 vector containing the hgdH gene, pACYCDuet-1_hgdH, was treated with the same restriction enzymes (Table 5). The ligation reaction and transformation were performed under conditions, explained in Table 6.

TABLE 3

PCR reaction mixture

| Component | Amount per reaction (µl) |
|---|---|
| Distilled water (dH2O) | 24.0 |
| 10x PfuUltra HF reaction buffer | 5.0 |
| dNTPs (2 mM) | 5.0 |
| primer 1 (5 µM) | 5.0 |
| primer 2 (5 µM) | 5.0 |
| DNA template (8 ng) | 5.0 |
| PfuUltra HF DNA polymerase (2.5 U/µl) | 1.0 |
| Total reaction volume | 50.0 |

TABLE 4

PCR reaction conditions

| Segment | Number of cycles | Temperature | Duration |
|---|---|---|---|
| Initial denaturation | 1 | 98° C. | 3 minutes |
| Denaturation | 29 | 98° C. | 10 seconds |
| Annealing | 29 | 68° C. | 20 seconds |
| Extension | 29 | 72° C. | 50 seconds |
| Final extension | 1 | 72° C. | 5 minutes |

TABLE 5

Protocol for digestion

| Component | Amount per reaction (µl) |
|---|---|
| Distilled water (dH₂O) | 6.0 |
| 10x Buffer R | 2.0 |
| DNA (PCR product)/pACYCDuet-1_hgdH | 10.0 |
| NdeI | 1.0 |
| XhoI | 1.0 |

TABLE 6

Ligation reaction mixture

| Component | Amount per reaction (µl) |
|---|---|
| Distilled water (dH₂O) | 10.0 |
| 10x Ligation buffer | 2.0 |
| T4 DNA ligase (Fermentas) | 1.0 |
| gctAB | 6.0 |
| pACYCDuet-1_hgdH | 1.0 |
| Total volume | 20.0 |

Ligation and Transformation Conditions for hgdAB and its Activator Gene hgdC in pASK-IBA 3 Vector The activator hgdC was introduced in pASK-IBA 3 vector, containing hgdAB genes. Both DNA were separately treated with restriction enzymes Eco47III and MIsI (Fermentas) for 1 h at 37° C. (Table 7). After digestion the enzyme was inactivated by incubation at 65° C. for 20 minutes. The salts were removed by drop dialysis as above, at ambient temperature for 30 minutes. To the salt-free reaction, containing pASK-IBA 3_hgdAB, was added 1 μl (1 u/μl) of Shrimp Alkaline Phosphatase (Fermentas), 2 μl of 10× Reaction buffer and incubated for 1 h at 37° C. The reaction was stopped by heating at 65° C. for 15 minutes. Ligation reaction (Table 8) and transformation were performed under the conditions explained above. Carbenicillin (100 μg·ml$^{-1}$) replaced chloramphenicol as antibiotic.

TABLE 7

Digestion of hgdC and hgdAB

| Component | Amount per reaction (μl) |
| --- | --- |
| Distilled water (dH$_2$O) | 1.0 |
| 10x Buffer O | 2.0 |
| DNA (hgdC)/pASK-IBA 3_hgdAB | 15.0 |
| Eco47III | 1.0 |
| MIsI | 1.0 |

TABLE 8

Ligation reaction mixture

| Component | Amount per reaction (μl) |
| --- | --- |
| 10x Ligation buffer | 2.0 |
| T4 DNA ligase (Fermentas) | 1.0 |
| hgdC | 16.0 |
| pASK-IBA3_hgdAB | 1.0 |
| Total volume | 20.0 |

Gene Expression

The genes were transformed into modified *E. coli* BL21-CodonPlus (DE3). An overnight anaerobic preculture (100 ml) of a fresh single colony was used to inoculate 1 liter Standard I medium, described above, containing antibiotics (carbenicillin, 100 μg·ml$^{-1}$; chloramphenicol, 50 μg·ml$^{-1}$) and grown at the same conditions. When the culture reached OD$_{578}$=0.2, gene expression was induced with isopropyl-1-thio-β-D-galactoside, IPTG (240 mg·liter$^{-1}$) and anhydrotetracycline, AHT (200 μg·liter$^{-1}$). Cells were harvested 3 hours after induction (at OD$_{578}$=0.573), washed and suspended in 20 ml of buffer (50 mM MOPS, 5 mM MgCl$_2$ and 2 mM DTT) under anoxic conditions. The induced *E. coli* cells were lysed by French press and cell debris was removed by ultracentrifugation at 100 000 g at 4° C. for 1 hour.

Example 2

Fermentative Production of Glutaconate

The first step was the construction of a plasmid, which comprises the six genes of 2-hydroxyglutarate dehydrogenase (hgdH), glutaconate CoA-transferase (gctAB), and the activator of 2-hydroxyglutaryl-CoA dehydratase (hgdC) from *A. fermentans* as well as 2-hydroxyglutaryl-CoA dehydratase (hgdAB) from *C. symbiosum* (see example 1).

Determination of Enzyme Activities

In Table 9 the enzymatic activities are shown, which were measured in the recombinant *E. coli* strain.

TABLE 9

Enzymatic activities in the recombinant *E. coli* BL21

| Enzyme | Activity, U | Specific activity, U/mg |
| --- | --- | --- |
| 2-Hydroxyglutarate dehydrogenase | 730 | 250 |
| Glutaconate CoA-transferase | 0.71 | 0.25 |
| 2-Hydroxyglutaryl-CoA dehydratase + activator | 0.23 | 0.80 |

Determination of Glutaconate

After growth, the glutaconate concentration in the medium was 0.30±0.05 mM; when glutamate was omitted, the concentration decreased to 0.1 mM (Table 10). Hence, glutaconate indeed was produced indicating that the enzymes work also in vivo. However, the precursor of glutaconate is glutamate, either added as such or from peptone, rather than glucose as initially anticipated.

TABLE 10

The concentration of glutaconate depended on glutamate concentration

| | glutaconate, mM |
| --- | --- |
| without glutamate | 0.10 ± 0.05 |
| 10 mM glutamate | 0.30 ± 0.05 |

Addition of riboflavin and iron(II) chloride in the Standard I medium, described above, increased the concentration of glutaconate (Table 11,12).

TABLE 11

Glutaconate in the medium

| | glutaconate, mM |
| --- | --- |
| 2 mM FeCl$_2$, without riboflavin | 1.33 |
| 2 mM FeCl$_2$ + 0.2 mM riboflavin | 1.41 |
| 2 mM FeCl$_2$ + 0.4 mM riboflavin | 0.85 |

TABLE 12

Glutaconate in the cell free extract

| | glutaconate, mM |
| --- | --- |
| 2 mM FeCl$_2$, without riboflavin | 0.19 |
| 2 mM FeCl$_2$ + 0.2 mM riboflavin | 0.23 |
| 2 mM FeCl$_2$ + 0.4 mM riboflavin | 0.21 |

The cell-free extract was prepared from 590 mg wet packed cells (approx. 118 mg dried cells) in 20 ml 50 mM MOPS pH 7.4. Assuming a volume of 2.5 ml/g dried cells (Brock M, Bucket W (2004) *On the mechanism of action of the antifungal agent propionate. Eur J Biochem* 271:3227-41) the internal concentration of glutaconate rises from 0.23 mM to 16 mM.

The original strain *E. coli* BL21 was grown and analysed under the same conditions as the recombinant strain and glutaconate was not detected.

Discussion

The data indicate that the recombinant *E. coli* strain indeed produced glutaconate. The substrate, however, is most likely glutamate rather than glucose, because glutamate enhanced the production glutaconate threefold. In the absence of the amino acid, the glutamate present in the peptone most likely is the precursor of glutaconate (Table 10). The use of glucose as precursor requires an electron acceptor, which cannot be oxygen because of the extreme sensitivity of the activator towards this agent (Buckel W, Golding B T (2006) Radical enzymes in anaerobes. Annu Rev Microbiol 60:27-49; Kim J, Darley D J, Buckel W, Pierik A J (2008) An allylic ketyl radical intermediate in clostridial amino-acid fermentation. Nature 452:239-242). The iron requirement (Table 11) stems from the iron sulfur clusters in the dehydratase (HgdAB) and its activator (HgdC). The slight improvement with riboflavin is probably due to riboflavin-5'-phosphate (FMN) as prosthetic group of the dehydratase (Hans M, Bucket W, Bill E (2000) *The iron-sulfur clusters in 2hydroxyglutatyl-CoA dehydratase from Acidaminococcus fermentans. Biochemical and spectroscopic investigations. Eur J Biochem* 267: 7082-93). The data further indicate that the concentration of glutaconate inside the cells (16 mM) is about 12-times higher than outside (1.4 mM). Therefore, the export of glutaconate, probably mediated by the succinate transporter (Janausch I G, Zientz E, Tran Q H, Kröger A, Unden G. (2002) *C4-dicarboxylate carriers and sensors in bacteria. Biochim Biophys Acta.* 1553:39-56), appears to limit the production of the dicarboxylic acid.

Example 3

Evaluation of Alternative Substrates for the Enzymes of the Glutaconate Production Pathway Non-limiting examples of further substrates are given below:

a) 2-Hydroxyglutaryl-CoA dehydratase from *Clostridium symbiosum* and activator from *Acidaminococcus fermentans*

TABLE 13

| Substrate | Product | $K_m$ (μM) | $k_{cat}$ ($s^{-1}$) |
|---|---|---|---|
| (R)-2-Hydroxyglutaryl-CoA | (E)-Glutaconyl-CoA | 52 | 83 |
| (R,S)-2-Hydroxyadipoyl-CoA | (E)-Hex-2-enedioyl-CoA | 100 | 17.4 |
| (E,E)-Muconyl-CoA | (R)-2-Hydroxyhex-4-enedioyl-CoA | 570 | 1.9 |
| (E,E)-2-Hydroxymuconyl-CoA | (R)-2-Hydroxy-5-oxoadipoyl-CoA | 1100 | 0.9 |
| Butynedioyl-CoA (Acetylenedicarboxyl-CoA) | Oxaloacetate + CoA | Not determined | |

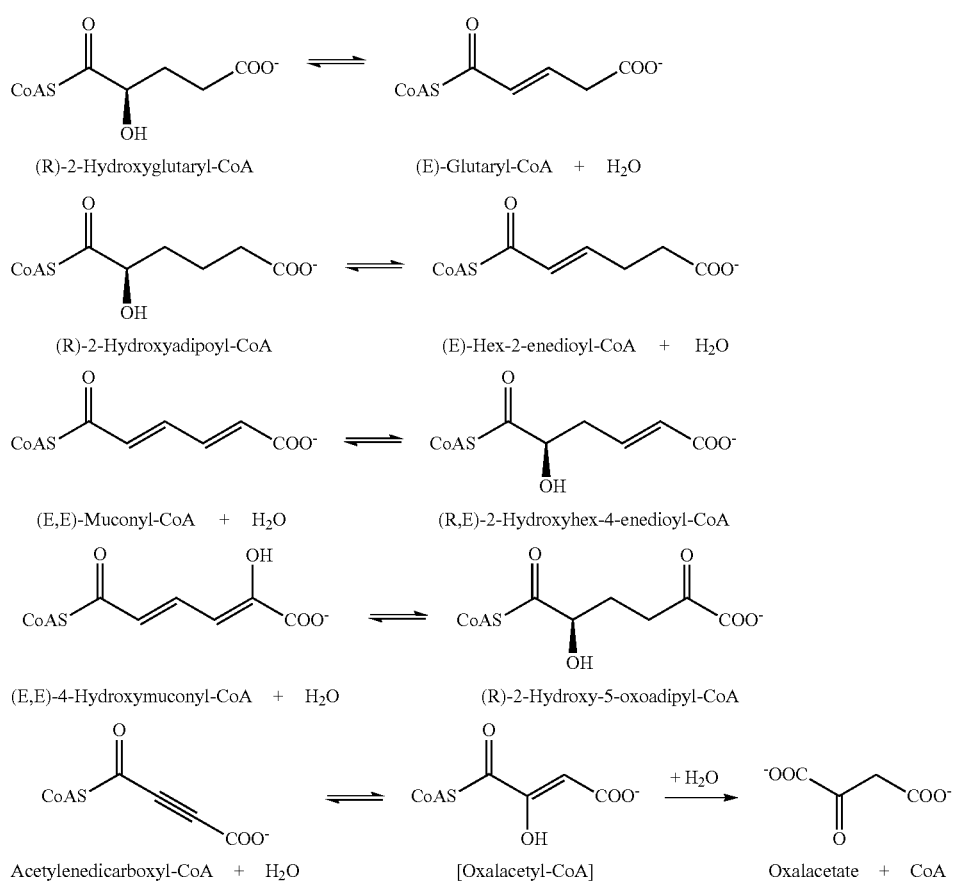

Scheme 1. Reactions catalysed by 2-hydroxyglutaryl-CoA dehydratase.

It was assumed that the enzyme also exhibits also 2R-specificity with substrates other than (R)-2-hydroxyglutaryl-CoA. (Anutthaman Parthasarathy and Wolfgang Buckel, unpublished)

b) (R)-2-Hydroxyglutarate Dehydrogenase from *A. fermentans*

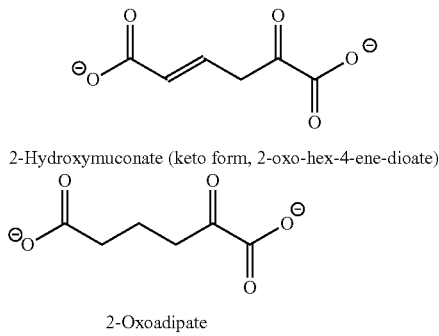

Scheme 2: Alternative substrates of (R)-2-hydroxyglutarate dehydrogenase

2-Hydroxymuconate (keto form, 2-oxo-hex-4-ene-dioate)

2-Oxoadipate

Most likely, both 2-oxoacids are reduced to the 2R-enantiomers. $K_m$ and $k_{cat}$ values were not determined yet. The enzyme is specific for $NAD^+$/NADH. No activity was observed with NADPH/2-oxoglutarate or NADH/oxaloacetate.

c) Glutaconate CoA-transferase from *A. fermentans*

This enzyme acts on (E)-glutaconate, glutarate, (R)-2-hydroxyglutarate, adipate; acetate, propionate, acrylate (Buckel, W., Dorn, U. & Semmler, R. 1981. Glutaconate CoA-transferase from *Acidaminococcus fermentans*. Eur. J. Biochem. 118, 315-321).

(R)-2-Hydroxyglutaryl-CoA, (E)-glutaconyl-CoA, muconyl-CoA, butynedioyl-CoA (acetylenedicarboxyl-CoA), 4-oxo-hex-2-eneoyl-CoA, 4-nitro-but-2-enoyl-CoA and (RS)-2-hydroxyadipoyl-CoA were prepared by this enzyme using acetyl-CoA and an excess of the neutralised acid. Since the R-emantiomers react faster than S, the product should be mainly (R)-2-hydroxyadipoyl-CoA (Anutthaman Parthasarathy and Wolfgang Buckel, unpublished).

Conclusion:

As all three enzymes of the glutaconate production pathway can also use the C-6 homologues, the production of hex-2-enedioic acid from 2-oxoadipic or 2-aminoadipic acid is also feasible.

The following examples illustrate applicability of glutaconate (a compound of formula I) as obtainable by a biocatalytic method of the present invention for the preparation of organic polymers.

Example 4

Preparation of Glutaconic Acid-Acrylic Acid Copolymers

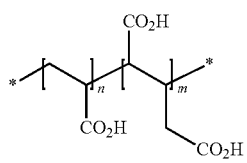

Copolymers from glutaconic acid and acrylic acid with molar ratios from 1:1 to 1:3 (glutaconic acid:acrylic acid) were synthesized via radical polymerization methods in water solution using sodium peroxide disulfate (NAPS) as radical initiator.

a) Glutaconic acid-co-acrylic acid (1:1 mol)

In a 500 ml reactor flask were placed glutaconic acid (10.00 g) and distilled water (30.00 g). The mixture was stirred at 98° C. under a nitrogen atmosphere for 15 minutes. A solution of NAPS (0.23 g) in distilled water (15.31 g) was added drop wise to the reactor over a period of 5 hours. 5 Minutes after the beginning of the addition of the initiator, a solution of acrylic acid (5.54 g) in distilled water (25.00 g) was also added drop wise to the reactor over a period of 4 hours. The temperature of the reaction was kept at 98° C. At the end of the initiator addition, the reaction was left at 98° C. for other 2 hours and then cooled to room temperature.

A light yellow polymer solution was obtained with a solid content of 18.71 g. K-Value=11.3 g (1 wt % in deionized water).

b) Glutaconic acid-co-acrylic acid (1:2 mol)

In a 500 ml reactor flask were placed glutaconic acid (10.00 g) and distilled water (30.00 g). The mixture was stirred at 98° C. under a nitrogen atmosphere for 15 minutes. A solution of NAPS (0.32 g) in distilled water (20.76 g) was added drop wise to the reactor over a period of 6 hours. 5 Minutes after the beginning of the addition of the initiator, a solution of acrylic acid (11.08 g) in distilled water (33.23 g) was also added drop wise to the reactor, over a period of 5 hours. The temperature of the reaction was kept at 98° C. At the end of the initiator addition, the reaction was left at 98° C. for other 2 hours and then cooled to room temperature.

A light yellow polymer solution was obtained with a solid content of 20.59 g. K-Value=14.7 g (1 wt % in deionized water).

c) Glutaconic acid-co-acrylic acid (1:3 mol)

In a 500 ml reactor flask were placed glutaconic acid (10.00 g) and distilled water (30.00 g). The mixture was stirred at 98° C. under a nitrogen atmosphere for 15 minutes. A solution of NAPS (0.40 g) in distilled water (26.00 g) was added drop wise to the reactor over a period of 6 hours. 5 Minutes after the beginning of the addition of the initiator, a solution of acrylic acid (16.62 g) in distilled water (49.86 g) was also added drop wise to the reactor, over a period of 5 hours. The temperature of the reaction was kept at 98° C. At the end of the initiator addition, the reaction was left at 98° C. for other 2 hours and then cooled to room temperature.

A light yellow polymer solution was obtained with a solid content of 20.90 g. K-Value=17.20 g (1 wt % in deionized water).

$M_n$=13.800 Da; $M_w$=55.000 Da

K-Value Determination:

The K-values of the copolymer water solutions were determined in a deionized water solution at pH=7, T=25° C. and with a polymer concentration of 1 wt %, according to the procedure described by H. Fikenscher, in "Cellulose-Chemie" (1932), Band 13, 48-64, 71-74.

The documents as cited herein are all incorporated by reference.

TABLE 14

List of SEQ ID NOs

| Designation | Organism | Type | SEQ ID NO: |
|---|---|---|---|
| HgdH | *A. fermentans* | NS | 1 |
|  |  | AS | 2 |
| GctAB | *A. fermentans* | NS (A) | 3 |
|  |  | AS (A) | 4 |
|  |  | NS (B) | 5 |
|  |  | AS (B) | 6 |

TABLE 14-continued

List of SEQ ID NOs

| Designation | Organism | Type | SEQ ID NO: |
|---|---|---|---|
| HgdAB | C. symbiosum | NS (A) | 7 |
| | | AS (A) | 8 |
| | | NS (B) | 9 |
| | | AS (B) | 10 |
| HgdC | A. fermentans | NS | 11 |
| | | AS | 12 |
| pACYC Duet-1 | | Plasmid | 13 |
| pASK-IBA3plus | | Plasmid | 14 |
| HgdH | F. nucleatum | NS | 15 |
| | | AS | 16 |
| GctAB | C. symbiosum | NS (A) partial | 17 |
| | | AS (A) partial | 18 |
| | | NS (B) partial | 19 |
| | | AS (B) partial | 20 |
| GctAB | F. nucleatum | NS (A) | 21 |
| | | AS (A) | 22 |
| | | NS (B) | 23 |
| | | AS (B) | 24 |
| HgdAB | A. fermentans | NS (A) | 25 |
| | | AS (A) | 26 |
| | | NS (B) | 27 |
| | | AS (B) | 28 |

TABLE 14-continued

List of SEQ ID NOs

| Designation | Organism | Type | SEQ ID NO: |
|---|---|---|---|
| HgdABD | F. nucleatum | NS (A) | 29 |
| | | AS (A) | 30 |
| | | NS (B) | 31 |
| | | AS (B) | 32 |
| | | NS (C) | 33 |
| | | AS (C) | 34 |
| HgdC | C. symbiosum | NS | 35 |
| | | AS | 36 |
| HgdC | F. nucleatum | NS | 37 |
| | | AS | 38 |
| Nde Primer | | Primer | 39 |
| Xho Primer | | Primer | 40 |

HgdAB Hydroxyglutaryl-CoA Dehydratase (2 subunits)
HgdABD Hydroxyglutaryl-CoA Dehydratase (3 subunits)
HgdC Hydroxyglutaryl-CoA Dehydratase Activator
HgdH Hydroxyglutarate Dehydrogenase
GctAB Glutaconyl-CoA Transferase
A, B, C subunits alpha, beta and gamma
AS Amino acid sequence
NS Nucleic acid sequence

---

The invention claimed is:

1. A biocatalytic method for the production of an unsaturated dicarboxylic acid compound of formula I

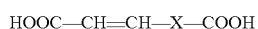  (I)

wherein X represents a linear or branched, optionally unsaturated, optionally substituted hydrocarbon group, wherein X is selected from (CH2)n, with n being an integer from 1 to 4, CH=CH, CH2-C(=O), or CH=C(OH), wherein said method comprises:
converting a 2-hydroxy-substituted dicarboxylic acid compound of formula III

  (III)

wherein X is as defined above;

in a recombinant microorganism co-expressing a glutaconate CoA-transferase and a 2-hydroxyglutaryl-CoA dehydratase, optionally in the presence of a coenzyme A source so that said compound of formula I is formed;

and optionally isolating said compound of formula I in the form of a substantially pure stereoisomer or as a mixture of stereoisomers, wherein said glutaconate CoA-transferase comprises an amino acid sequence having at least 95% sequence identity to the amino acid sequence of SEQ ID NO: 4 and/or 6, SEQ ID NO: 18 and/or 20, or SEQ ID NO: 22 and/or 24, and wherein said 2-hydroxyglutaryl-CoA dehydratase comprises an amino acid sequence having at least 95% sequence identity to the amino acid sequence of SEQ ID NO: 8 and/or 10, SEQ ID NO: 26 and/or 28, or SEQ ID NO: 30, 32 and/or 34.

2. The method of claim 1, wherein said 2-hydroxy-substituted dicarboxylic acid compound of formula III is formed by said recombinant microorganism by a 2-hydroxyglutarate dehydrogenase catalyzing conversion of a 2-oxo-dicarboxylic acid compound of formula II

HOOC—C(=O)—CH2—X—COOH      (II)

wherein X is as defined in claim 1, and wherein said 2-hydroxyglutarate dehydrogenase comprises an amino acid sequence having at least 95% sequence identity to the amino acid sequence of SEQ ID NO: 2 or 16.

3. The method of claim 2, wherein said 2-hydroxyglutarate dehydrogenase is co-expressed by said recombinant microorganism.

4. The method of claim 2, wherein said 2-oxo-dicarboxylic acid compound of formula II is either added to or fermentatively produced by said recombinant microorganism.

5. The method of claim 4, wherein said recombinant microorganism is a glutamate and/or glucose metabolizing aerobic or anaerobic recombinant bacterium, and wherein said compound of formula II is 2-oxoglutarate.

6. The method of claim 5, wherein said glutamate and/or glucose metabolizing recombinant bacterium is from the genus *Escherichia*.

7. The method of claim 1, wherein said recombinant microorganism further comprises an activator protein for the 2-hydroxyglutaryl-CoA dehydratase, and wherein said activator protein comprises an amino acid sequence having at least 95% sequence identity to the amino acid sequence of SEQ ID NO: 12, 36 or 38.

8. The method of claim 7, wherein said 2-hydroxyglutaryl-CoA dehydratase and said activator protein are of prokaryotic or eukaryotic origin.

9. The method of claim 8, wherein said 2-hydroxyglutaryl-CoA dehydratase and said activator protein originate from the same or different anaerobic bacterium having the ability to convert glutamate into glutaconate.

10. The method of claim 9, wherein said anaerobic bacterium is a bacterium of the genus *Acidaminococcus, Clostridium, Fusobacterium,* or *Peptostreptococcus*.

11. The method of claim 10, wherein said anaerobic bacterium is *Acidaminococcus fermentans, Clostridium symbiosum, Clostridium sporosphaeroides, Fusobacterium nucleatum* including all subspecies, or *Peptostreptococcus asaccharolyticus*.

12. The method of claim 1, wherein the glutaconate CoA transferase comprises the amino acid sequence of SEQ ID NO: 4 and/or 6; SEQ ID NO: 18 and/or 20; or SEQ ID NO: 22 and/or wherein the 2-hydroxyglutaryl-CoA dehydratase comprises the amino acid sequence of SEQ ID NO: 8 and/or 10, SEQ ID NO: 26 and/or 28, or SEQ ID NO: 30, 32 and/or 34.

13. The method of claim 2, wherein the 2-hydroxyglutarate dehydrogenase comprises the amino acid sequence of SEQ ID NO: 2 or 16.

14. The method of claim 7, wherein the activator protein comprises the amino acid sequence of SEQ ID NO: 12, 36 or 38.

15. The method of claim 1, wherein the glutaconate CoA transferase is from *A. fermentans*.

16. The method of claim 2, wherein the 2-hydroxyglutarate dehydrogenase is from *A. fermentans*.

17. The method of claim 7, wherein the 2-hydroxyglutaryl-CoA dehydratase is from *C. symbiosum*, and wherein the activator protein is from *A. fermentans*.

18. The method of claim 1, wherein the glutaconate CoA-transferase is encoded by a nucleic acid sequence which is adapted to the codon usage of the microorganism.

19. The method of claim 2, wherein the 2-hydroxyglutarate dehydrogenase is encoded by a nucleic acid sequence which is adapted to the codon usage of the microorganism having the ability to produce the 2-oxo-dicarboxylic acid compound of formula II.

20. The method of claim 7, wherein the 2-hydroxyglutaryl-CoA dehydratase is encoded by a nucleic acid sequence which is adapted to the codon usage of the microorganism.

21. The method of claim 1, wherein the glutaconate CoA-transferase and 2-hydroxyglutaryl-CoA dehydratase are encoded by nucleic acid sequences contained in one or more expression vectors.

22. The method of claim 1, wherein at least one of the glutaconate CoA-transferase and 2-hydroxyglutaryl-CoA dehydratase is heterologous to the recombinant microorganism.

23. The method of claim 1, wherein a compound of formula I is produced, wherein X is selected from CH2, C2H4, CH=CH; CH=C(OH).

24. An expression cassette comprising a first nucleic acid sequence and a second nucleic acid sequence, wherein the first nucleic acid sequence encodes a glutaconate CoA-transferase comprising the amino acid sequence of SEQ ID NO: 4 and/or 6, SEQ ID NO: 18 and/or 20, or SEQ ID NO: 22 and/or 24, or an amino acid sequence having at least 95% sequence identity to the amino acid sequence of SEQ ID NO: 4 and/or 6, SEQ ID NO: 18 and/or 20, or SEQ ID NO: 22 and/or 24, wherein the second nucleic acid sequence encodes a 2-hydroxyglutaryl-CoA dehydratase comprising the amino acid sequence of SEQ ID NO: 8 and/or 10, SEQ ID NO: 26 and/or 28, or SEQ ID NO: 30, 32 and/or 34, or an amino acid sequence having at least 95% sequence identity to the amino acid sequence of SEQ ID NO: 8 and/or 10, SEQ ID NO: 26 and/or 28, or SEQ ID NO: 30, 32 and/or 34, and wherein each of the first nucleic acid sequence and the second nucleic acid sequence is operatively linked to at least one regulatory nucleic acid sequence.

25. A recombinant vector comprising at least one expression cassette of claim 24.

26. A recombinant prokaryotic or eukaryotic host transformed with at least one vector of claim 25.

27. The recombinant host of claim 26 having the ability to produce a 2-oxo-dicarboxylic acid compound of formula II

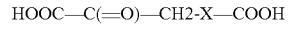

HOOC—C(=O)—CH2—X—COOH      (II)

wherein X represents a linear or branched, optionally unsaturated, optionally substituted hydrocarbon group, wherein X is selected from (CH2)n, with n being an integer from 1 to 4, CH=CH, CH2-C(=O), or CH=C(OH), and wherein, upon expression of the glutaconate CoA-transferase and the 2-hydroxyglutaryl-CoA dehydratase, the compound of formula II is converted to a compound of formula I

HOOC—CH=CH—X—COOH (I)

wherein X is as defined above.

28. The host of claim 27, which is a recombinant strain of a bacterium of the genus *Escherichia*.

* * * * *